(12) United States Patent
Malyj

(10) Patent No.: US 6,601,050 B1
(45) Date of Patent: Jul. 29, 2003

(54) TRAINABLE ADAPTIVE FOCUSED REPLICATOR NETWORK FOR ANALYZING DATA

(75) Inventor: Wasyl Malyj, Davis, CA (US)

(73) Assignee: Large Scale Biology Corporation, Vacaville, CA (US)

(*) Notice: Subject to any disclaimer, the term of this patent is extended or adjusted under 35 U.S.C. 154(b) by 187 days.

(21) Appl. No.: 09/625,572

(22) Filed: Jul. 25, 2000

Related U.S. Application Data

(60) Provisional application No. 60/145,593, filed on Jul. 26, 1999.

(51) Int. Cl.[7] ............................................. G06F 15/18
(52) U.S. Cl. ............................................. 706/20; 707/3
(58) Field of Search ................................ 706/20; 707/3

(56) References Cited

U.S. PATENT DOCUMENTS

| | | | | |
|---|---|---|---|---|
| 5,572,628 A | * | 11/1996 | Denker et al. ................. | 706/25 |
| 5,754,681 A | * | 5/1998 | Watanabe et al. ............. | 382/159 |
| 5,870,735 A | * | 2/1999 | Agrawal et al. ................ | 707/3 |
| 6,138,115 A | * | 10/2000 | Agrawal et al. ................ | 707/3 |
| 6,424,960 B1 | * | 7/2002 | Lee et al. ....................... | 706/20 |
| 6,501,857 B1 | * | 12/2002 | Gotsman et al. .............. | 382/224 |

OTHER PUBLICATIONS

Aldrich, C., "Visualization of transformed multivariate data sets with autoassociative neural networks," *Pattern Recognition Letters* 19:749–764 XP002157124 (1998).

Schwenk and Milgram, "Transformation Invariant Autoassociation with Application to Handwritten Character Recognition," *Advances in Neural Information Processing Systems 7, Proceedings of NIPS94—Neural and Synthetic*, Denver, CO USA, pp. 991–998, XP00978424.

C.M. Bishop, "Neural Networks for Pattern Recognition," Ch. 8.6.2, Oxford University Press Inc., New York (1997).

* cited by examiner

*Primary Examiner*—John Follansbee
*Assistant Examiner*—Michael B. Holmes
(74) *Attorney, Agent, or Firm*—Waddey Patterson; Lucian Wayne Beavers

(57) ABSTRACT

Electronic data is classified using adaptive focused replicator networks (AFRNs). AFRNs are sets of array elements, each array element being trainable in order to replicate a predetermined sub-group of data. Unknown data is inputted into each and every array element in an AFRN array and then replicated by each element array. A comparison is made for each array element to determine the accuracy of each replication. If only one array element successfully replicates the unknown data, then the unknown data is classified in accordance with the corresponding predetermined sub-group of data.

38 Claims, 51 Drawing Sheets

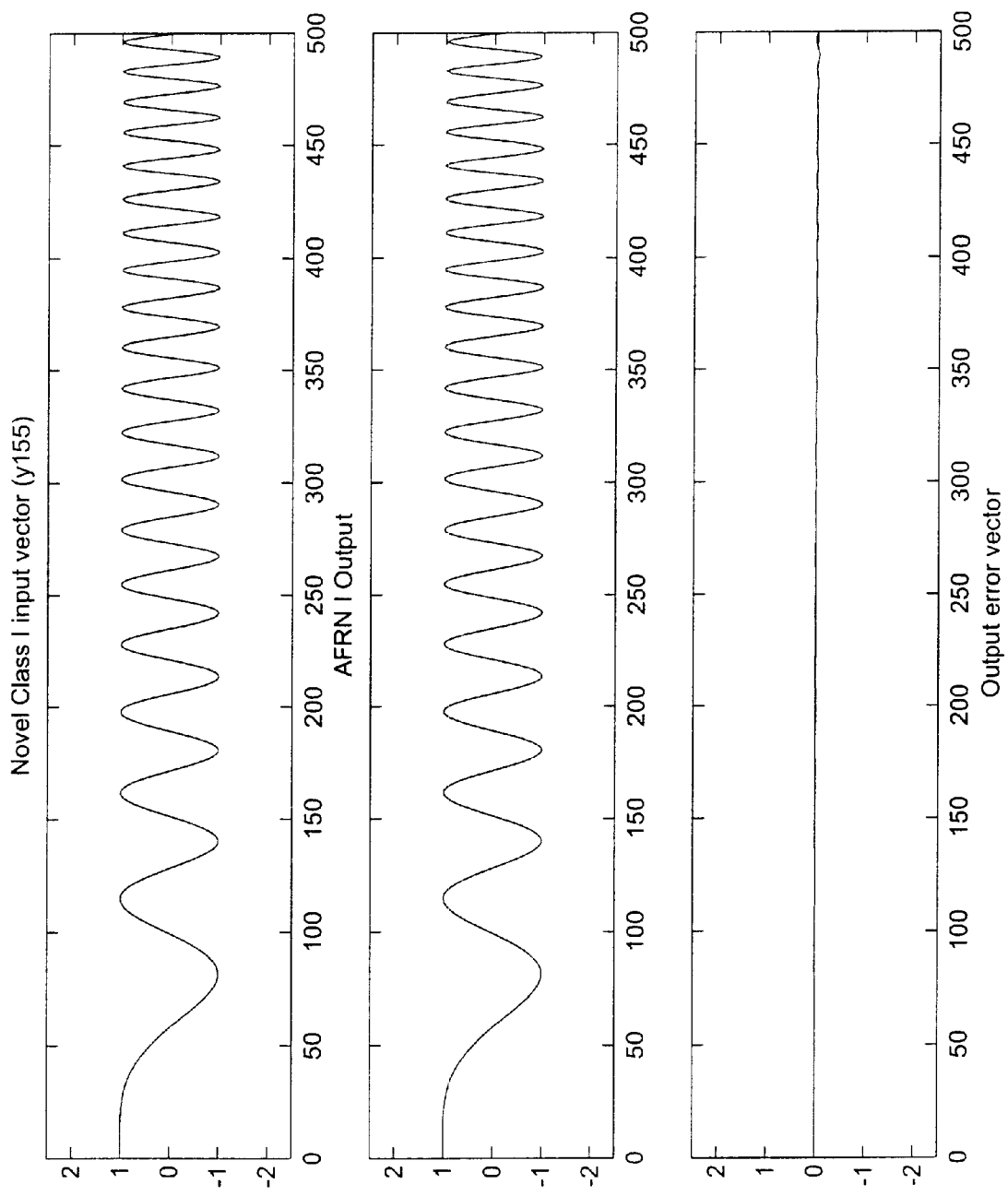

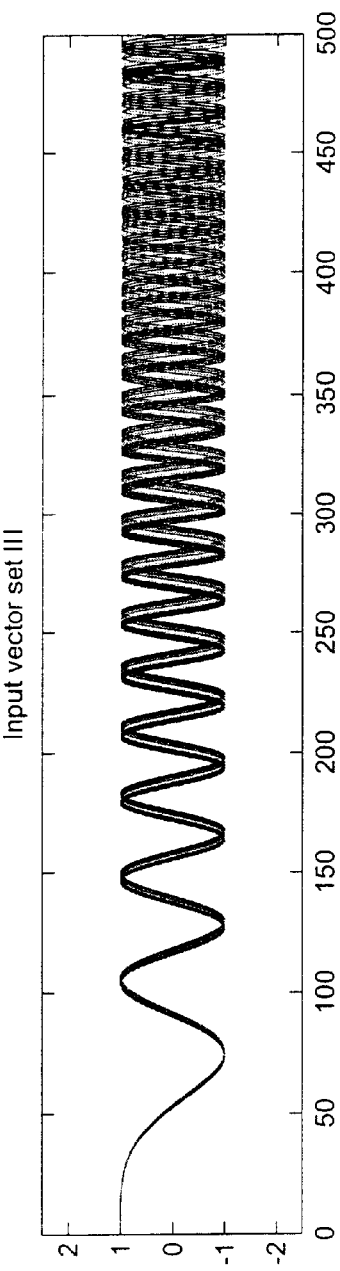
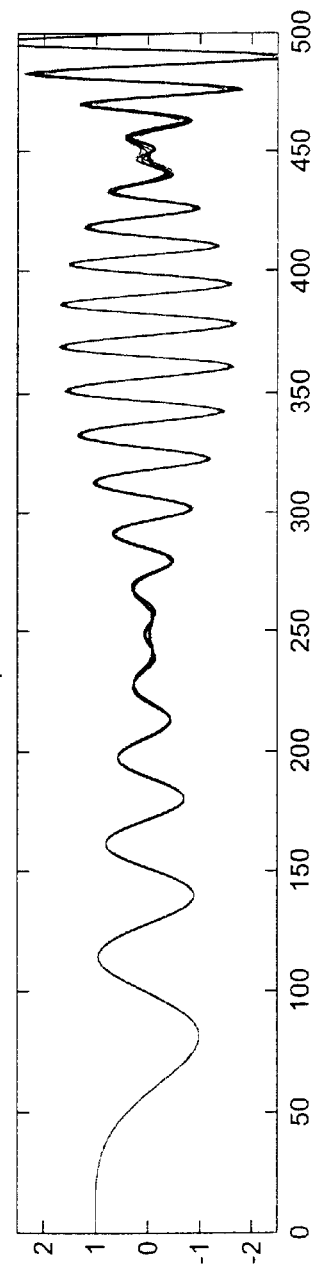
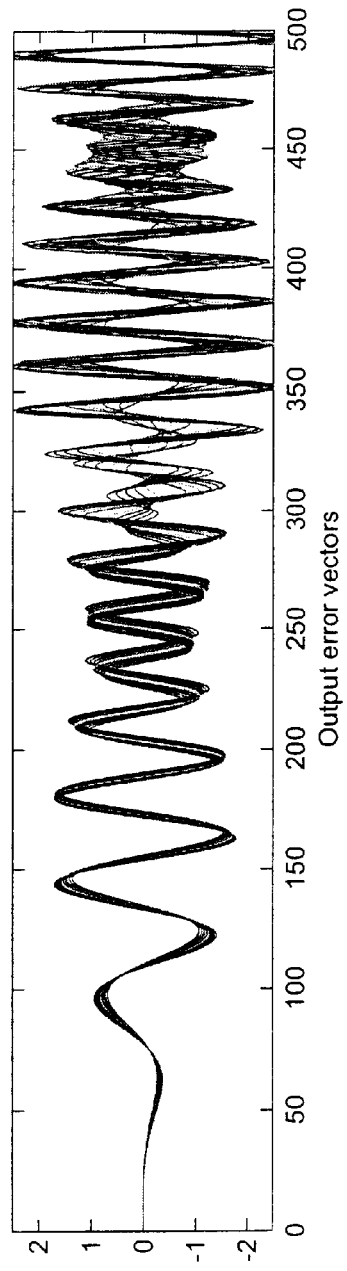
Fig. 11D
Fig. 11E
Fig. 11F

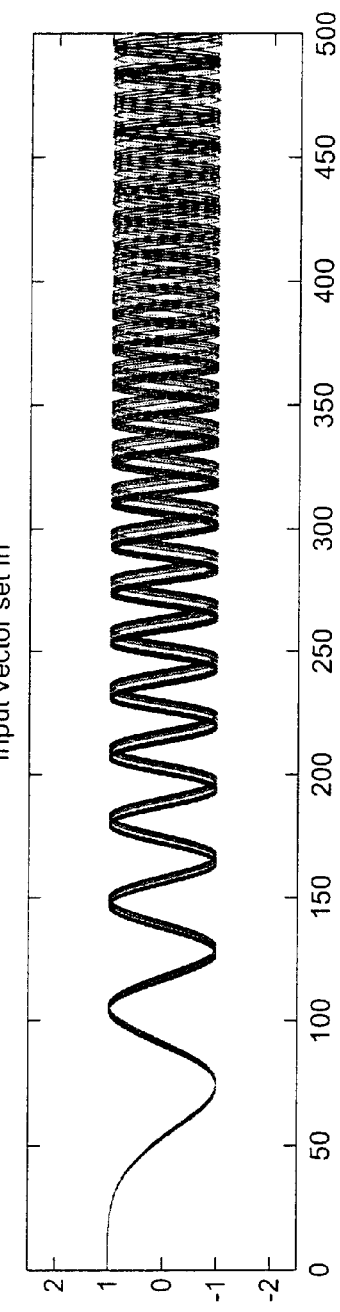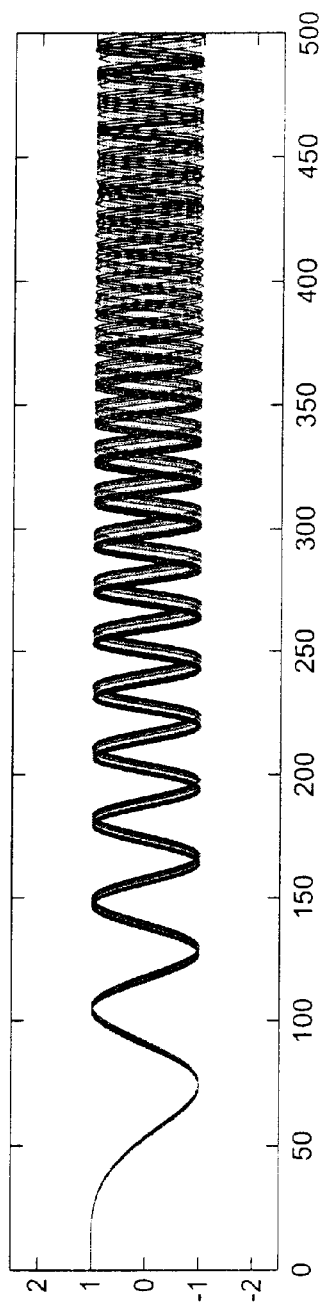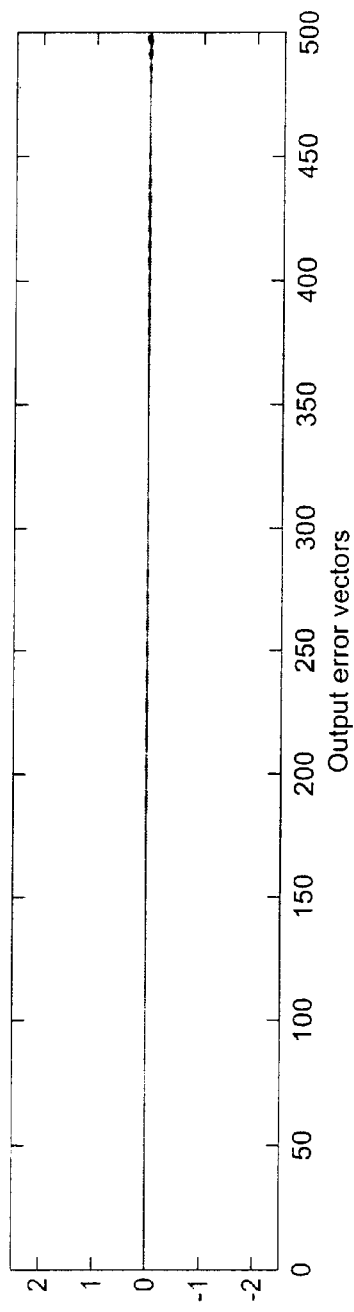
Fig. 15A
Fig. 15B
Fig. 15C

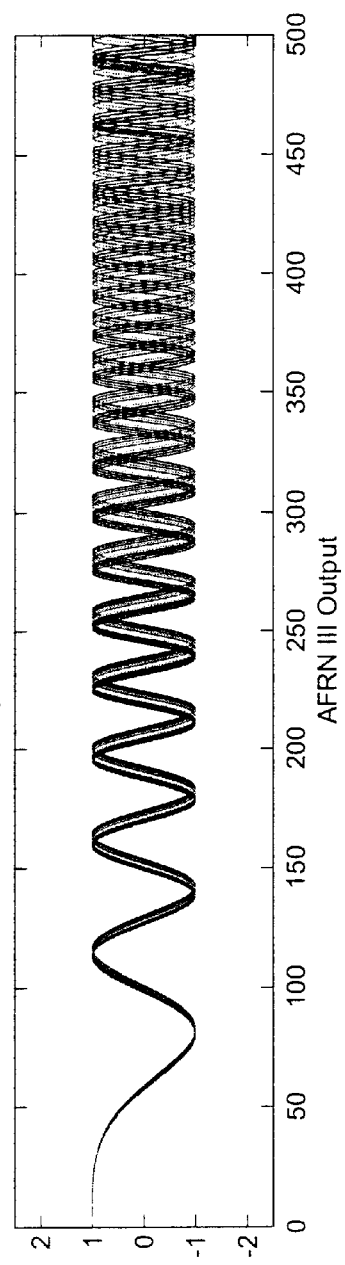
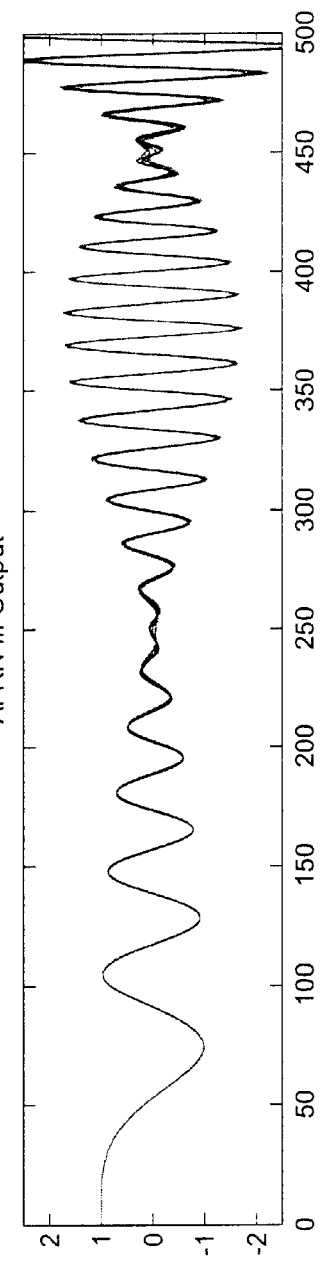
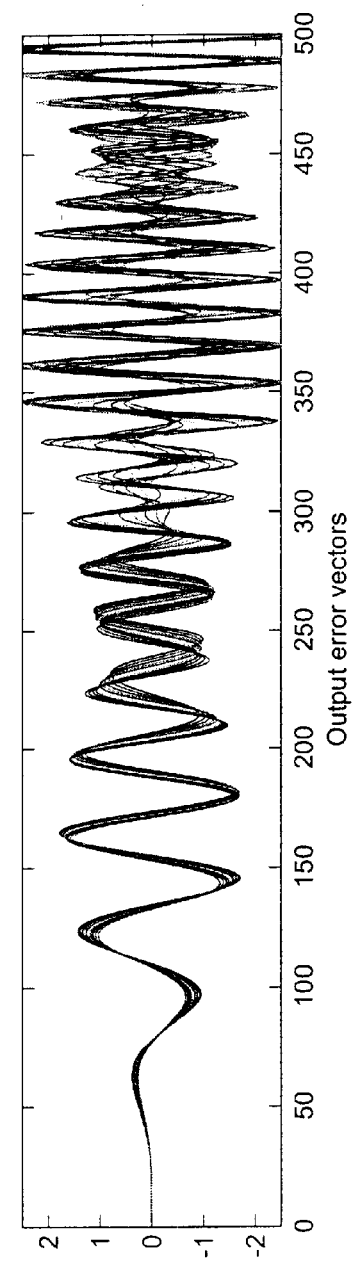
Fig. 17A
Fig. 17B
Fig. 17C

Reference vectors for Genotyping Classes I, II, and III

TRAINABLE ADAPTIVE FOCUSED REPLICATOR NETWORK FOR ANALYZING DATA

This application claims the benefit of U.S. Provisional Application No. 60/145,593, filed Jul. 26, 1999.

BACKGROUND OF THE INVENTION

A. Field of the Invention

The invention relates to replicator networks trainable to create a plurality of basis sets of basis vectors used to reproduce data for confirming identification of the data.

B. Description of the Related Art

Computers have long been programmed to perform specific functions and operations by means of sophisticated computer programming. However, in order to distinguish between data having similar features, human intervention is often required to make decisions about identification, categorization and/or separation of such data. There are no automated analysis systems that can perform sophisticated classification and analysis tasks at levels comparable to those of skilled humans.

A computer is, in essence, a number processing device. In other words, the basic vocabulary computers use to communicate and perform operations consists of numbers, mathematical relationships and mathematically expressed concepts. One portion of a computer's vocabulary includes basis vectors.

Basis vectors play an important role in multimedia and telecommunications. For instance, the images transmitted across the Internet and digital satellite television use powerful data compression technologies that encode images and sounds using predetermined sets of basis vectors to reduce the size of the transmitted data. After transmission, the encoded images and sounds are decoded by a receiver using the predetermined basis vector sets. By using predetermined basis vectors in the transmission and reception of images and sounds, the data can be stored and transmitted in a much more compact form. Typical data compression techniques using codecs (coders and decoders) using basis vector sets include:

JPEG & NWEG codecs—cosine waves form the basis vector sets,

Wavelet codecs—wavelets form the basis vector sets, and

Fractal codecs—fractals form the basis vector sets.

FIG. 1 is a grey-scale rendering of the basis vector set used in the JPEG compression technique. FIG. 1 shows an 8×8 array of basis vectors, each basis vector being a two-dimensional cosine wave having a different frequency and orientation. When an object image is to be transmitted over the Internet, the JPEG coder identifies a combination of these basis vectors that, when put together, define each section of the object image. Identification of the combination of basis vectors are transmitted over the Internet to a receiving computer. The receiving computer reconstructs the image using the basis vectors. In any given image, only a relatively small subset of basis vectors are needed in order to define the object image. The amount of data transmitted over the Internet is greatly reduced by transmitting identification of the basis vectors compared to transmitting a pixel by pixel rendering of the object image. The basis vectors in the JPEG technique are the limited vocabulary used by the computer to code and decode information. Similar basis vector sets are used in other types of data transmission, such as NV3 audio files. The smaller the vocabulary is, the more rapid the data transmission. In data compression, each data compression technique has its own predetermined, fixed set of basis vectors. These fixed sets of basis vectors are the vocabulary used by the compression technique. One of the primary purposes of the basis vector sets in data compression is to minimize the amount of data transmitted, and thereby speeding up data transmission. For instance, the JPEG data compression technique employs a 25 predetermined and fixed set of basis vectors. Cellular telephone data compression techniques have their own unique basis vectors suitable for compressing audio signals.

Traditionally basis vectors have been, in essence, a vocabulary used by computers to more efficiently compress and transmit data. Basis vectors may also be useful for other purposes, such as identification by computers of information. However, if an identification system is provided with a limited vocabulary, then only limited types of data are recognizable. For instance, identification systems have been developed to scan and recognize information in order to sort that information into categories. Such systems are preprogrammed to recognize a limited and usually very specific type of data. Bar code readers are a good example of such systems. The bar code reader is provided with a vocabulary that enables it to distinguish between the various width and spaces between bars correlating to a numeric value. However, such systems are fixed in that they can only recognize data pre-programmed into their computer systems. Once programmed, their function and vocabulary are fixed.

Another type of pre-programmed recognition system is in genome-based research and diagnostics. Specifically, sequencers have been developed for analyzing nucleic acid fragments, and for determining the nucleotide sequence of each fragment or the length of each fragment. Both Perkin-Ehner Corporation and Pharmacia Corporation currently manufacture and market such sequencer devices. In order to utilize such devices, a variety of different procedures are used to break the nucleic acid fragment into a variety of smaller 20 portions. These procedures include use of various dyes that label predetermined nucleic acids within the fragment at specific locations in the fragment. Next, the fragments are subjected to gel electrophoresis, subjected to laser light by one of the above mentioned devices and the color and intensity of light emitted by the dyes is measured. The color and intensity of light is then used to construct an electropherograxn of the fragment under analysis.

The color and intensity of light measured by a device indicates the presence of a dye further indicating the location of the corresponding nucleic acid within the sequence. Such sequencers include scanners that detect fluorescence from several illuminated dyes. For instance, there are dyes that are used to identify the A, G, C and T nucleotide extension reactions. Each dye emits light at a different wavelength when excited by laser light. Thus, all four colors and therefore all four reactions can be detected and distinguished in a single gel lane.

Specific software is currently used with the above mentioned sequencer devices to process the scanned electropherograms. The software is pre-programmed to recognize the light pattern emitted by the pre-designated dyes. The vocabulary of the software is limited to enable the system to recognize the specific patterns. Even with pre-designated patterns and logical results, such systems stiff require human intervention for proper identification of the nucleic acid sequences under study. Such systems yield significant productivity enhancements over manual methods, but further improvements are desirable.

There exists a need for a reliable, expandable and flexible means for identifying and classifying data. In particular, there is a need for more flexible identification systems that can be easily enhanced for identification of new and differing types of data.

SUMMARY OF THE INVENTION

One object of the invention is to provide a simple and reliable system for identifying data.

Another object of the present invention is to provide a data classification system with more flexible means for identifying and classifying data.

The invention relates to a method and apparatus that is trainable to identify data. The invention includes inputting several previously identified data sets into a computer and creating within the computer a plurality of unique basis vector sets. Each basis vector set includes a plurality of basis vectors in one to one correspondence with each of the identified data sets. For each data set, a comparison set of data is created using only the created basis vector sets. A comparison is made between each of the previously identified data sets and corresponding-comparison data set thereby generating error signals for each comparison. A determination is made to determine the acceptability of the error. Once the error is determined to be acceptable, the training phase is completed.

Once the basis vector sets have been established as being acceptable, new unidentified data is inputted into the computer. The new data is replicated separately using each individual basis vector set constructed during the training phase. For each basis vector set, a comparison is made between the inputted data and the replicated data. The inputted data is accurately replicated only by one of the basis vector sets, thereby providing a means for classifying the now identified data.

The foregoing and other objects, features, aspects and advantages of the present invention will become more apparent from the following detailed description, when taken in conjunction with the accompanying drawings.

BRIEF DESCRIPTION OF THE DRAWINGS

FIGS. 10A, 10B, and 10C show a novel (unknown) input having features similar to reference set I, a replica of the novel input generated by trained AFRN I and output error;

FIGS. 11D, 11E and 11F showing input reference vectors III (input into AFRN I), the output from AFRN I attempting to replicate input reference vectors III and the output error demonstrating the inability of AFRN I to replicate reference vectors III;

FIGS. 15A, 15B and 15C show input of reference set III, replicas of reference set III generated by AFRN III during the training phase and an output error generated by comparing reference set III and the replicas created by AFRN III;

FIGS. 17A, 17B and 17C showing input reference vectors I (input into trained AFRN III), the output from AFRN III attempting to replicate input reference vectors I and the output error demonstrating the inability of AFRN III to replicate reference vectors I;

DETAILED DESCRIPTION OF THE INVENTION

Figure 2:
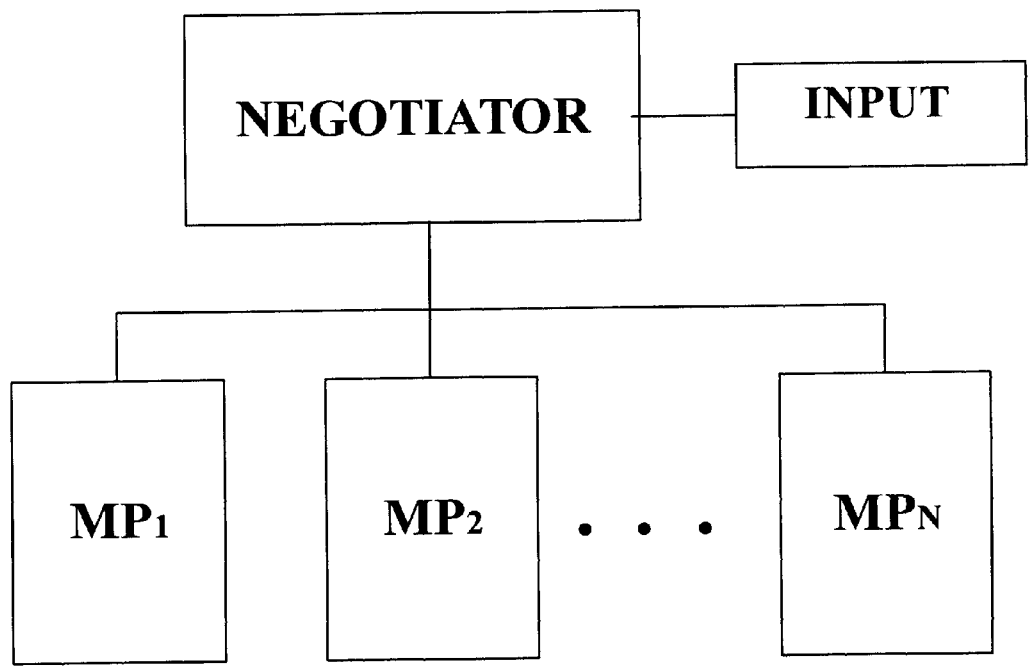
FIG. 2 is a schematic representation of a plurality of computers in a network in accordance with one embodiment of the present invention.

The present invention relates to adaptive focused replicator networks (AFRNS) that are trainable in order to distinguish between a plurality of differing data sets, thereby providing a means for separating and classifying such data. On a small scale, AFRNs may be utilized in a single computer performing the techniques described below, or may be utilized in a system having a plurality of computers connected to one another, as shown schematically in FIG. 2 where a plurality of microprocessors MP1, MP2 through MPN are linked together via a Negotiator. Such connected computers may include a cluster network, a SMP system (Symmetric Multi-Processor system), Asymmetric Multi-Processor systems or a dedicated firmware and hardware system such as GRAPE (Gravity Pipe), which is used to greatly accelerate calculations in computational astrophysics. It should be understood that the plurality of microprocessors may be linked to one another via the negotiator or at the chip level or in clusters.

AFRNs include a plurality of array elements, each array element being trainable to recognize and classify one specific type of data, as is described in greater detail below. One group of array elements may be effected in single computer or may be divided in the group of microprocessors in FIG. 2, depending upon the size and requisite speed of the data classification system of the present invention.

The present invention works as follows. A custom basis vector set made up of one or more basis vectors is generated from a reference set of input data. Then, new data is inputted and the custom basis vectors are used to reconstruct (replicate) the input data. The custom set of AFRN basis vectors permits accurate reconstruction of closely similar data but prevents faithful reconstruction of data that differ from the reference set in one or more important details.

AFRNs use basis vector sets but not in the manner typically associated with data compression. In the present invention, each array element in an AFRN creates its own unique combination of basis vectors creating a basis vector set that is later used to identify and thereby classify unknown inputted data. In the present invention, basis vector sets are constructed in order to maximize a computer system's ability to recognize and classify the type of data inputted. There is no limit in the present invention to the number of basis vectors that may be selected in order to define the various basis vector sets. However, as discussed further below, each array element of the present invention is trained to have its own unique individual basis vector set having a limited group of basis vectors used for replicate a specific type or group of data.

In accordance with one embodiment of the present invention, a method for classifying types of data in a data set includes two fundamental phases: a learning phase; I 0 and a replicating phase.

Figure 3:
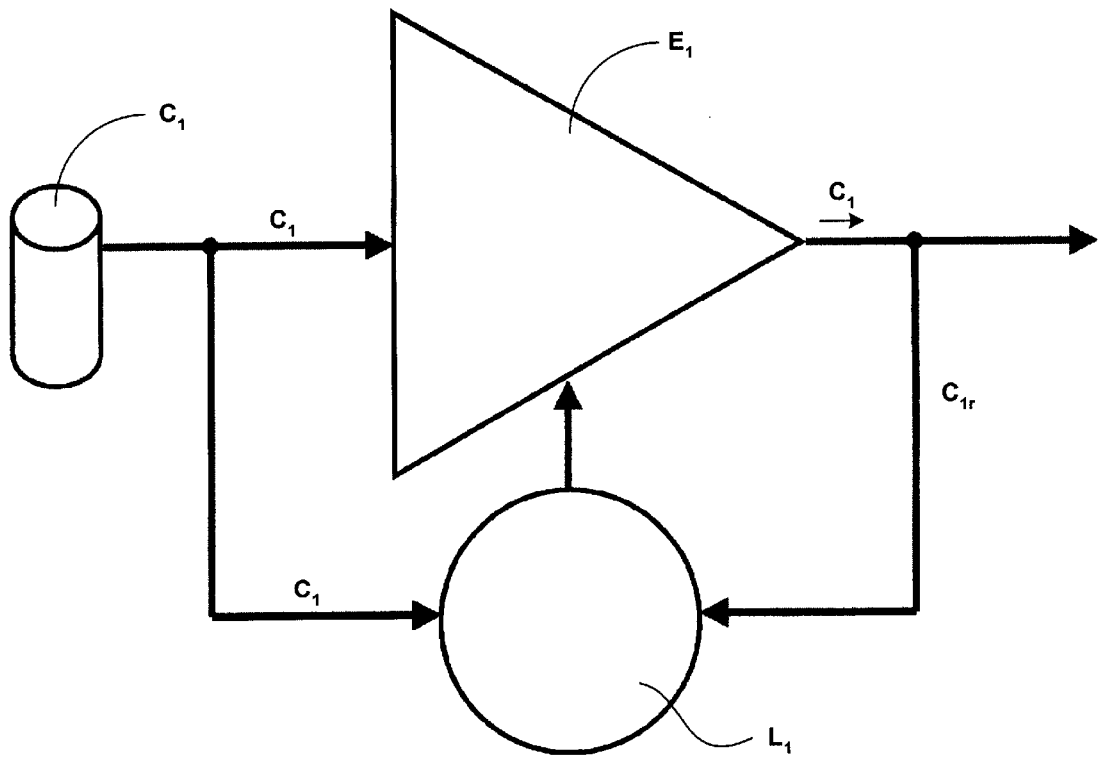
FIG. 3 is a graphical representation of an adaptive focused replicator network in a training phase.

In the learning phase, previously categorized sets of data $C_1$ through $C_N$ are inputted into a computer or network of computers. In order to explain the training phase, only one data set is considered in FIG. 3. One of the sets of data, for instance, data set $C_1$, is inputted into the AFRN array element $E_1$, as shown in FIG. 3. The array element $E_1$ then generates a basis vector set having a plurality of basis vectors based upon data set C1. The basis vectors are determined in any of a variety of analytical or empirical ways. For instance, the data elements in the data set C, are solvable as linear equations to determine the basis vectors.

Figure 1:
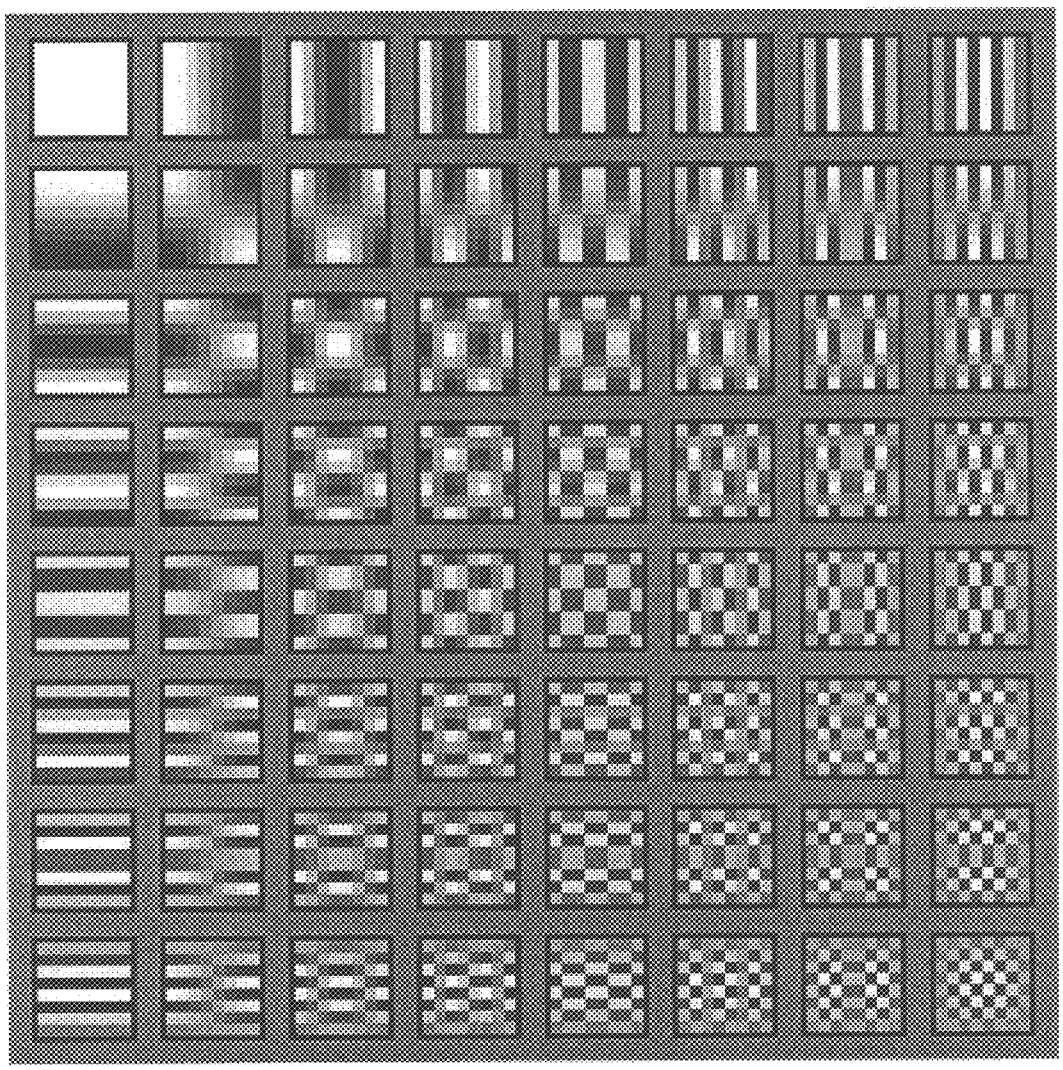
FIG. 1 is a graphical representation of a gray scale JEPG palette used by computers to compress image data.

The basis vectors in the basis vector set may be any of a combination of basis vector types such as: chirplets, wavelet, Fourier based functions, Fractal and/or radial basis functions (BFs), basis functions generated using MLP (multi-layer perceptrons) or other basis vectors determined by the computer and assigned to the array element $E_1$. For instance, if the data set $C_1$ includes audio signals, then the basis vectors will likely be solved by the computer and made part of element E1 as a plurality of Fourier based functions. If the data set $C_1$, includes images, then the basis vectors determined by the element $E_1$ will likely, but not necessarily, be two dimensional cosine related basis vectors similar to the above described basis vectors used in the JPEG compression technique (FIG. 1).

As indicated in FIG. 3, as a part of the training phase, the array element $E_1$ constructs a replicate data set $C_1$. The replicate data set $C_1$ is then compared with the elements of original data set $C_1$, and an error value is generated, at evaluation point $L_1$. The error is evaluated to determine whether the error is acceptable or unacceptable. If acceptable, then the array element $E_1$ is trained. If unacceptable, then the generation or refinement of basis vectors continues.

Figure 4:
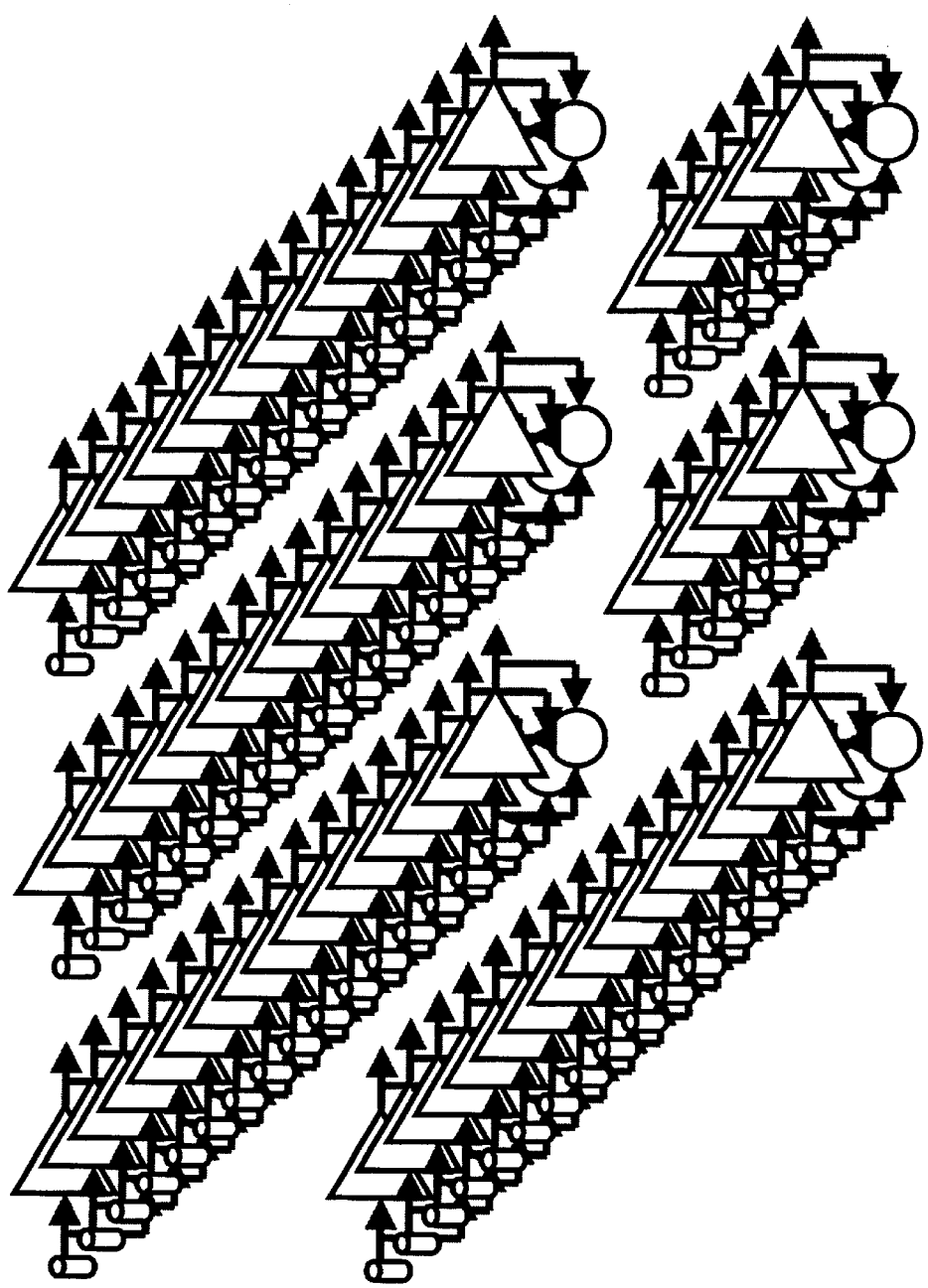
FIG. 4 is a graphical representation of a plurality of adaptive focused replicator networks in the training phase.

Similarly, although not shown in FIG. 3, an array element $E_2$ generates a basis vector set based upon a data set $C_2$, and so on until array element $E_N$ has generated a basis vector set for data set $C_N$. A plurality of AFRN arrays, each having a plurality of array elements are depicted in FIG. 4, each array element trained in a manner described above with respect to FIG. 3, but with each array element trained to replicate a differing data set. As is indicated in FIG. 4, the plurality of AFRN arrays may be grouped by data types. For instance, one AFRN array may have array elements that are trained to replicate and classify one data class having multiple subclasses of data, another AFRN array may have array elements trained to replicate and classify another data class having a only a few subclasses of data. Specifically, in an optical recognition application of the AFRN arrays of the present invention, one AFRN array in FIG. 4 may be for replicating and classifying different hues of blue, another AFRN array may be trained for replicating and classifying different hues of red, and so on.

Figure 5:
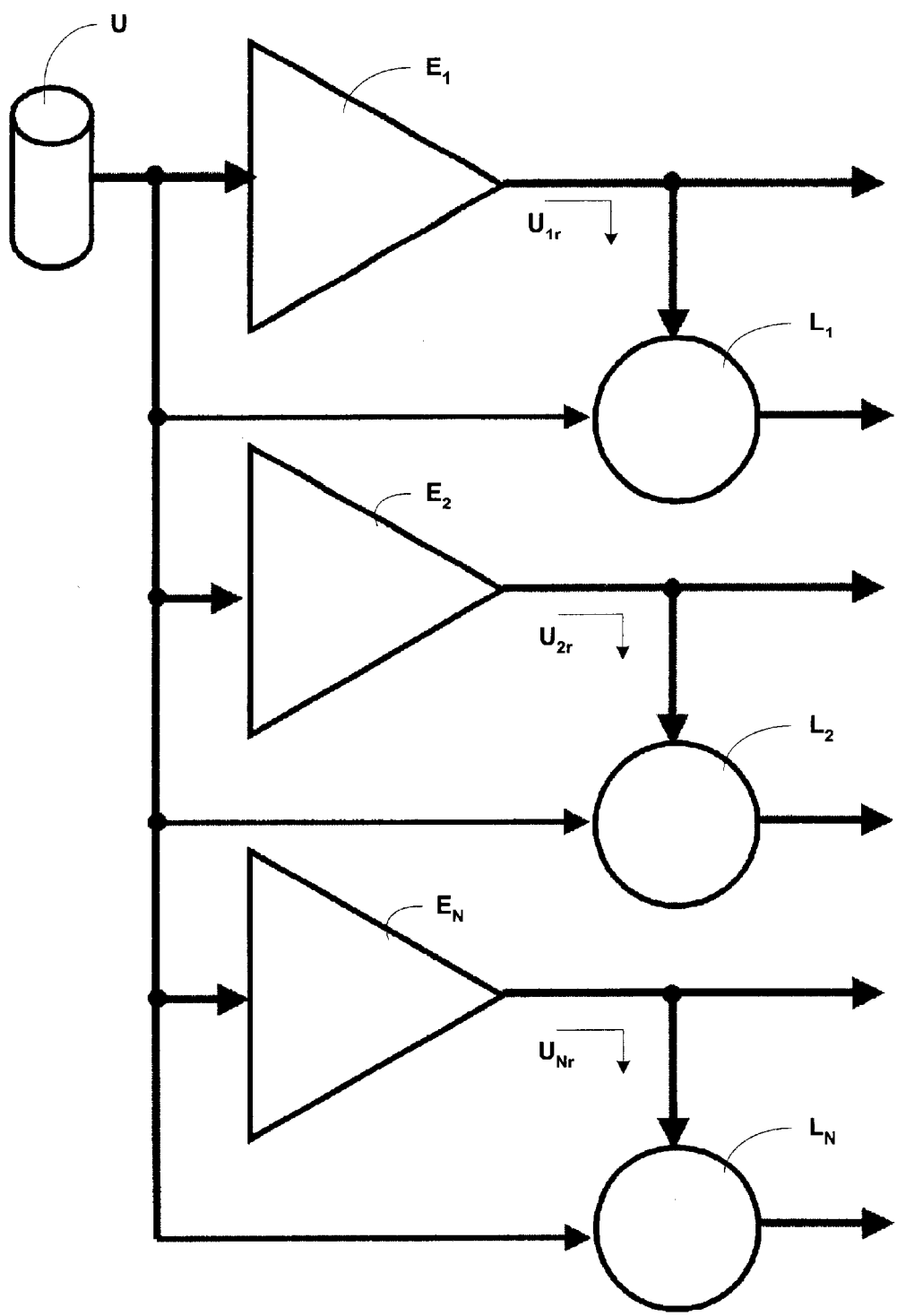
FIG. 5 is a graphical representation of an adaptive focused replicator network in a replicating phase.

Once the complete array of elements has been trained, it is now possible to classify new data by passing the data through all of the array elements. In other words, each data element of an unknown data set is considered by each and every array element in one AFRN array. As indicated in FIG. 5, all the data in unknown data set U is inputted into the AFRN array elements $E_1$ through $E_N$. The array element $E_1$ then attempts to generate a replica of each and every data element of unknown data set U. At the evaluation point $L_1$, a comparison is made between the replica $U_{r1}$ of data element U and the data element U. Since array element $E_1$ includes basis vectors capable of effectively replicating data elements of only data set $C_1$, replication of any data not of data set $C_1$, will not be successful. Therefore, the comparison between the replicated data element and the original data element yield either acceptable or unacceptable results. If the results are acceptable, then the unknown data element is categorized as being of the data set $C_1$. If the results are not acceptable, then the unknown data element is not of the data set C, and is not categorized by array element $E_1$.

Figure 6:
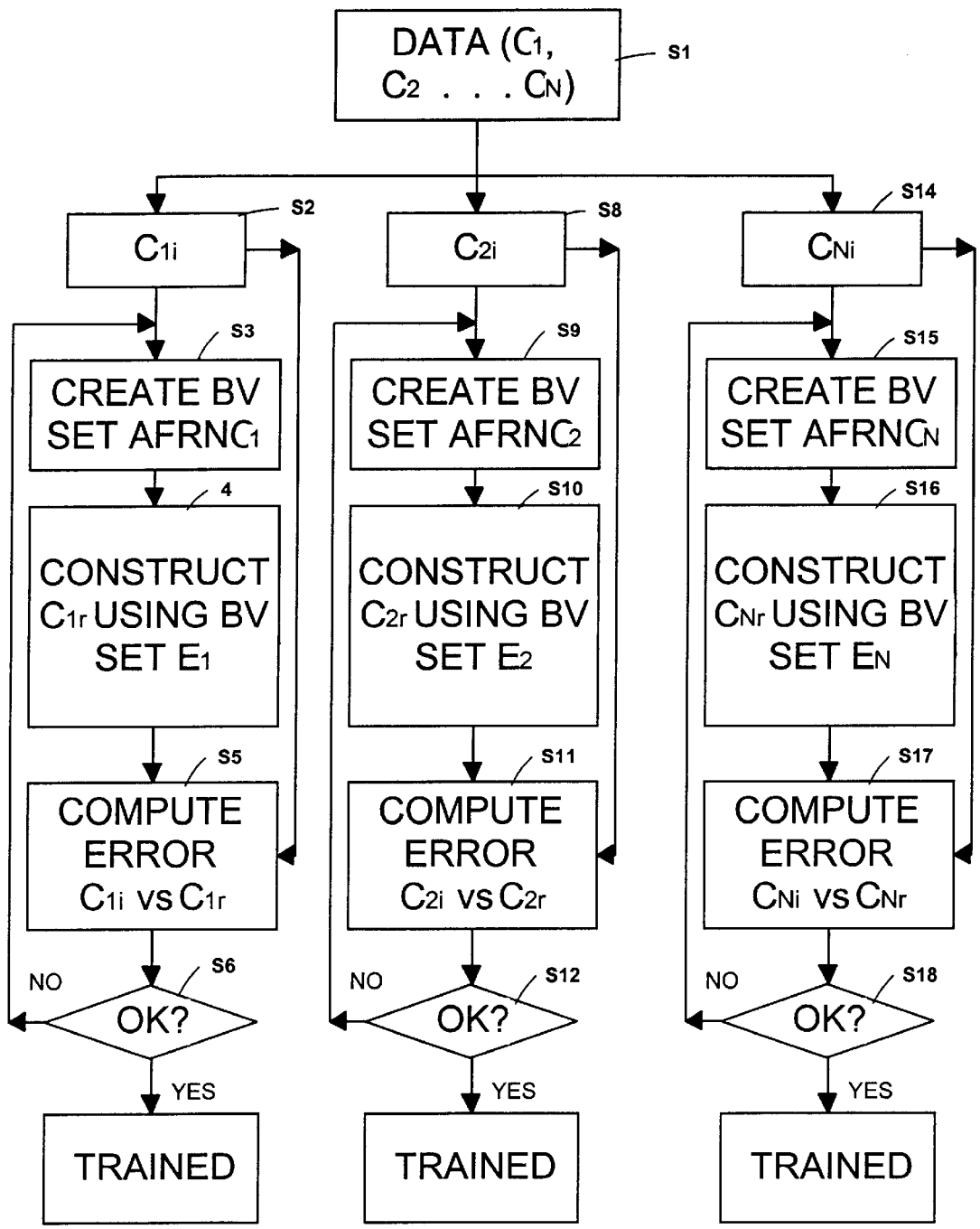
FIG. 6 is a flowchart showing various steps of the training phase and replicating phase of the adaptive focused replicator network.

Referring now to FIG. 6, operational steps are depicted as performed by a computer or network of computers in accordance with the present invention. Specifically, at step S1, pre-sorted and categorized data sets $C_1$ through $C_N$ are inputted into the computer. However, at step S2, data set $C_1$, is sent only to a first array element $E_1$ (not shown in FIG. 6), at step S8 data set $C_2$ is sent only to a second array element $E_2$ (not shown in FIG. 6), and so on until a final iteration begins at step S14 where a final data set $C_N$ is sent to a final array element $E_N$ (not shown in FIG. 6).

It should be appreciated that the counter N used throughout the description of the invention, for instance in and $E_N$, is any positive integer ranging from 1 to about $10^6$. N could be greater than $10^6$, depending upon computer capability and complexity, and the requirements of the data classification.

At step S3 in FIG. 6, the first array element $E_1$ generates a first basis vector set $AFRNC_1$, based upon the data elements of categorized data set $C_1$. The first basis vector set $AFRNC_1$, consists of basis vectors generated by the computer's mathematical analysis of each of the data elements of categorized data set $C_1$. In other words, the first basis vector set $AFRNC_1$, defines the replication vocabulary of first array element $E_1$. At step S4, data replicas $C_{1r}$, of each data element of the data set $C_1$, are constructed using the first basis vector set $AFRNC_1$. At step S5 a comparison is made between each of the replicas $C_1$, and corresponding data elements of the data set $C_1$, thereby producing an error value for each comparison. At step S6 a determination is made whether or not the error values are within an acceptable range. If the error values are within an acceptable range, then the vocabulary of basis vectors in the first basis vector set $AFRNC_1$, is acceptable and the first array element $E_1$ is trained. If the error values are not within an acceptable range, then the process repeats from step S3 until an appropriate basis vector set can be determined.

Similarly, at step S9, the second array element $E_1$ generates a second basis vector set $AFRNC_2$ based upon the data elements of categorized data set $C_2$. The second basis vector set $AFRNC_2$ consists of basis vectors generated by the computer's mathematical analysis of each of the data elements of categorized data set $C_2$. At step S10, data replicas $C_{2r}$, of each data element of the data set $C_2$ are constructed using the second basis vector set $AFRNC_2$. At step S11 a comparison is made between each of the replicas $C_2$, and corresponding data elements of the data set $C_2$ thereby producing an error value for each comparison. At step S12 a determination is made whether or not the error values are within an acceptable range. If the error values are within an acceptable range, then the second basis vector set $AFRNC_2$ is acceptable and the second array element $E_2$ is trained. If the error values are not within an acceptable range, then the process repeats from step S9 until an appropriate basis vector set can be generated.

The training process continues through the Nth iteration. Specifically, the Nth iterations is depicted beginning at step S15, where the Nth array element $E_N$ generates an Nth basis vector set $AFRNC_N$ based upon the data elements of categorized data set $C_N$. The Nth basis vector set $AFRNC_N$ consists of basis vectors generated by the computer's mathematical analysis of each of the data elements of categorized data set $C_N$. At step S16, data replicas $C_{Nr}$ of each data element of the data set $C_N$ are constructed using the Nth basis vector set $AFRNC_N$. At step S17 a comparison is made between each of the replicas $C_N$, and corresponding data elements of the data set $C_N$ thereby producing an error value for each comparison. At step S18 a determination is made whether or not the error values are within acceptable range. If the error values are within an acceptable range, then the Nth basis vector set $AFRNC_N$ is acceptable and the Nth array element $E_N$ is trained. If the error values are not within an acceptable range, then the process repeats from step S15 until an appropriate basis vector set can be generated.

Once the AFRNs are trained, then the system is ready to identify new data by categorizing it in the previously identified categories.

Figure 7:
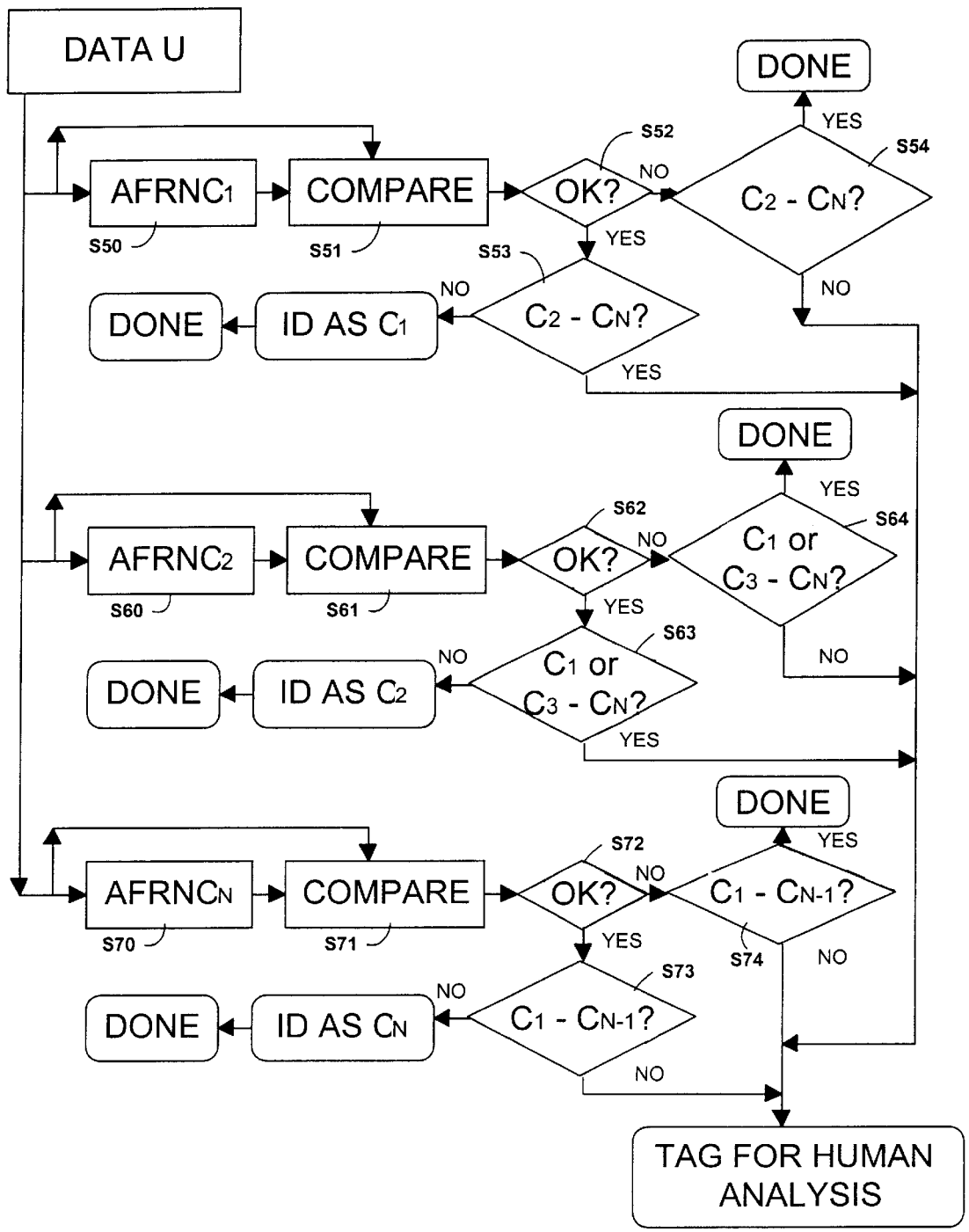
FIG. 7 is flowchart showing various steps of an identification phase of the adaptive focused replicator network.

Specifically, as shown in FIG. 7, an unknown data element U is inputted into the computer or computer network for categorization. N number of data paths are depicted in FIG. 7 with the data U being inputted into each of the data paths for analysis by $AFRNC_1$, $AFRNC_2$, and so on until the Nth iteration of analysis by $AFRNC_N$, the following description goes through operations in one data path at a time. However, it should be understood that computers operate at such an accelerated rate, that all N data paths proceed almost simultaneously.

At step S50, data replica $U_{r1}$, is constructed using the first basis vector set $AFRNC_1$, in an attempt to reproduce the data U. At step S51 a comparison is made between the replica U, and the data U thereby producing an error value. At step S52 a determination is made, specifically, if the error value is within an acceptable range, then operation moves to step S53. If the error value is not acceptable, operation moves to step S54. At step S53, a determination is made whether or not the data U has been categorized in another data path as falling within any one of data sets $C_2$ through $C_N$. If the determination at step S53 is no, then the data U is identified and categorized as falling within data set $C_1$, and the operation with respect to classification of the data U is done. If the determination at step S53 is yes, specifically, one of the other AFRN array elements identified data U as being of a data set other than $C_1$, then data U is tagged for human analysis. In other words, the system has a problem identifying data U. Returning to step S52, if the error is not acceptable, then the data U is not of the data set $C_1$, and another determination must be made at step S54. At step S54 a determination is made whether the data U has been identified as being in one and only one of the other data categories, such as data $C_2$ through $C_N$. It should be understood that at step S54 identification of the data U must only be confirmable in one and only one data category. If the data U is categorized in more than one data category, for instance more that one of data sets $C_2$ through $C_N$, then data U is not properly categorized by the system and must be tagged for human analysis.

Similarly, at step S60, data replica $U_{r2}$ is constructed using the first basis vector set $AFRNC_2$ in an attempt to reproduce the data U. At step S61 a comparison is made between the replica $U_{r2}$ and the data U thereby producing an error value. At step S62 a determination is made, specifically, if the error value is within an acceptable range, then operation moves to step S63. If the error value is not acceptable, operation moves to step S64. At step S63, a determination is made whether or not the data U has been categorized in another data path as falling within any one of data sets $C_1$, $C_3$ through $C_N$. If the determination at step S63 is no, then the data U is identified and categorized as falling within data set C2 and the operation is done. If the determination at step S63 is yes, specifically, one of the other AFRN array elements identified data U as being of a data set other than $C_2$, then data U is tagged for human analysis. Returning to step S62, if the error is not acceptable, another determination is made at step S64. At step S64 a determination is made whether the data U has been identified as being in one and only one of the other data categories, such as data $C_1$, or $C_3$ through $C_N$. It should be understood that at step S64 identification of the data U must only be confirmable in one and only one data category. If the data U is categorized in more than one category, for instance more that one of data sets $C_1$, $C_3$ through $C_N$, then data U is not properly categorized by the system and must be tagged for human analysis.

The operations are similar for all of the data paths. For the Nth iteration, at step S70, data replica $U_{rN}$ is constructed using the first basis vector set $AFRNC_N$ in an attempt to reproduce the data U. At step S71 a comparison is made between the replica $U_{rN}$ and the data U thereby producing an error value. At step S72 a determination is made. If the error value is within an acceptable range, then operation moves to step S73. If the error value is not acceptable, operation moves to step S74. At step S73, a determination is made whether or not the data U has been categorized in another data path as &fling within any one of data sets $C_1$, through $C_{N-1}$. If the determination at step S73 is no, then the data U is identified and categorized as falling within data set $C_N$ and the operation is done. If the determination at step S73 is yes, specifically, one of the other AFRN array elements identified data U as being of a data set other than $C_N$, then data U is tagged for human analysis. Returning to step S72, if the error is not acceptable, another determination is made at step S74. At step S74 a determination is made whether the data U has been identified as being in one and only one of the other data categories, such as data $C_1$ through $C_{N-1}$. It should be understood that at step S74 identification of the data U must only be confirmable in one and only one data category. If the data U is categorized in more than one category, for instance more that one of data sets $C_1$, through $C_{N-1}$, then data U is not properly categorized by the system and must be tagged for human analysis. It should be understood that the data sets $C_1$, through $C_N$ used in the description above of the invention, may be similar types of data or may be discrete groups of data with little or no relationship to one another. However, to demonstrate the power of the present invention, the inventor has conducted several experiments where the data sets $C_1$, through $C_N$ were all of a similar nature.

EXAMPLE ONE

Chirps

In an example prepared by the inventor, an array of AFRNs was constructed using chirps. Chirps are complex exponential waves that vary with time. Chirps are important in a variety of applications such as radar, laser, sonar and devices and in telecommunication links. In the training phase, three separate AFRN array elements were prepared, AFRN I, AFRN II and AFRN III, as is described in greater detail below.

Figures 8A, 8B, 8C:
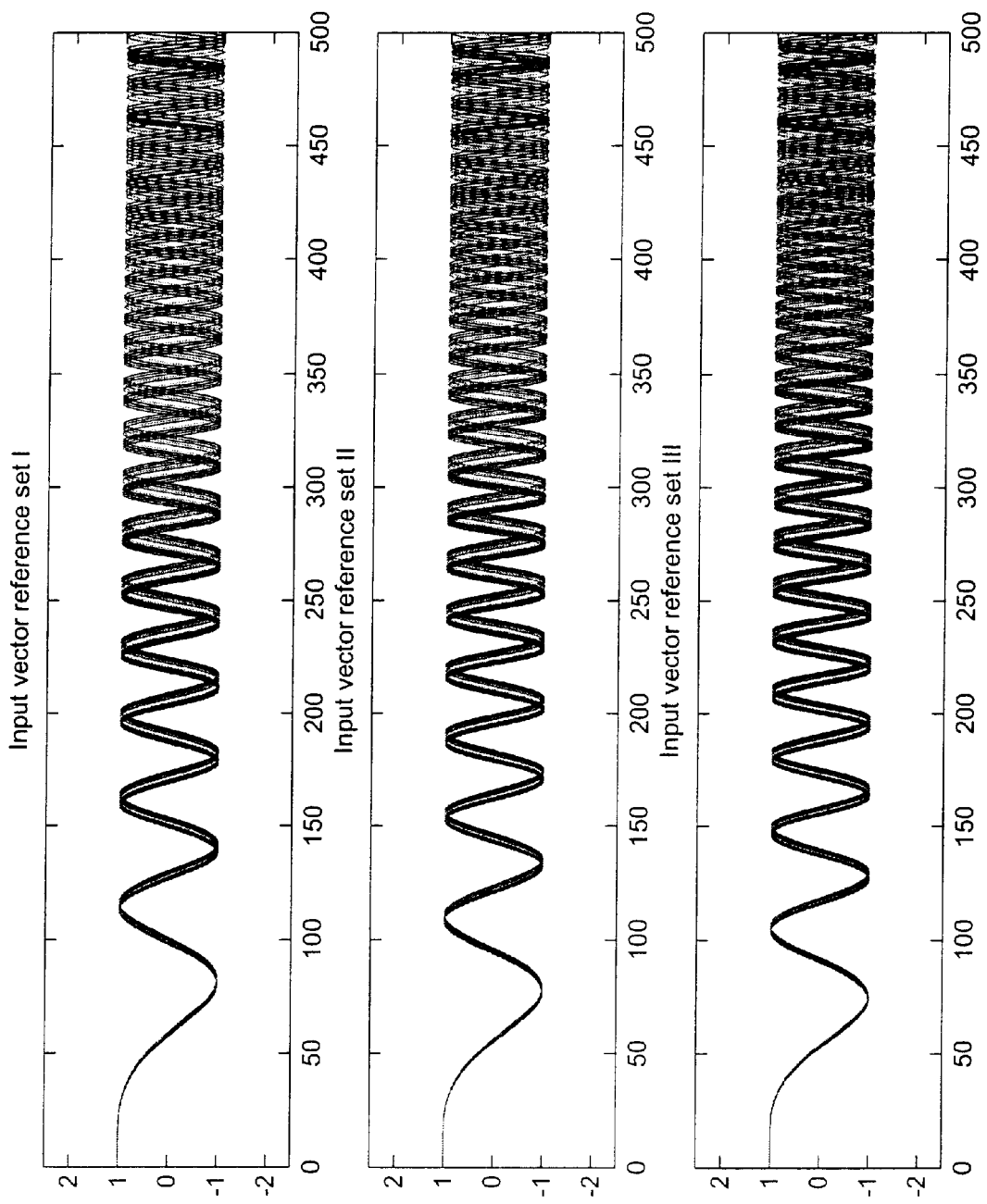
FIGS. 8A, 8B and 8C show chirps input references sets I, II and III, demonstrating first example of the present invention.

Chirps were used in this experiment because, as is observed by visual inspection of FIGS. 8A, 8B and 8C, they appear to be very similar. Human intervention is not likely to detect the differences between such three similar data sets. Chirps are also complex signals that can be generated with mathematical precision. The chirps are also 'data-dense' because they are mathematically complex. Compared to real world applications of the present invention, the following example using Chirps is significantly more complex.

Each chirp in FIGS. 8A, 8B and 8C is made up of 500-element vectors, each individual vector defined by a point located at a point that can be identified visually by a pair of X and Y coordinates. Reference Set I shown in FIG. 8A, has 10 chirps (or waves) altogether, the chirps in reference set I being distinguished from one another by a very slight off-set in frequency. Reference Set II shown in FIG. 8B also has 10 chirps altogether, the chirps distinguished from one another by a very slight offset in frequency. Reference Set III shown in FIG. 8C has 10 chirps as well, the chirps distinguished from one another by a very slight offset in frequency.

Three sets of known chirp sets used to demonstrate the present invention are depicted in FIGS. 8A, 8B and 8C and are labeled Input Reference Set I, Input Reference Set II and Input Reference Set III, respectively. Visually, the three chirps in FIGS. 8A, 8B and 8C look similar, but vary in frequency over time. Specifically, each chirp has its own unique frequency profile as can be seen by observing the location of the curves at data points 200 and 300 along the X-axis in FIGS. 8A, 8B and 8C.

AFRN I, AFRN II and AFRN III were created, one AFRN for each of the three sets of chirps. Each AFRN trained to replicate one of the three reference sets. During the training phase, AFRN I was given the ten chirp vectors in Input Reference Set I (FIG. 8A), AFRN II was given the ten chirp vectors in Input Reference Set II (FIG. 8B) and AFRN III was given the ten chirp vectors in Input Reference Set III (FIG. 8C).

Figure 18A:
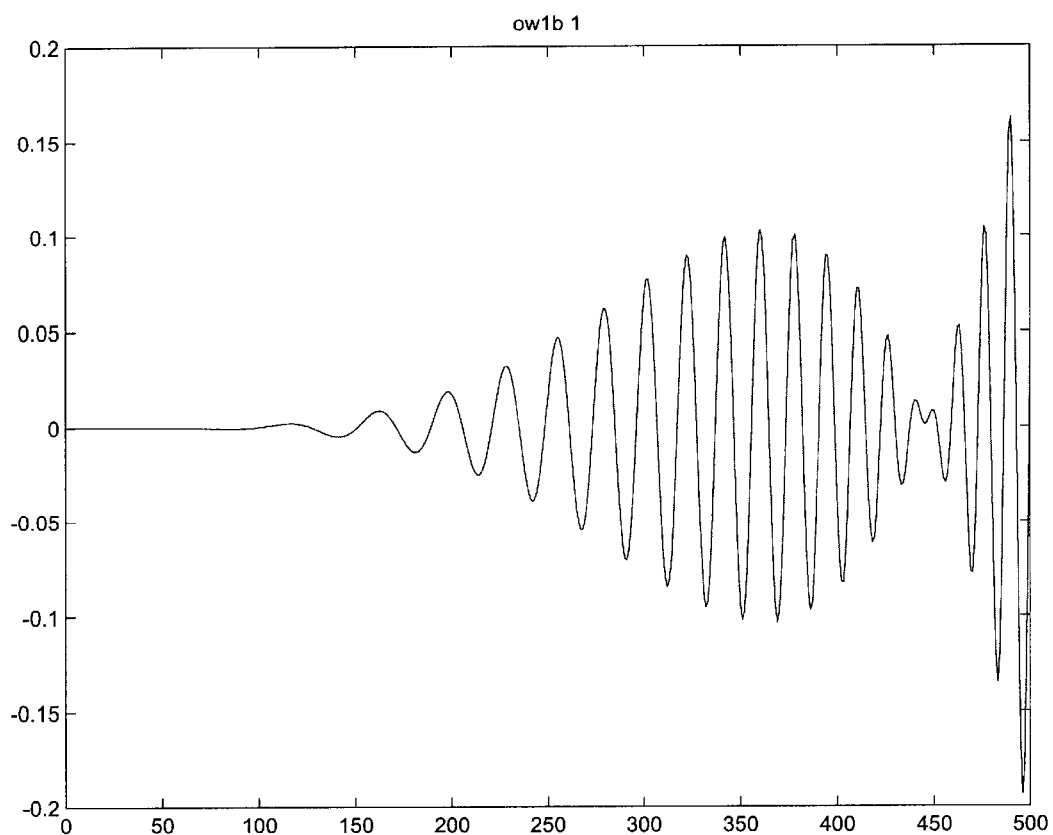
FIGS. 18A, 18B, 18C, 18D and 18E show basis vectors generated by AFRN I during the training phase and used to replicate inputted data.
Figure 18B:
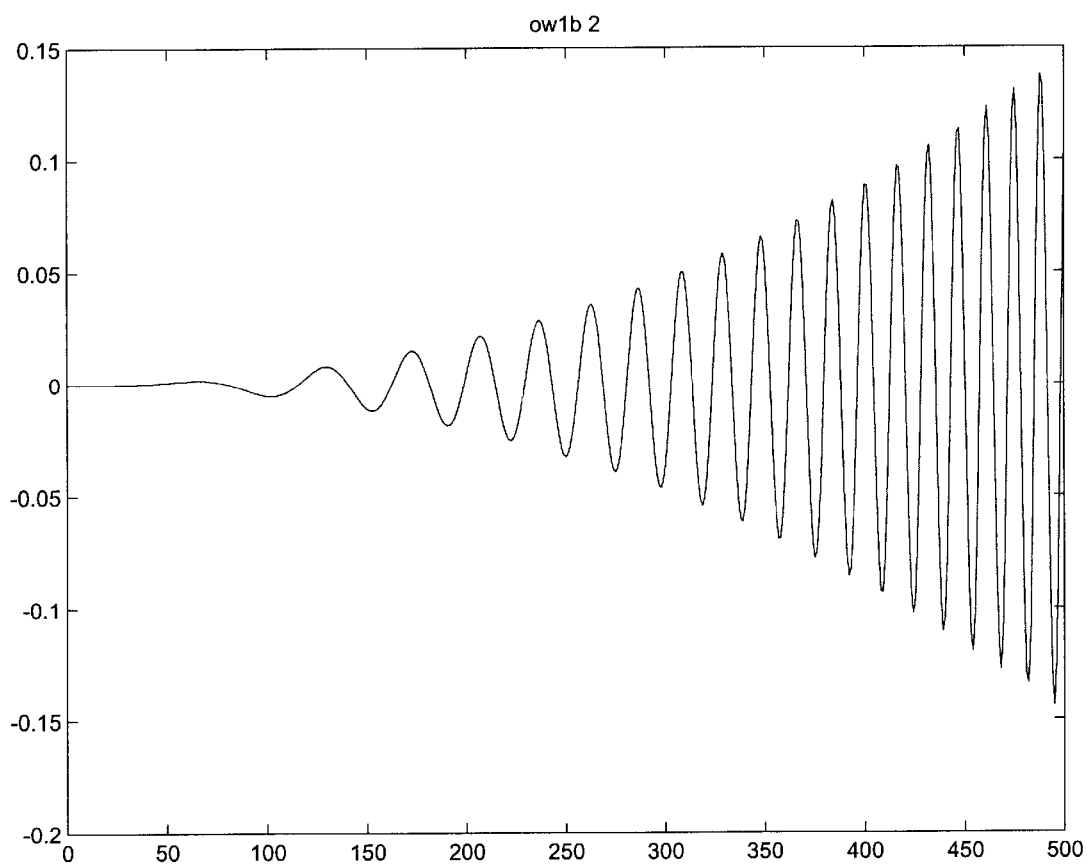
Figure 18C:
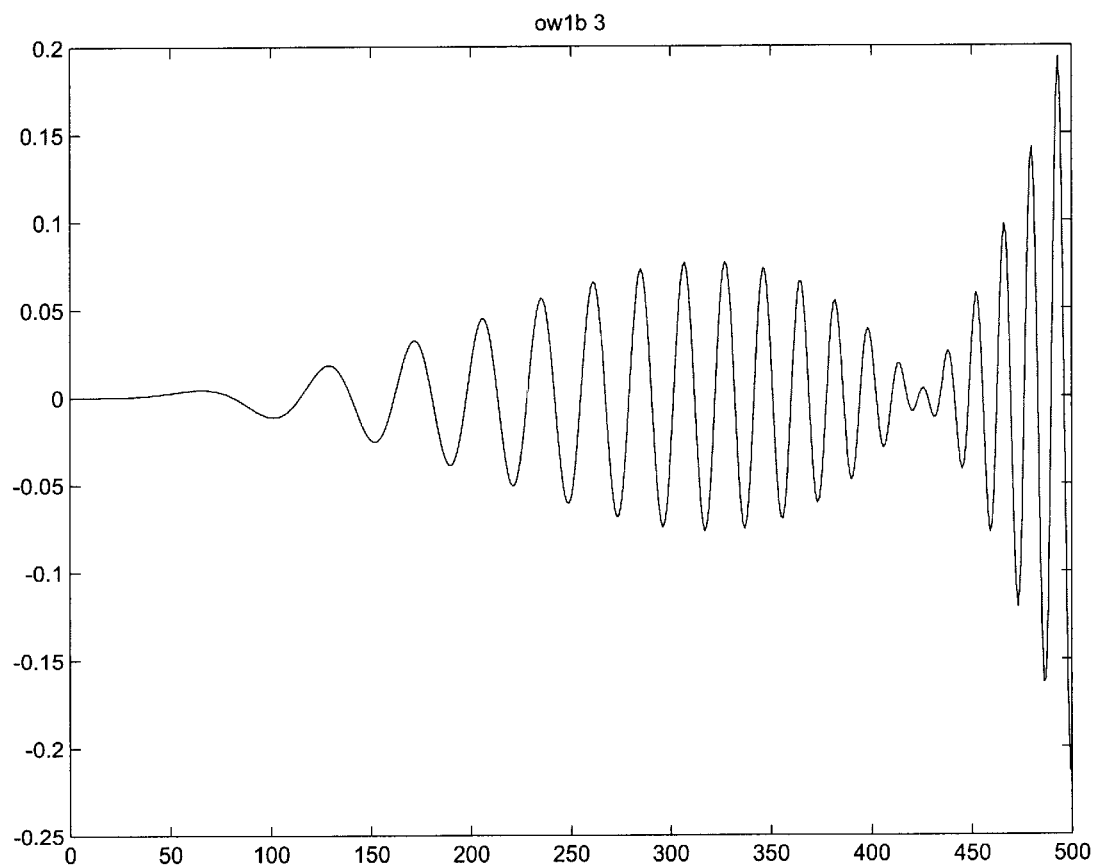
Figure 18D:
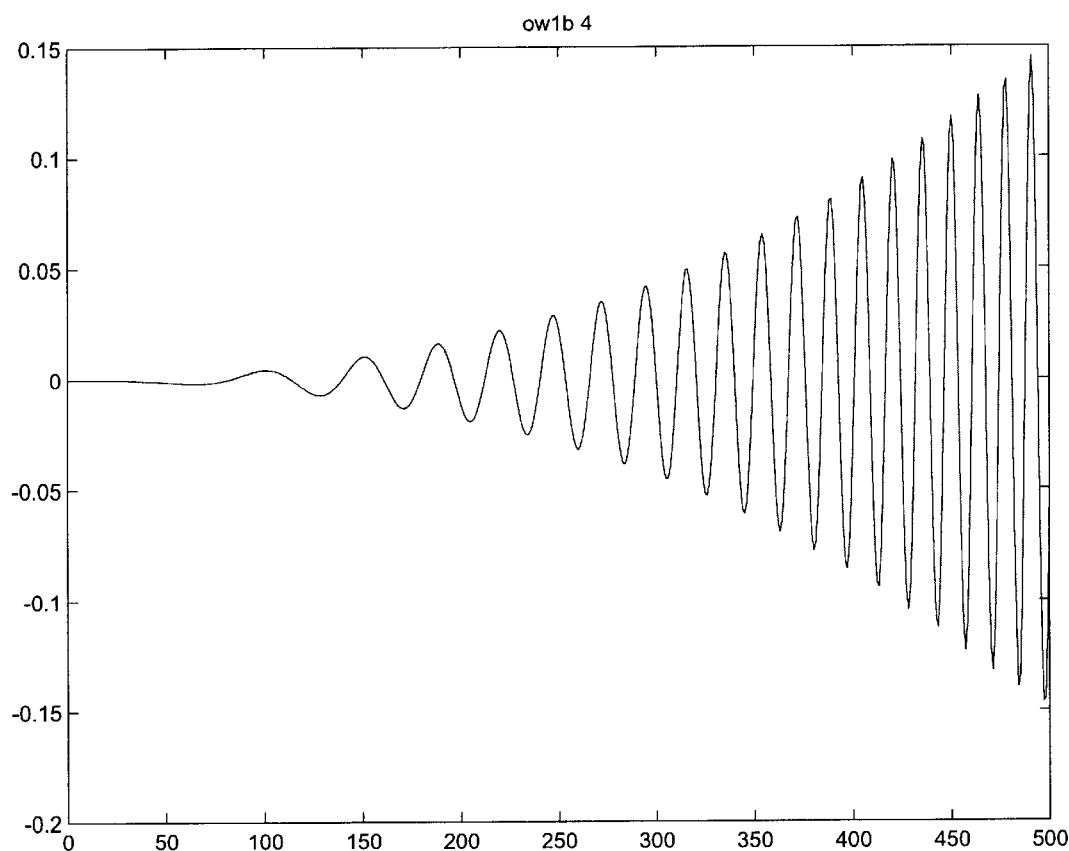
Figure 18E:
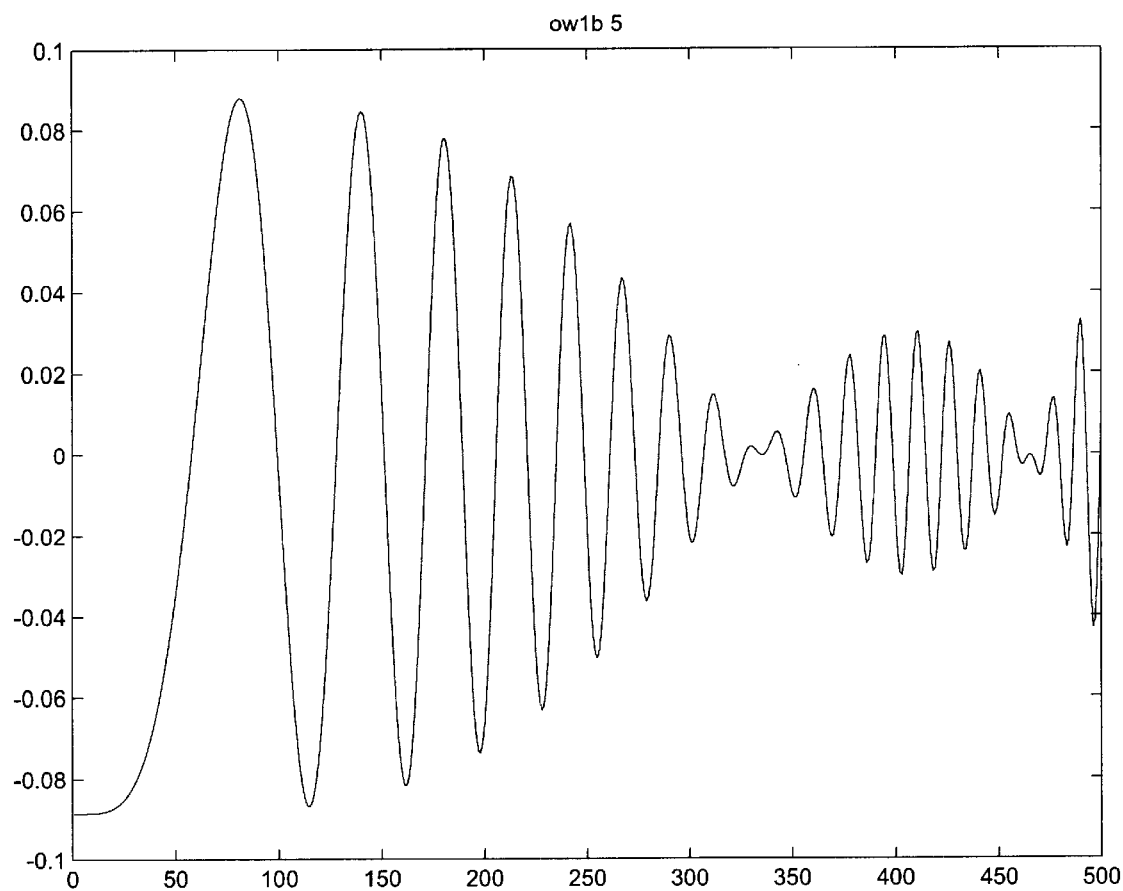
Figure 18F:
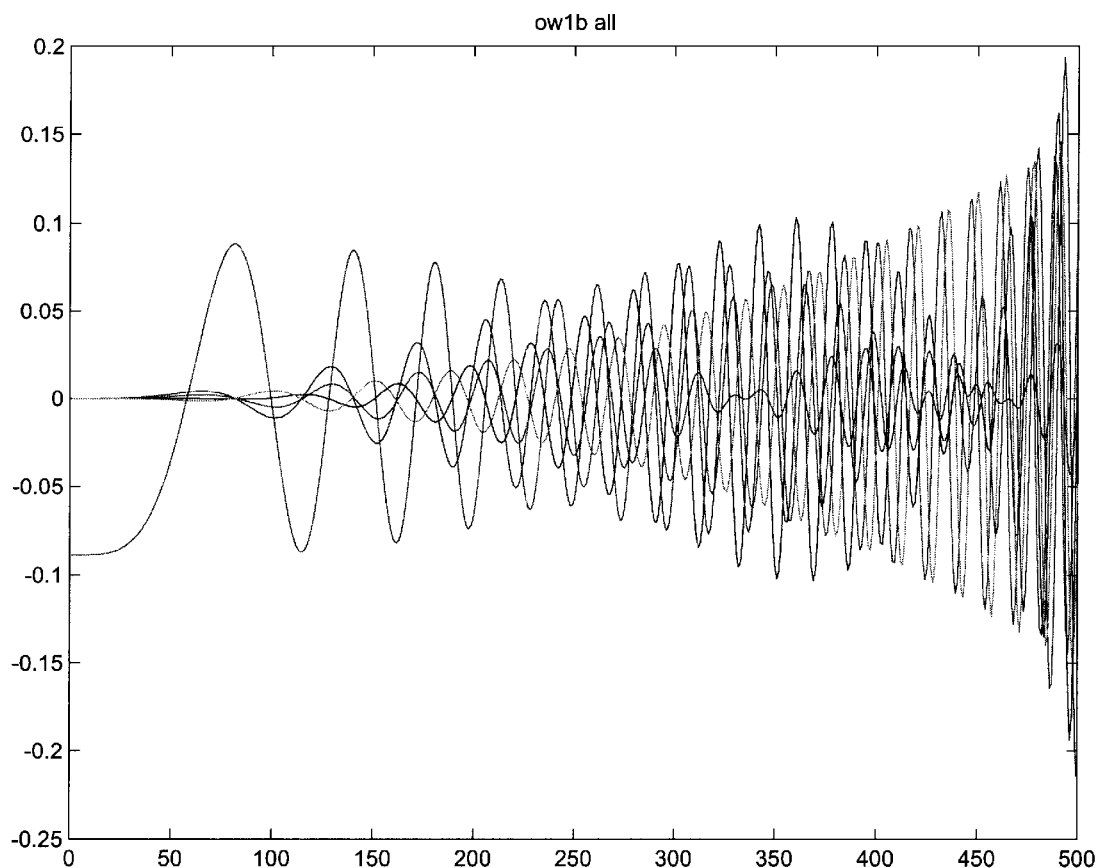
FIG. 18F shows the basis vectors depicted in FIGS. 18A, 18B, 18C, 18D and 18E combined in a single graph.
Figure 19A:
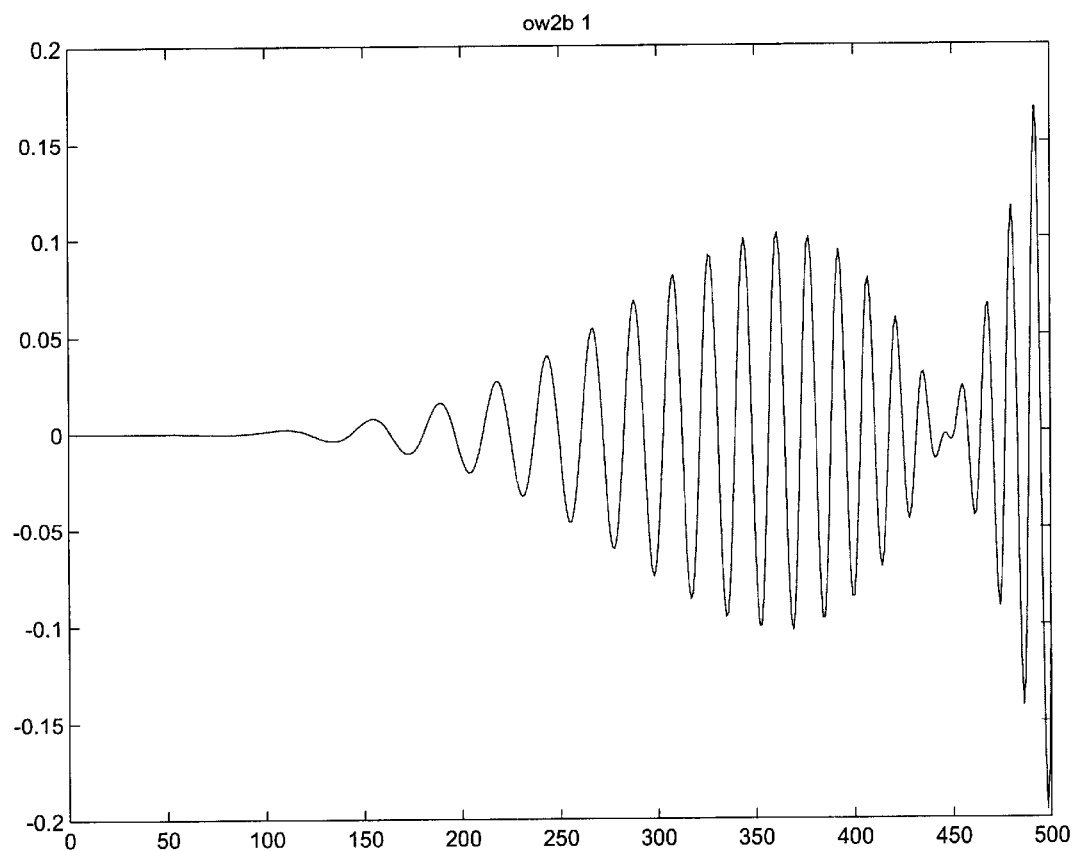
FIGS. 19A, 19B, 19C, 19D and 19E show basis vectors generated by AFRN II during the training phase and used to replicate inputted data.
Figure 19B:
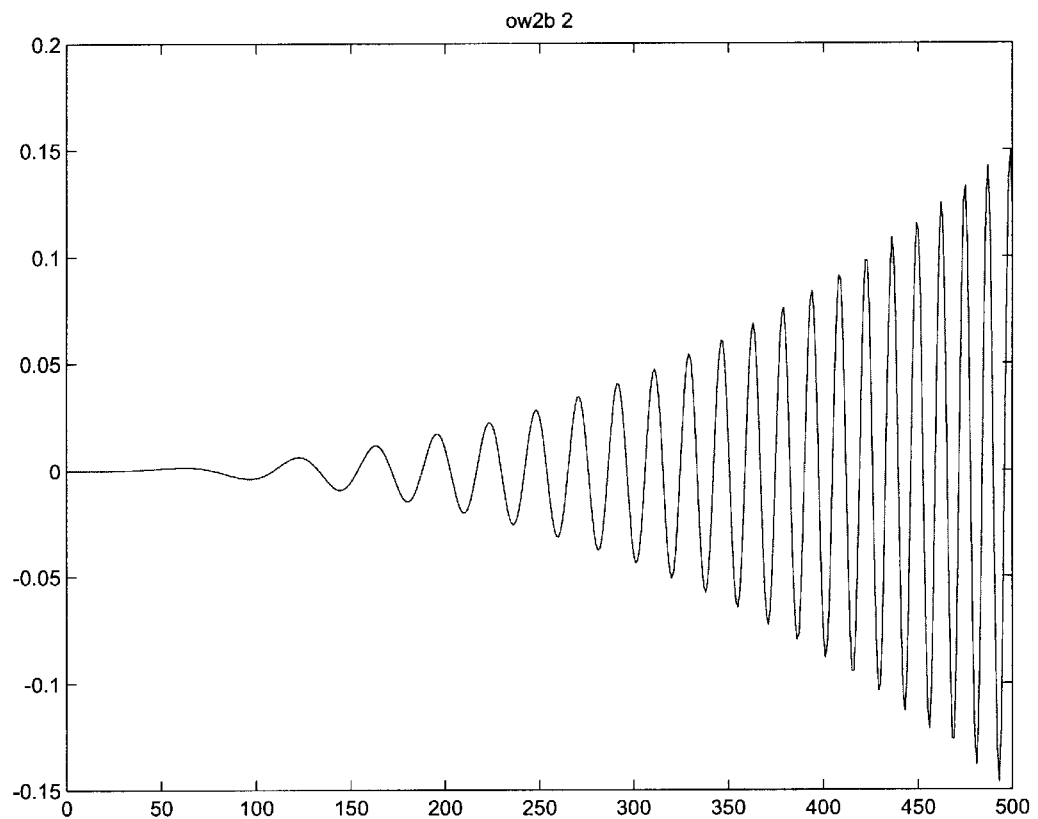
Figure 19C:
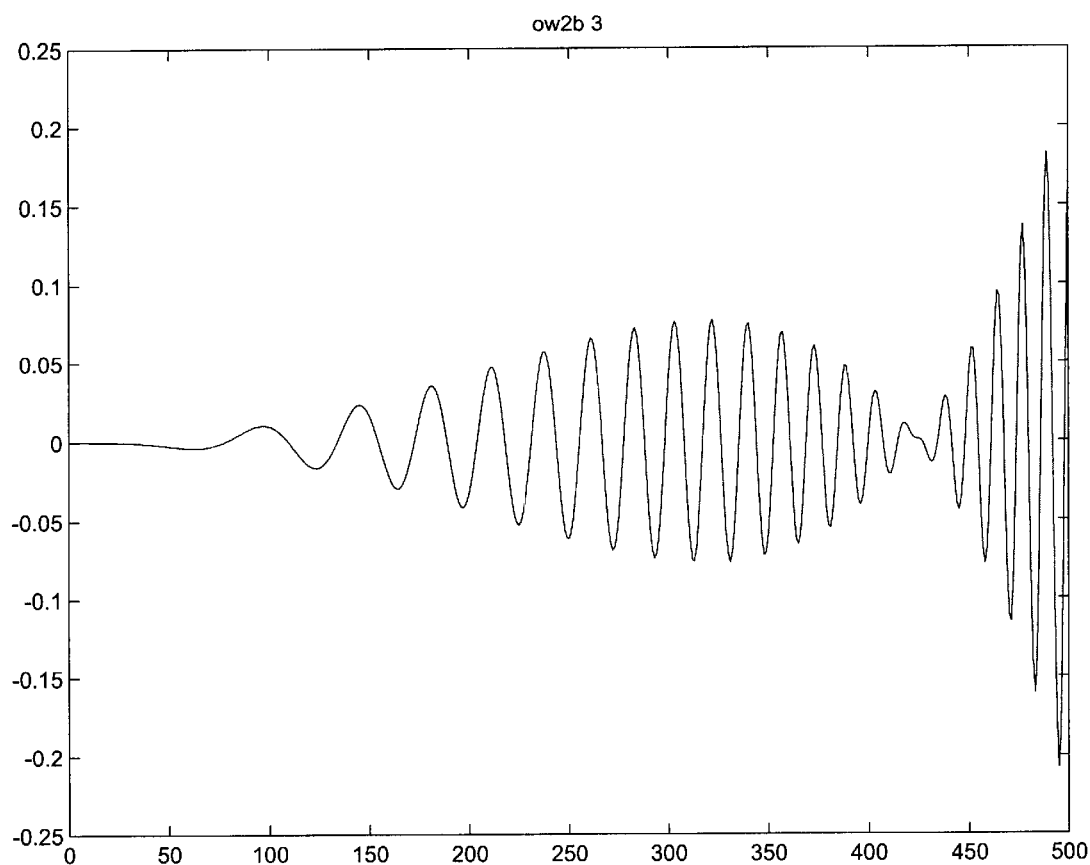
Figure 19D:
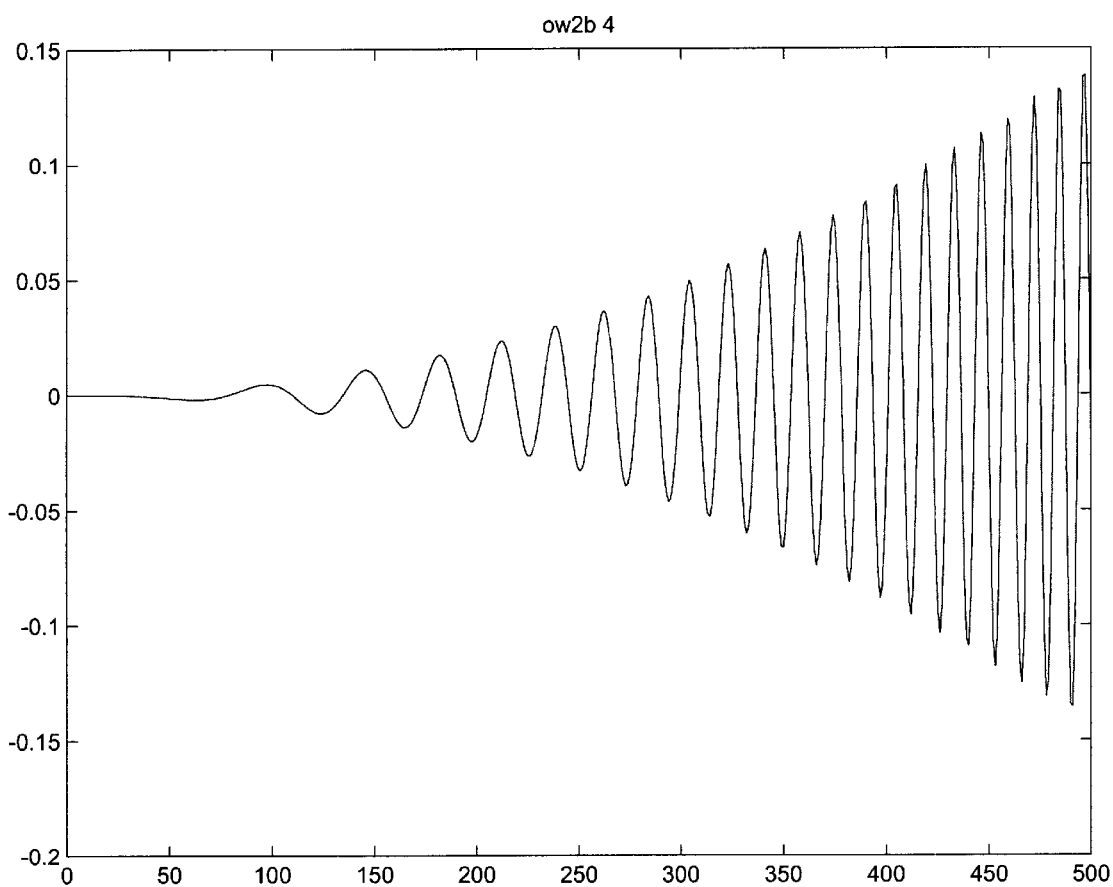
Figure 19E:
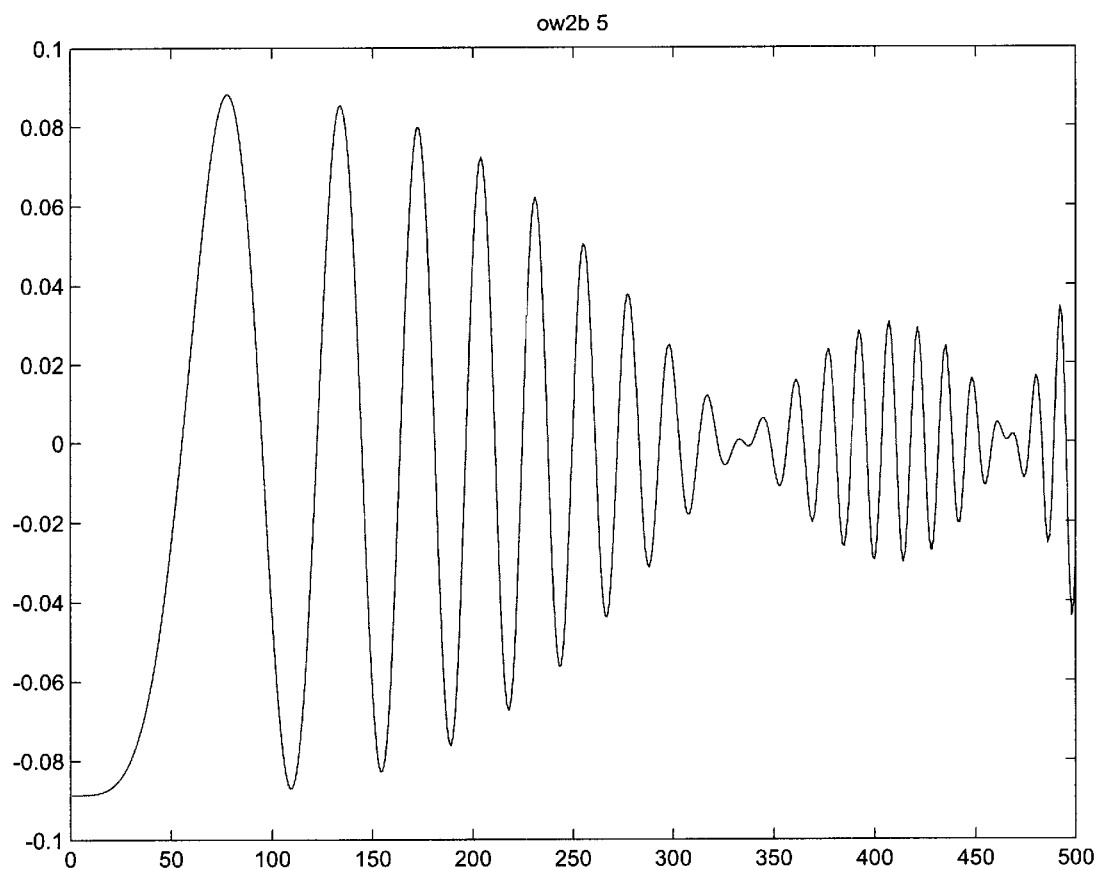
Figure 19F:
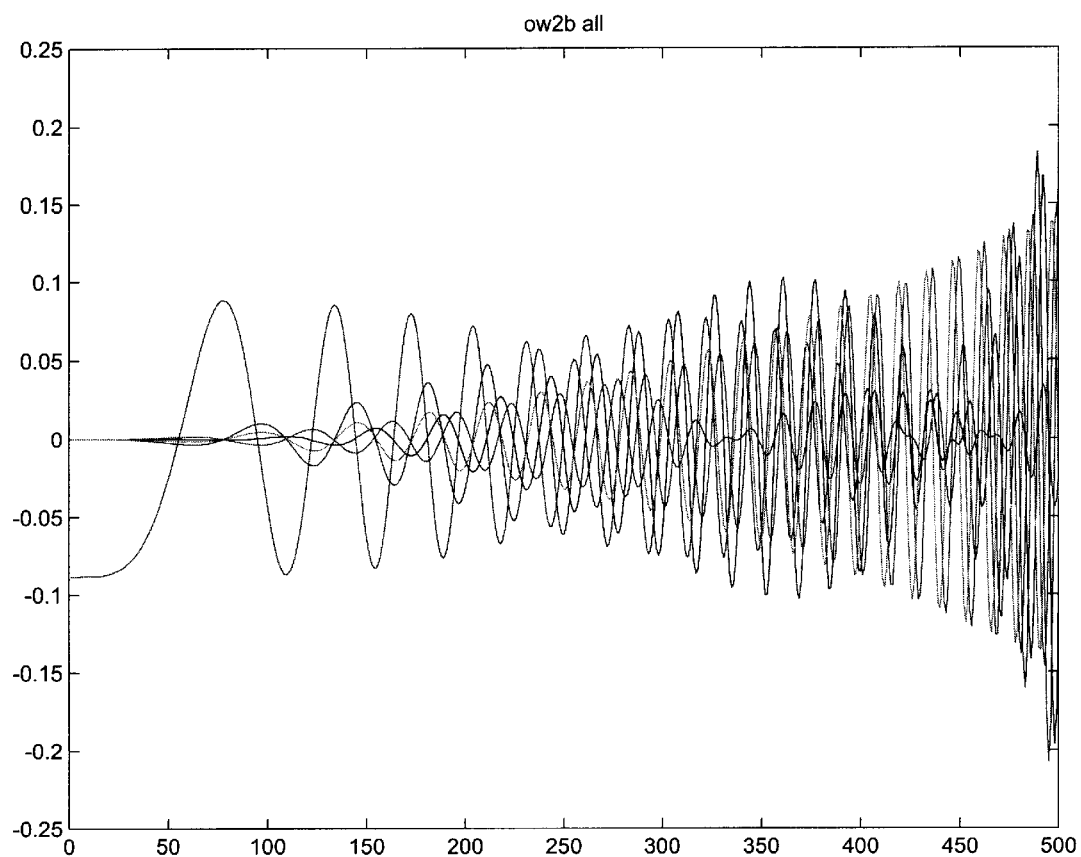
FIG. 19F shows the basis vectors depicted in FIGS. 19A, 19B, 19C, 19D and 19E combined in a single graph.
Figure 20A:
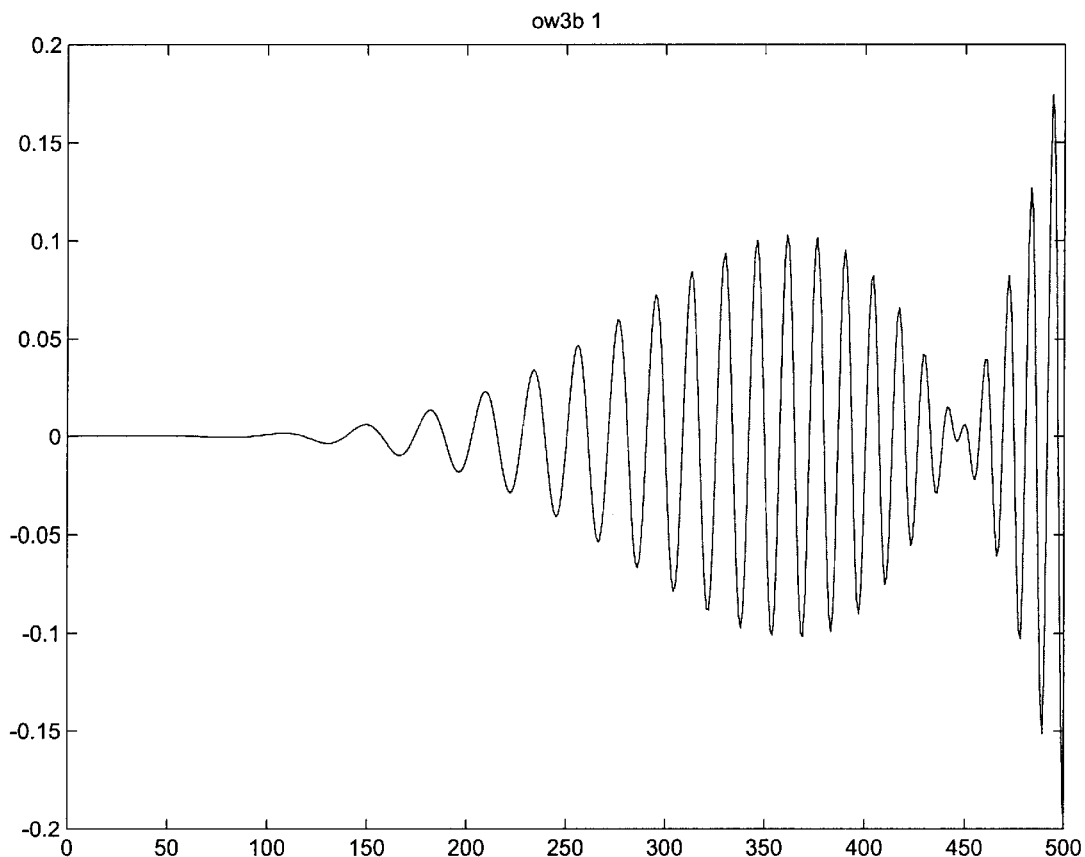
FIGS. 20A, 20B, 20C, 20D and 20E show basis vectors generated by AFRN III during the training phase and used to replicate inputted data.
Figure 20B:
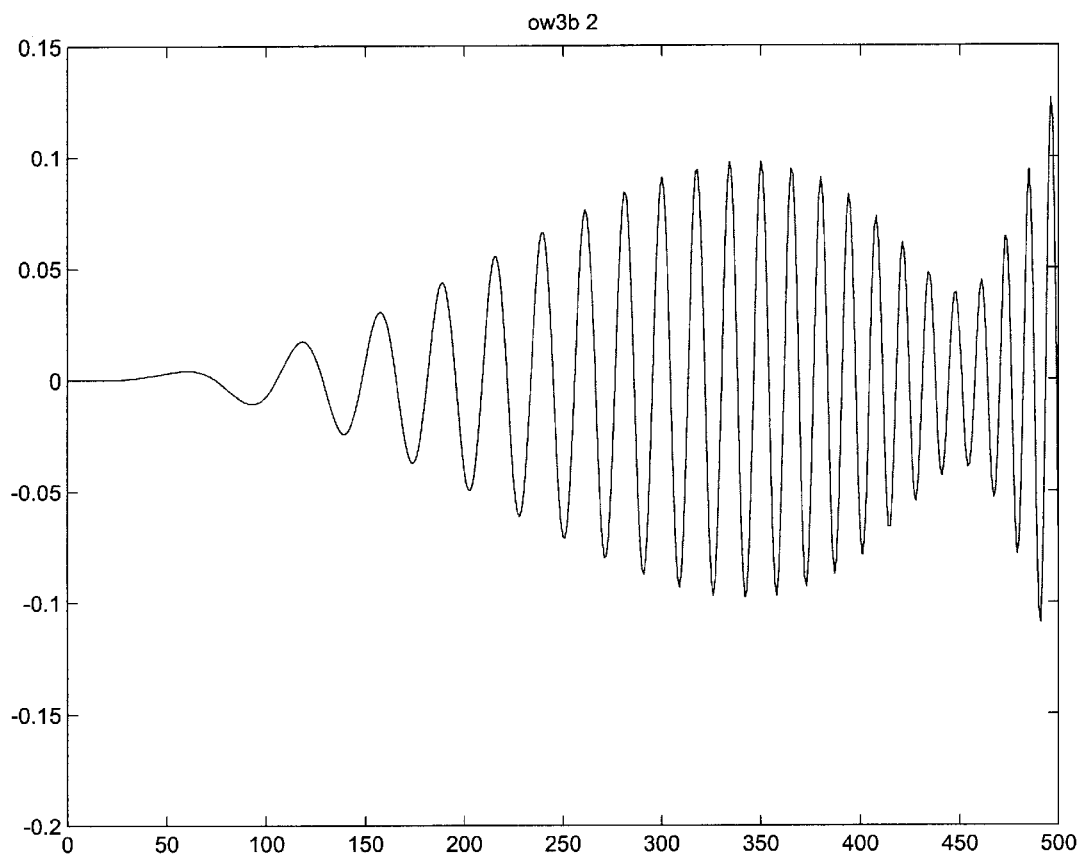
Figure 20C:
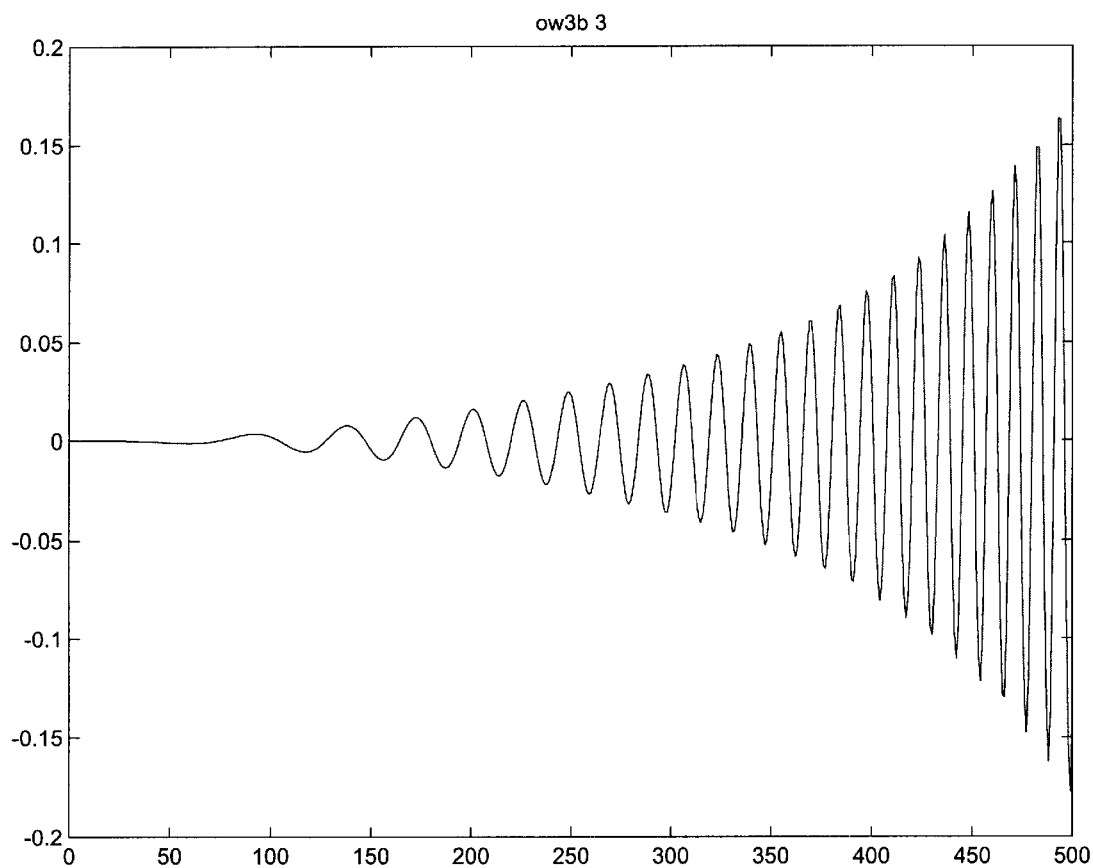
Figure 20D:
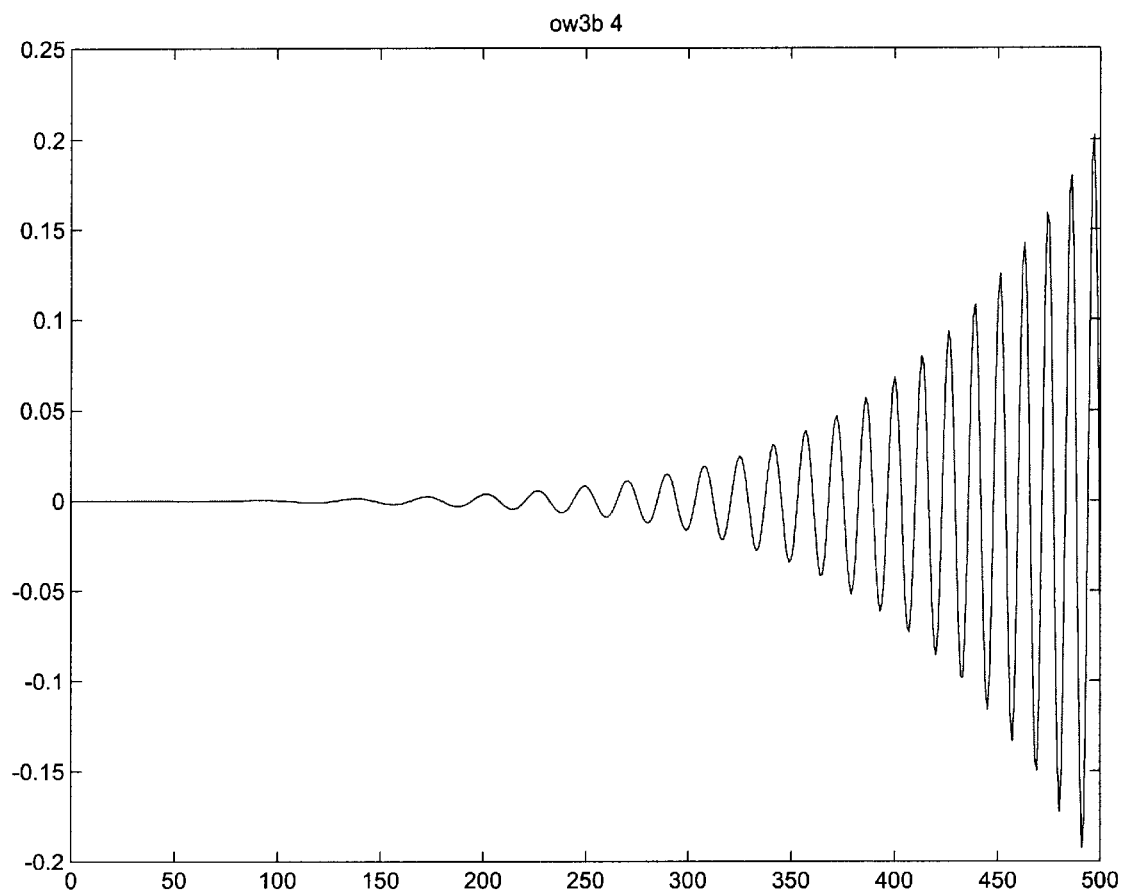
Figure 20E:
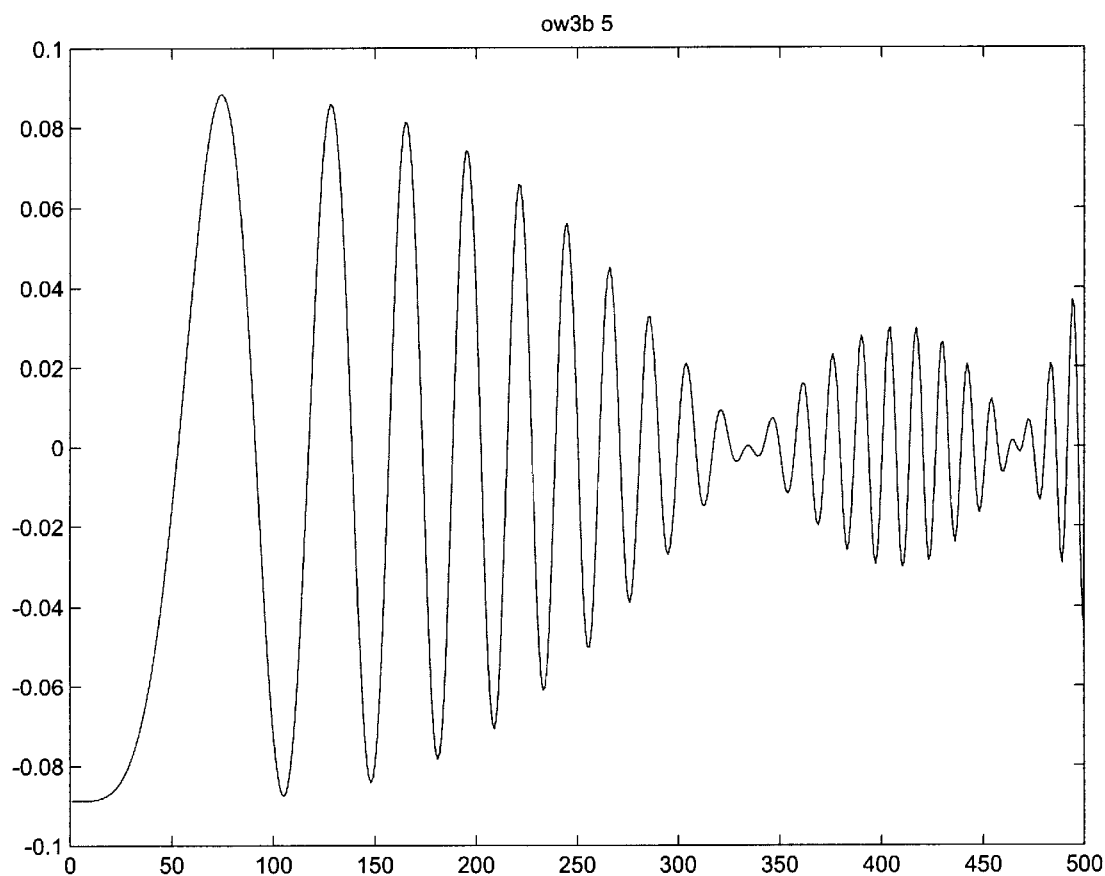
Figure 20F:
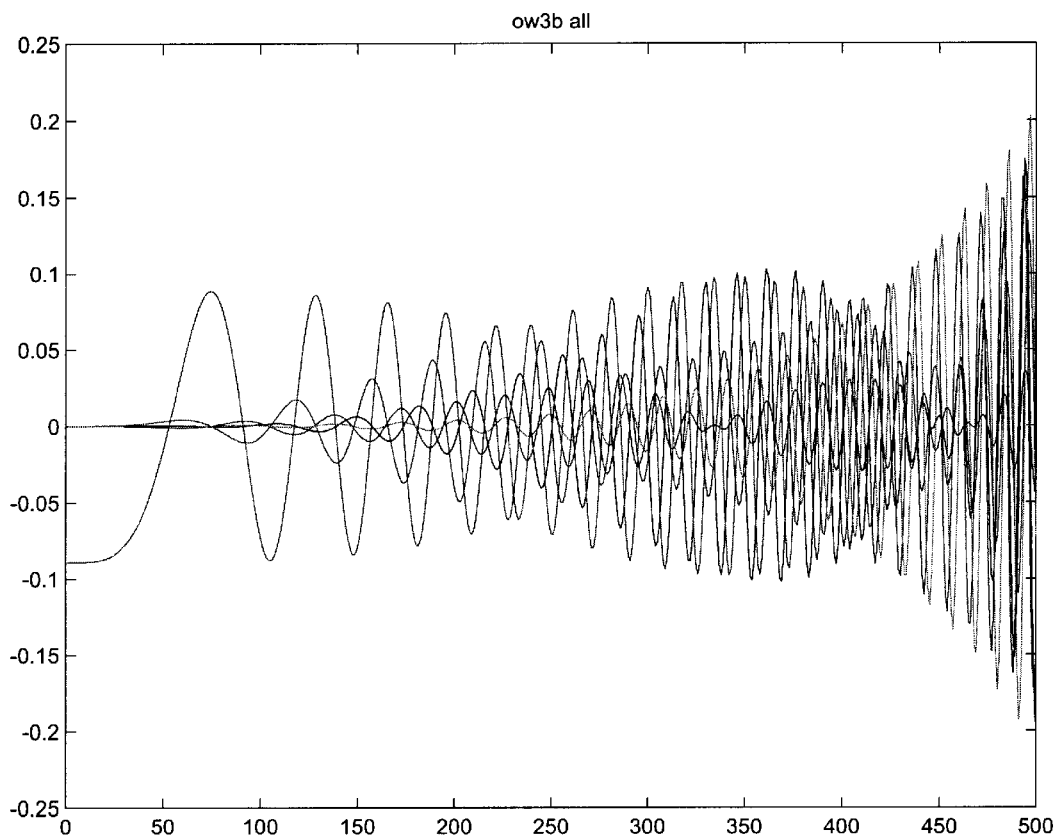
FIG. 20F depicts the basis vectors of FIGS. 20A–20E together.

During the training phase, a unique set of basis vectors was derived for each AFRN. Specifically, AFRN I includes the basis vectors shown in FIGS. 18A, 18B 18C, 18D and 18E, and further depicted together in one graph in FIG. 18F. AFRN II includes the basis vectors shown in FIGS. 19A, 19B, 19C, 19D and 19E, and further depicted together in one graph in FIG. 19F. AFRN III includes the basis vectors shown in FIGS. 20A, 20B, 20C, 20D and 20E, and further depicted together in one graph in FIG. 20F.

Figure 9A:
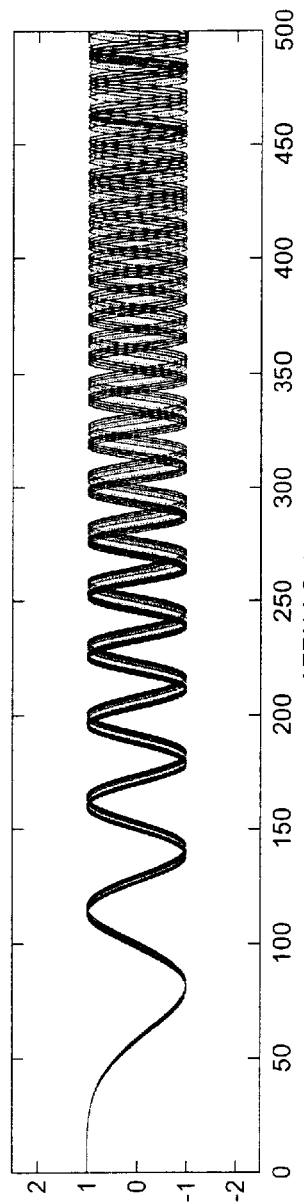
FIGS. 9A, 9B and 9C show input of reference set I, replicas of reference set I created by AFRN I during a training phase and an output error generated by comparing reference set I and the replicas generated by AFRN I.
Figure 9B:
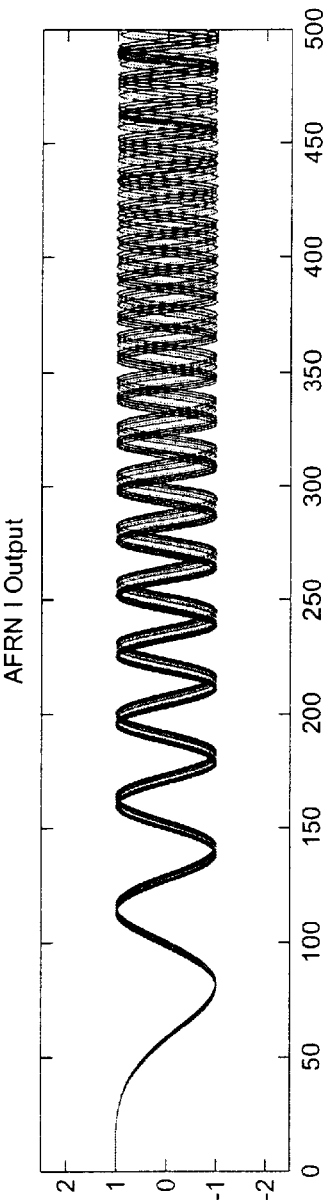
Figure 9C:
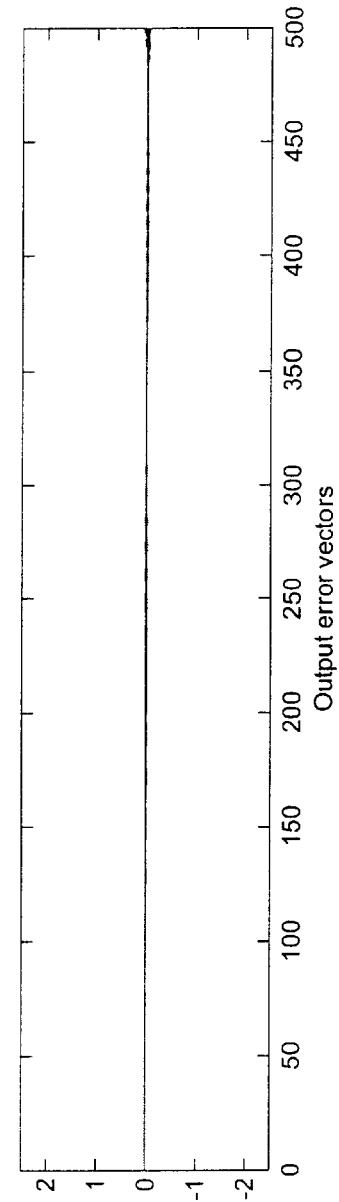

As was described above with respect to the flowchart in FIG. 6, AFRN I was trained by inputting reference set I (FIGS. 8A and 9A) in order to derive the set of basis vectors depicted in FIGS. 18A, 18B, 18C, 18D and 18E. Thereafter, AFRN I attempted to replicate reference set I, as shown in FIG. 9B. An output error (FIG. 9C) was generated by comparing reference set I and the replicas generated by AFRN I. The error shown in FIG. 9C is flat, indicating that the error was insignificant, and therefore the chirps in FIG. 9A were successfully replicated.

FIGS. 10A, 10B and 10C show the results of a test where an unknown chirp, Novel Class I was inputted into AFRN I. FIG. 10A shows the unknown data, Novel Class I. FIG. 10B shows the replicated data outputted from AFRN I. FIG. 10C shows the error resulting from a comparison of the output in FIG. 10B and the input shown in FIG. 10A. The error is negligible. Indeed, the error must be amplified to be visible to the naked eye. Therefore, pending further tests, the unknown data depicted in FIG. 10A should clearly be classified in Reference Set I.

Figures 10D, 10E, 10F:
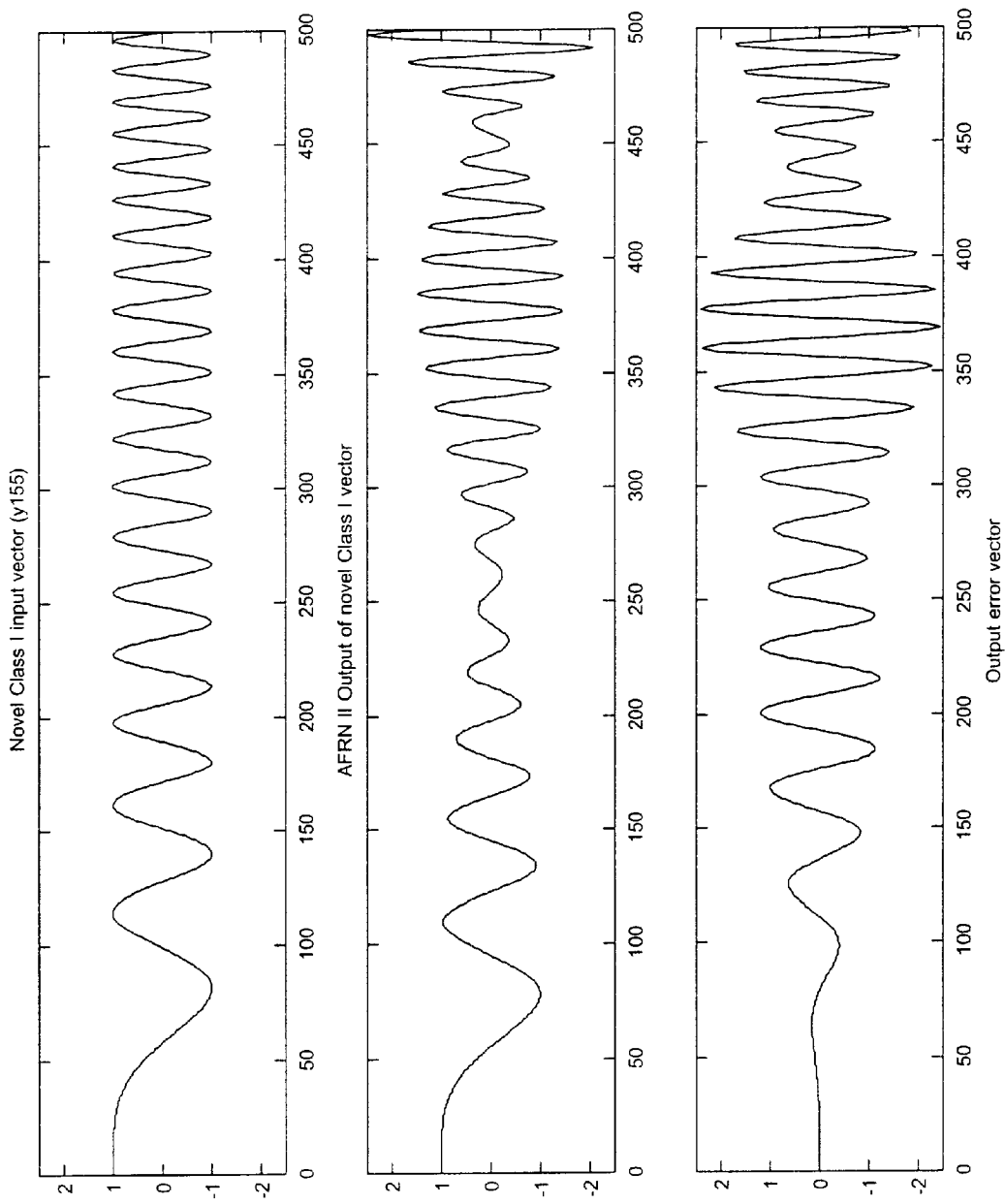
FIGS. 10D, 10E and 10F show a test similar to that of FIGS. 10A, 10B and 10C, except this test uses AFRN II.

FIGS. 10D, 10E, and 10F show a similar test using AFRN II. Novel Class I vector is again shown in FIG. 10D. FIG. 10E shows an attempted replica of Novel Class I vector by AFRN II. The error generated by comparing Novel Class I with the attempted replica is shown in FIG. 10F. Clearly, Novel Class I vector is not accurately replicated by AFRN II and cannot be classified by AFRN II.

Figures 10G, 10H, 10I:
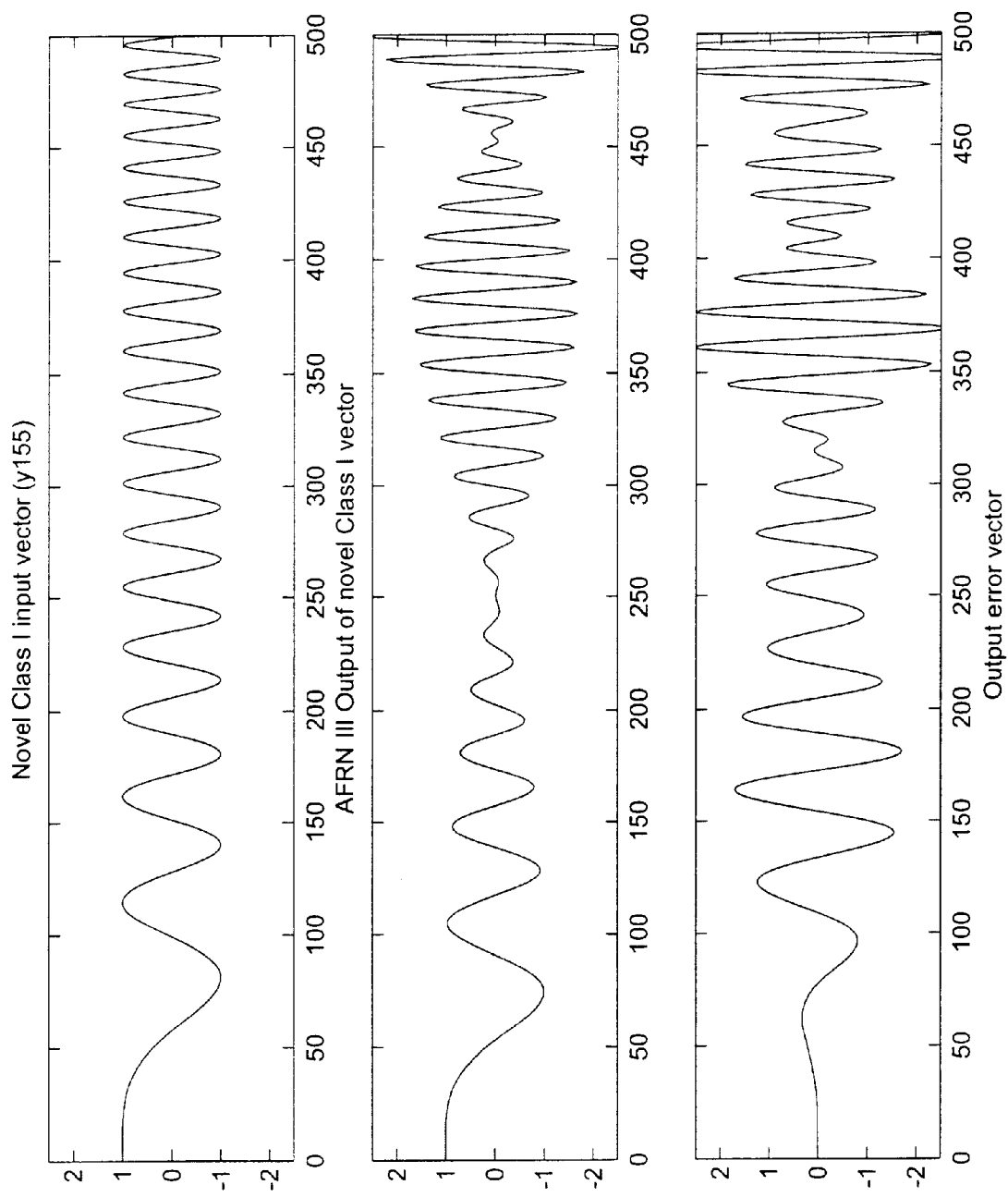
FIG. 10G, 10H and 10I show a test similar to that of FIGS. 10A, 10B and 10C, execpt this test uses AFRN III.

FIGS. 10G, 10H and 10I show yet another test using AFRN III. Novel Class I vector is again shown in FIG. 10G. FIG. 10H shows an attempted replica of Novel Class I vector by AFRN III. The error generated by comparing Novel Class I with the attempted replica is shown in FIG. 10I. Clearly, Novel Class I vector is not accurately replicated by AFRN III and cannot be classified by AFRN III.

Figure 11A:
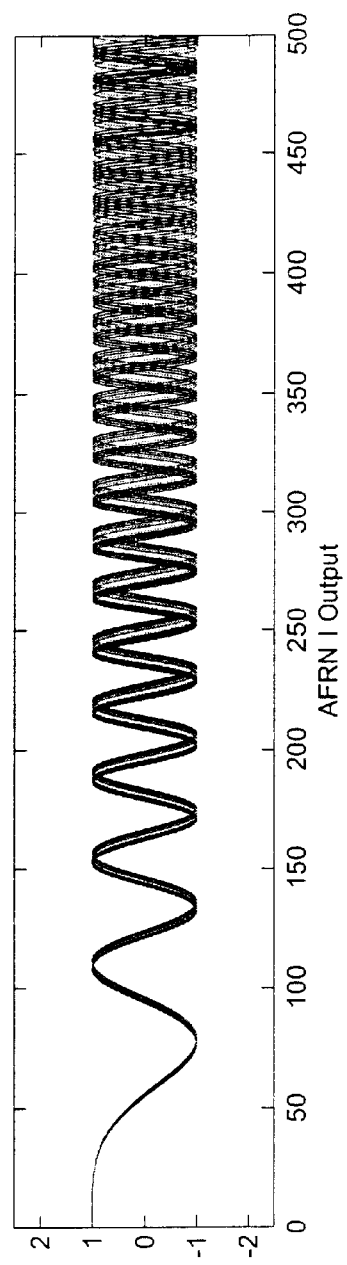
FIGS. 11A, 11B and 11C showing input reference vectors II (input into AFRN I), the output from AFRN I attempting to replicate input reference vectors II and the output error demonstrating the inability of AFRN I to replicate reference vectors II.
Figure 11B:
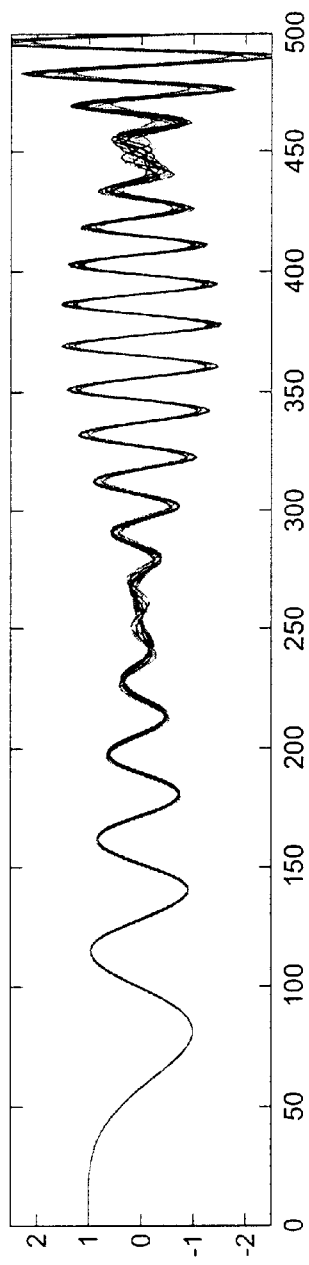
Figure 11C:
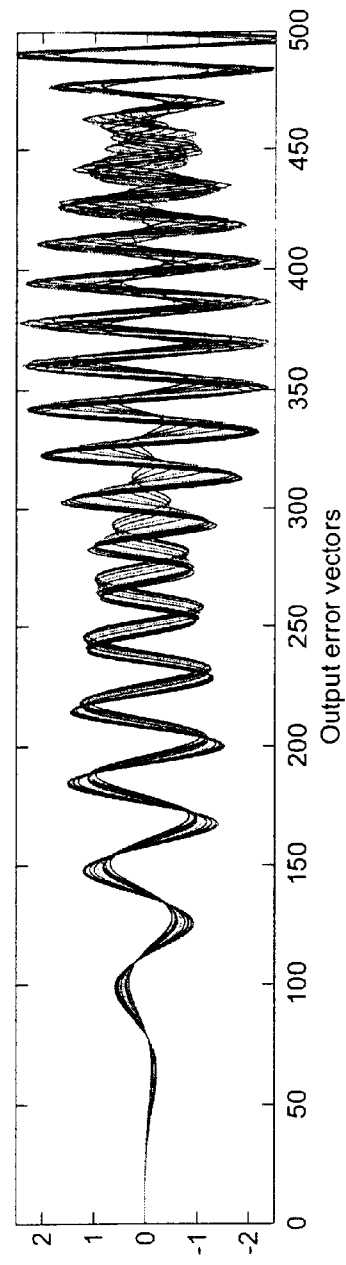

To further test AFRN 1, data from Reference Set II shown in FIG. 11A was inputted. AFRN I generated replicas depicted in FIG. 11B. Visual comparisons between the data in FIG. 11A and the replica depicted in FIG. 11B indicate that the two sets of data are not very similar. However, the error output depicted in FIG. 11C shows clearly that the Reference Set II data should not be classified with Reference Set I. Even with no amplification, FIG. 11C clearly shows gross errors. Therefore, the data curve in FIG. 11A cannot be categorized as being part of a data category corresponding to Reference Set I.

Similarly, data from Reference Set III shown in FIG. 11D was inputted. AFRN I generated replicas depicted in FIG. 11E. Visual comparisons between the data in FIG. 11D and the replica depicted in FIG. 11E indicate that the two sets of data are not very similar. Further, the error output depicted in FIG. 11F shows clearly that the Reference Set III data should not be classified with Reference Set I. Even with no amplification, FIG. 11F clearly shows gross errors. Therefore, the data curve in FIG. 11D cannot be categorized as being part of a data category corresponding to Reference Set I.

Figure 12A:
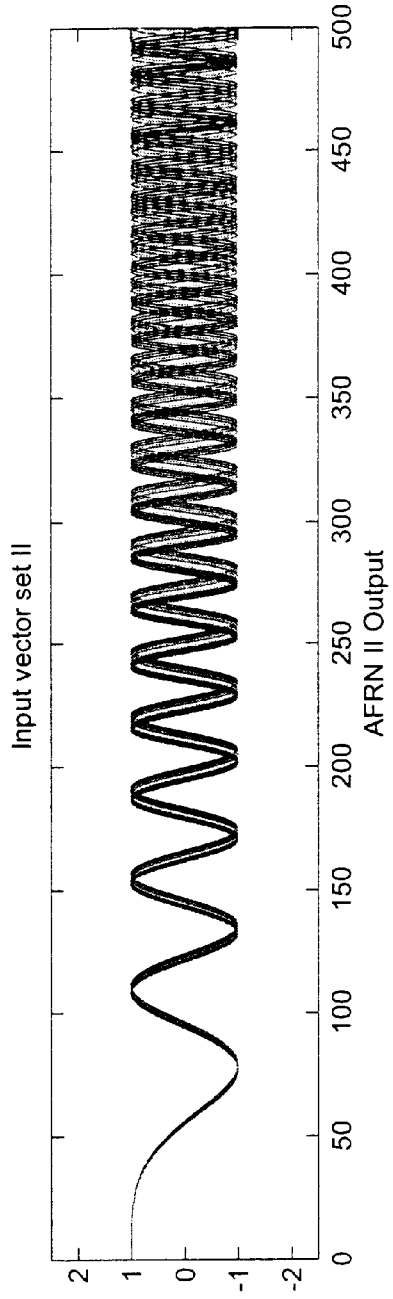
FIGS. 12A, 12B and 12C show input of reference set II, replicas of reference set II generated by AFRN II during the training phase and an output error generated by comparing reference set II and the replicas created by AFRN II.
Figure 12B:
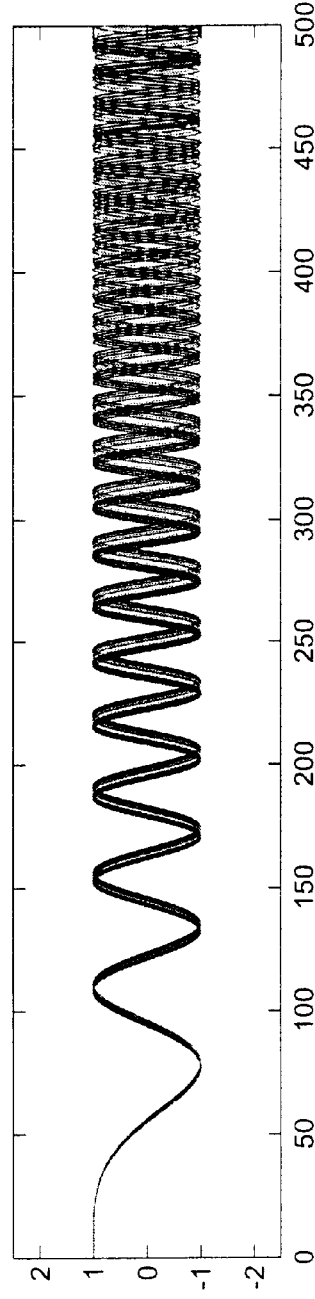
Figure 12C:
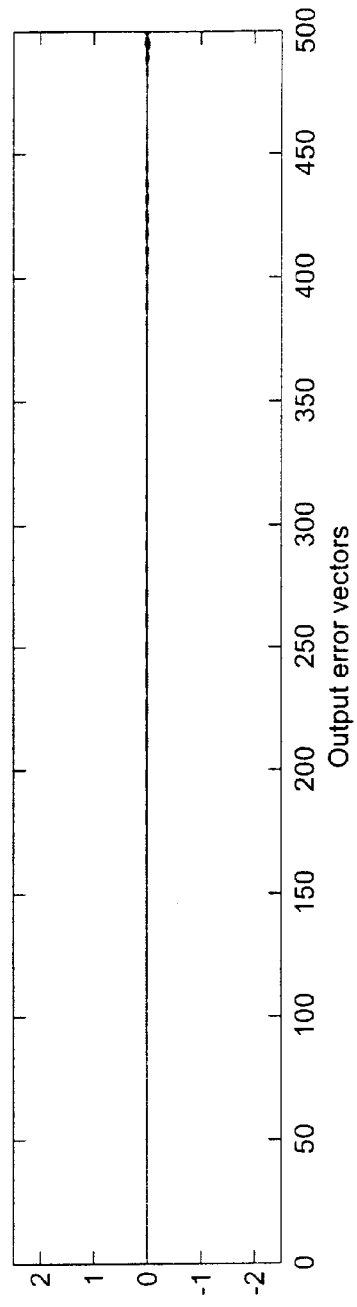

AFRN II was trained by inputting reference set II (FIGS. 8B and 12A) in order to derive the set of basis vectors depicted in FIGS. 19A, 19B, 19C, 19D and 19E. Thereafter, AFRN II attempted to replicate reference set II, as shown in FIG. 12B. An output error (FIG. 12C) was generated by comparing reference set II and the replicas generated by AFRN II. The error shown in FIG. 12C is flat, indicating that the error was insignificant, and therefore the chirps in FIG. 12A were successfully replicated.

Figures 13A, 13B, 13C:
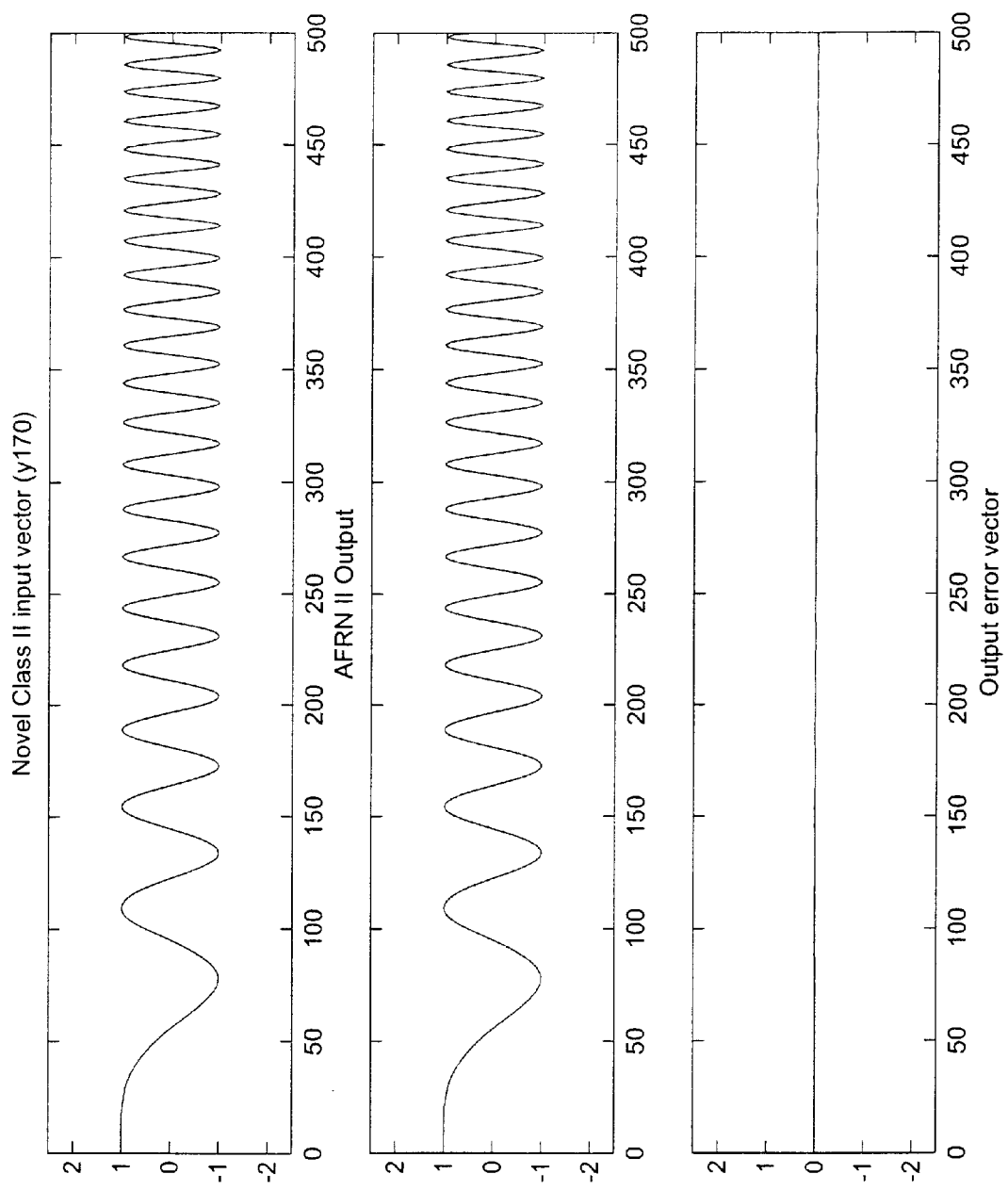
FIGS. 13A, 13B and 13C show a novel (unknown) input having features similar to reference set II, a replica of the novel input generated by trained AFRN II and output error.

FIGS. 13A, 13B and 13C show the results of a test where an unknown chirp, Novel Class II vector, was inputted into AFRN II. FIG. 13A shows the unknown Novel Class II vector. FIG. 13B shows the replicated data outputted from AFRN II. FIG. 13C shows the error resulting from a comparison of the output in FIG. 13B and the input shown in FIG. 13A. The error is negligible. Therefore, pending further tests, the unknown data depicted in FIG. 13A should clearly be classified in Reference Set II.

Figures 13D, 13E, 13F:
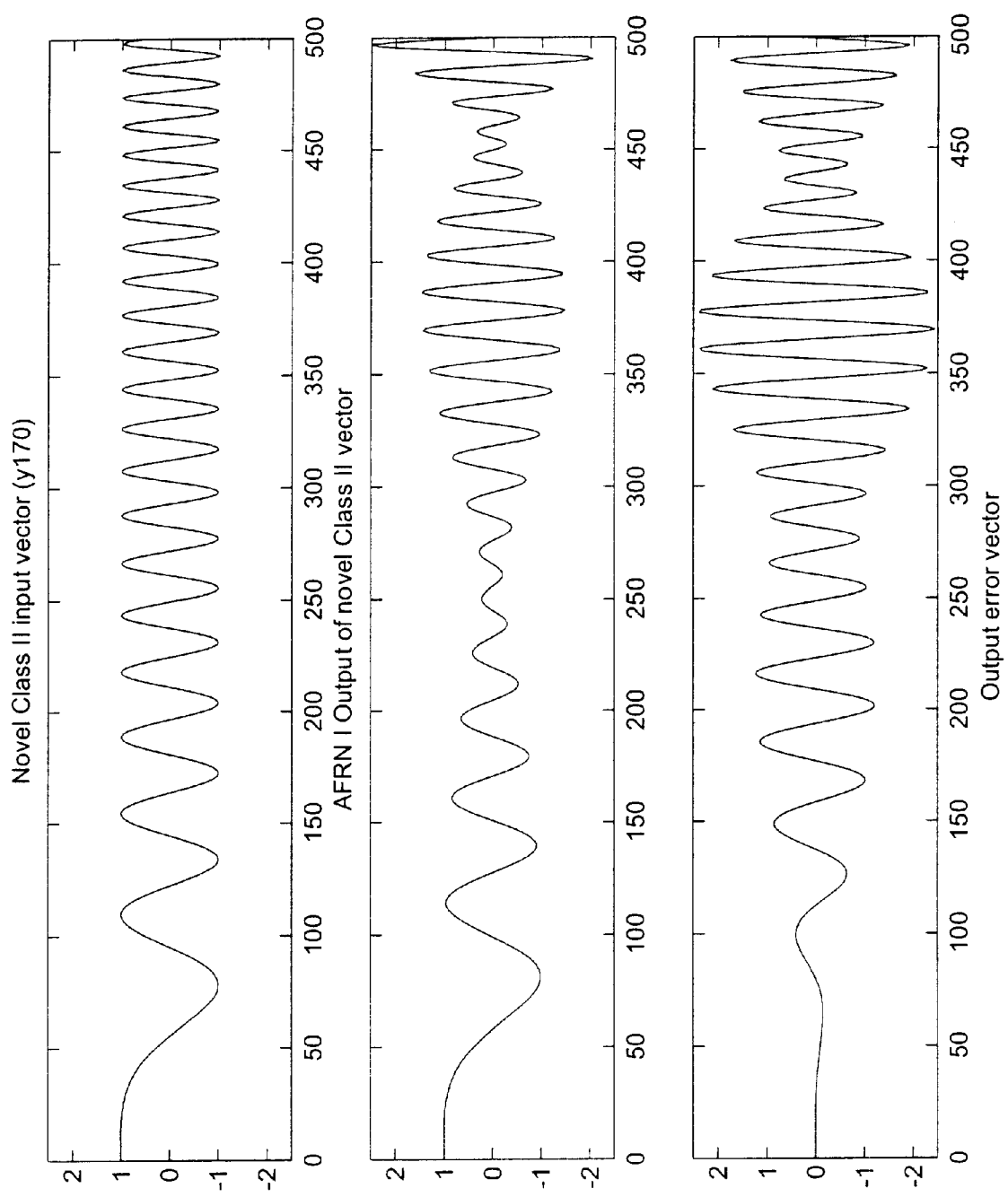
FIGS. 13D, 13E and 13F show a test similar to that of FIGS. 13A, 13B and 13C, except this test uses AFRN I.

FIGS. 13D, 13E and 13F show a similar test using AFRN I. Novel Class II vector is again shown in FIG. 13D. FIG. 13E shows an attempted replica of Novel Class II vector generated by AFRN I. The error generated by comparing Novel Class II with the attempted replica is shown in FIG. 13F. Clearly, Novel Class II vector is not accurately replicated by AFRN I and cannot be classified by AFRN I.

Figures 13G, 13H, 13I:
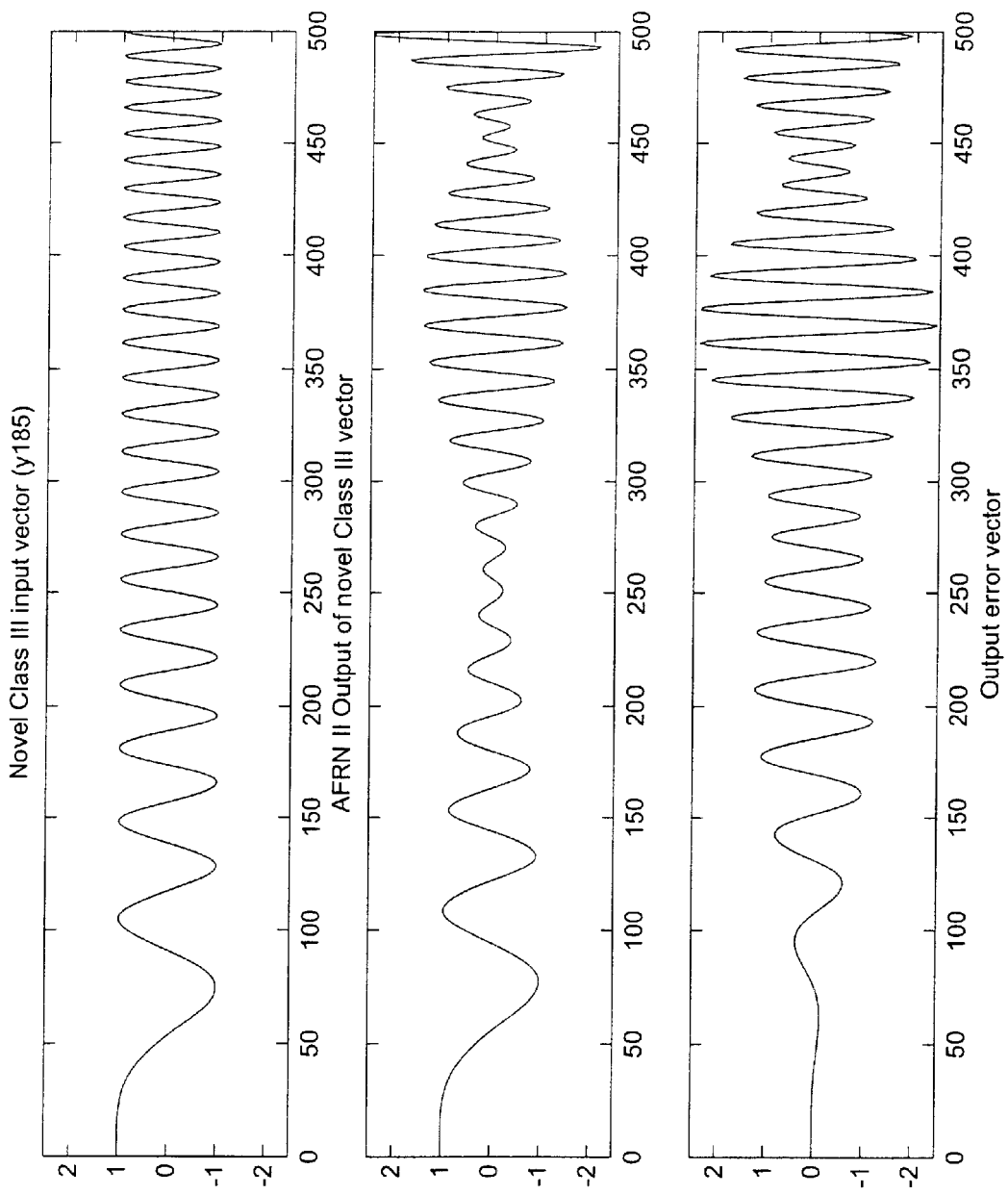
FIGS. 13G, 13H and 13I show a test similar to FIGS. 13A, 13B and 13C, except this test uses AFRN III.

FIGS. 13G, 13H and 13I show yet another test using AFRN III. Novel Class II vector is again shown in FIG. 13G. FIG. 13H shows an attempted replica of Novel Class II vector by AFRN III. The error generated by comparing Novel Class II with the attempted replica is shown in FIG. 13I. Clearly, Novel Class II vector is not accurately replicated by AFRN III and cannot be classified by AFRN III.

Figure 14A:
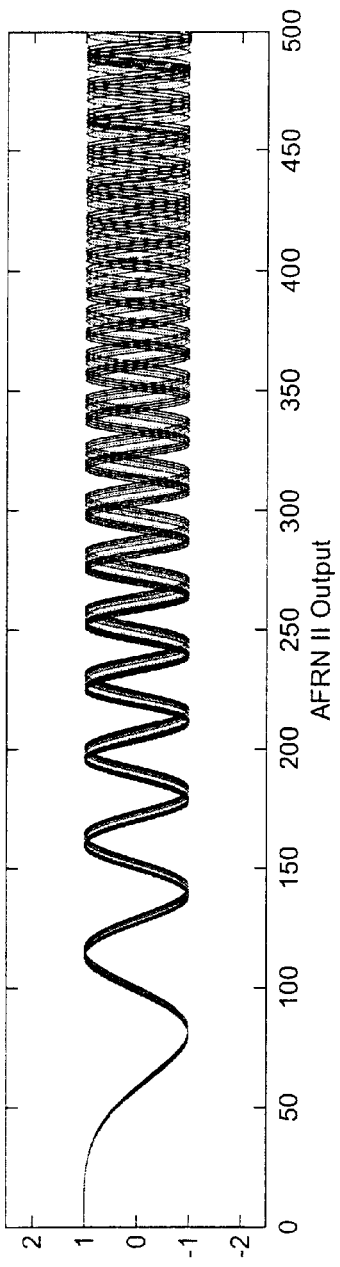
FIGS. 14A, 14B and 14C showing input reference vectors I (input into trained AFRN II), the output from AFRN II attempting to replicate input reference vectors I and the output error demonstrating the inability of AFRN II to replicate reference vectors I.
Figure 14B:
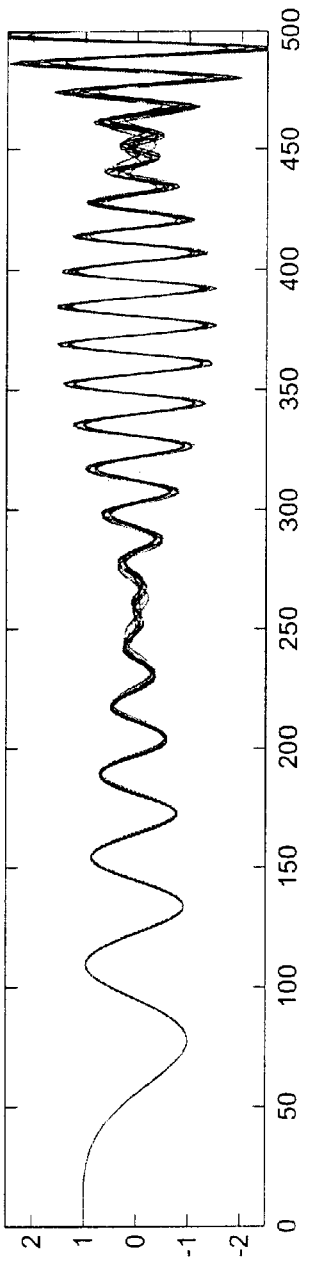
Figure 14C:
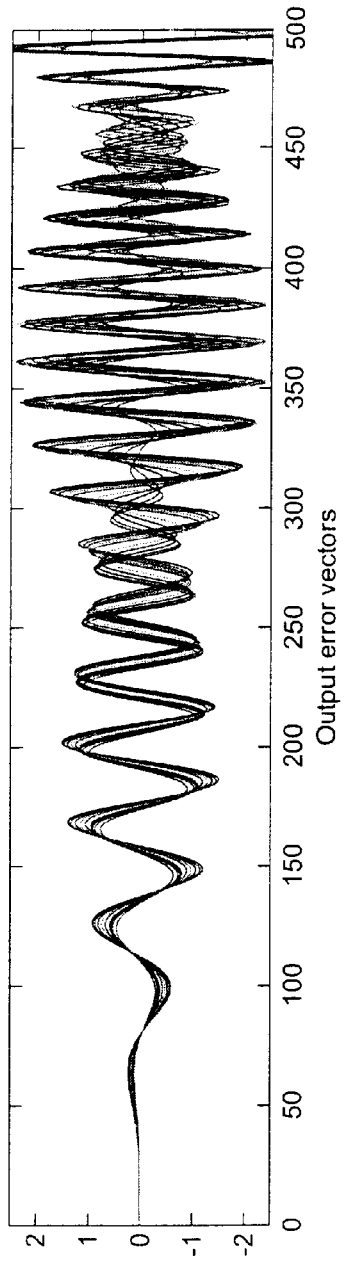

To further test AFRN II, data from Reference Set I shown again in FIG. 14A was inputted into AFRN II. AFRN II attempted to generate replicas depicted in FIG. 14B. Visual comparisons between the data in FIG. 14A and the replica depicted in FIG. 14B indicate that the two sets of data are not the same. The error output depicted in FIG. 14C clearly confirms that the Reference Set I data should not be classified with Reference Set II. FIG. 14C clearly shows gross errors in the replication process. Therefore, the data curve in FIG. 14A cannot be categorized as being part of a data category corresponding to Reference Set II.

Figures 14D, 14E, 14F:
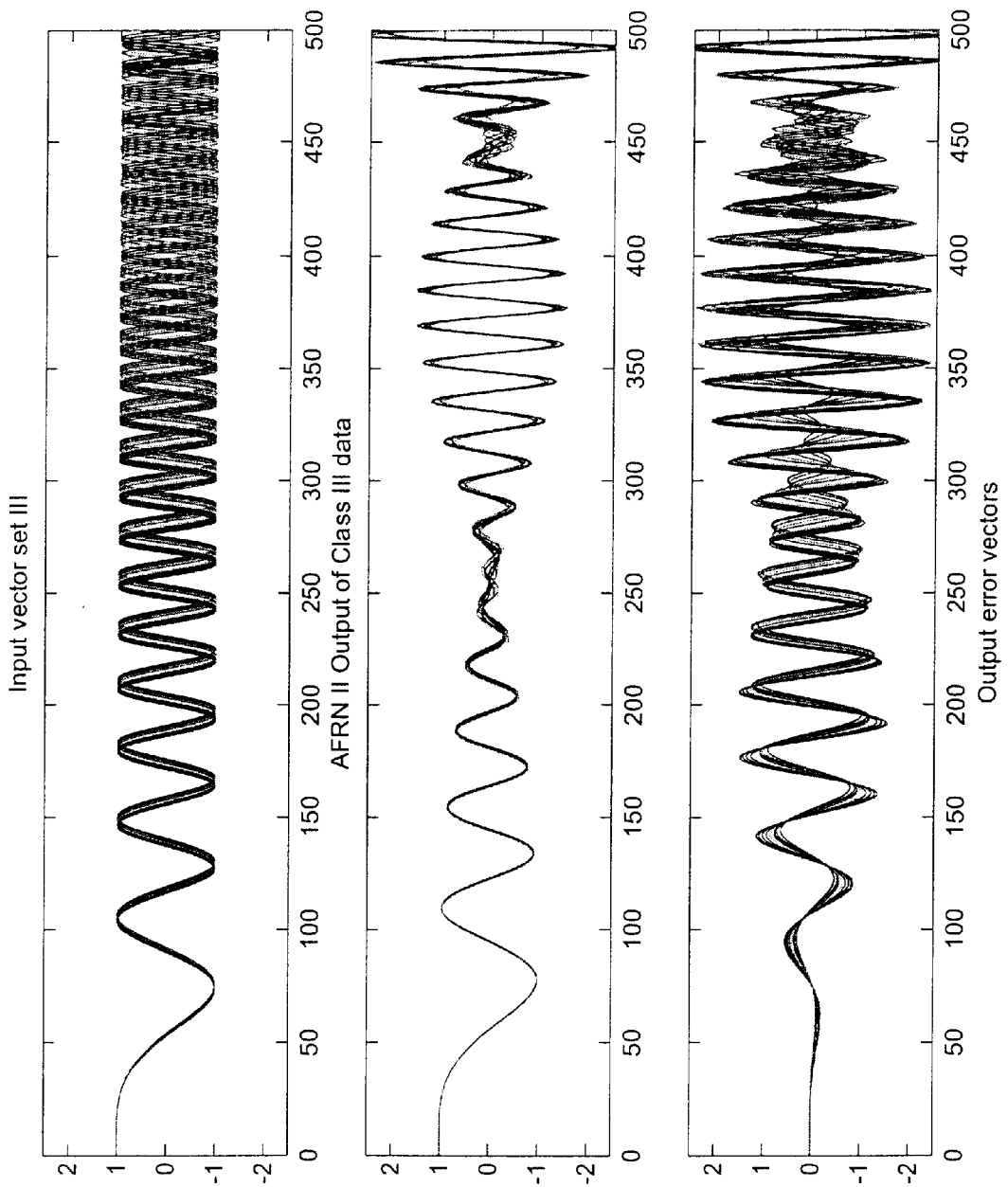
FIGS. 14D, 14E and 14F showing input reference vectors III (input into AFRN II), the output from AFRN II attempting to replicate input reference vectors III and the output error demonstrating the inability of AFRN II to replicate reference vectors III.

Similarly, data from Reference Set III shown again in FIG. 14D was inputted. AFRN II attempted to generate replicas, as is shown in FIG. 14E. Visual comparisons between the data in FIG. 14D and the replicas depicted in FIG. 14E indicate that the two sets of data are not very similar. Further, the error output depicted in FIG. 14F shows clearly that the Reference Set III data should not be classified with Reference Set II. Even with no amplification, FIG. 14F clearly shows gross errors. Therefore, the data curve in FIG. 14D cannot be categorized as being part of a data category corresponding to Reference Set II.

AFRN III was trained by inputting reference set III (FIGS. 8C and 15A) in order to derive the set of basis vectors depicted in FIGS. 20A, 20B, 20C, 20D and 20E. Thereafter, AFRN III attempted to replicate reference set III, as shown in FIG. 15B. An output error (FIG. 15C) was generated by comparing reference set III and the replicas generated by AFRN III. The error shown in FIG. 15C is flat, indicating that the error was insignificant, and therefore the chirps in FIG. 15A were successfully replicated.

Figures 16A, 16B, 16C:
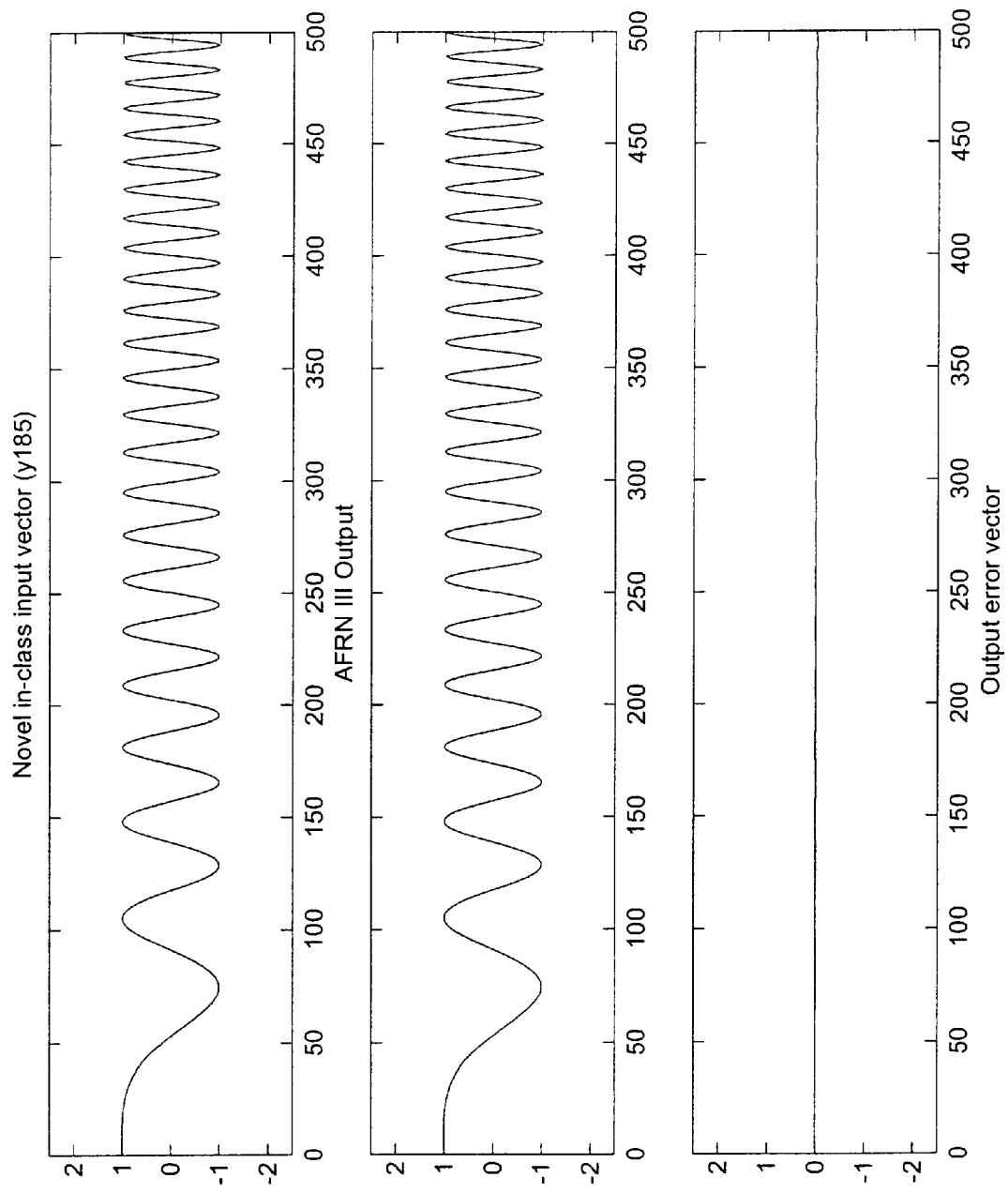
FIGS. 16A, 16B and 16C show a novel (unknown) input having features similar to reference set III, a replica of the novel input generated by trained AFRN III and output error.

FIGS. 16A, 16B and 16C show the results of a test where an unknown chirp, Novel Class III vector, was inputted into AFRN III. FIG. 16A shows the unknown data. FIG. 16B shows the replicated data outputted from AFRN III. FIG. 16C shows the error resulting from a comparison of the output in FIG. 16B and the input shown in FIG. 16A. The error is negligible. Therefore, pending further tests, the unknown data depicted in FIG. 16A should clearly be classified in Reference Set III.

Figures 16D, 16E, 16F:
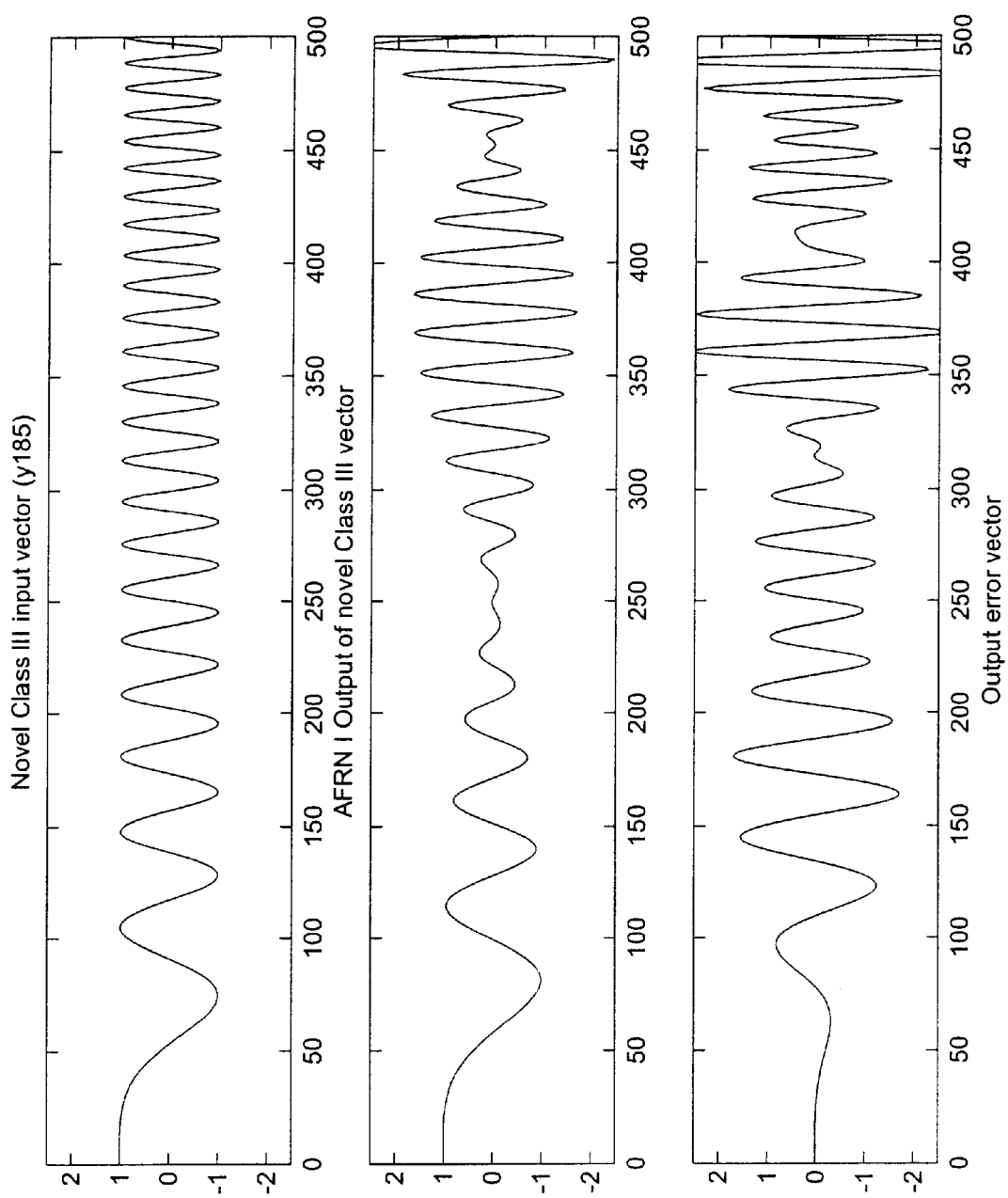
FIGS. 16D, 16E and 16F show a test similar to that of FIGS. 16A, 16B and 16C, except this test uses AFRN I.

FIGS. 16D, 16E and 16F show a similar test using AFRN I. Novel Class III vector is again shown in FIG. 163D. FIG. 16E shows an attempted replica of Novel Class III vector generated by AFRN 1. The error generated by comparing Novel Class III with the attempted replica is shown in FIG. 16F. Clearly, Novel Class III vector is not accurately replicated by AFRN I and cannot be classified by AFRN I.

Figures 16G, 16H, 16I:
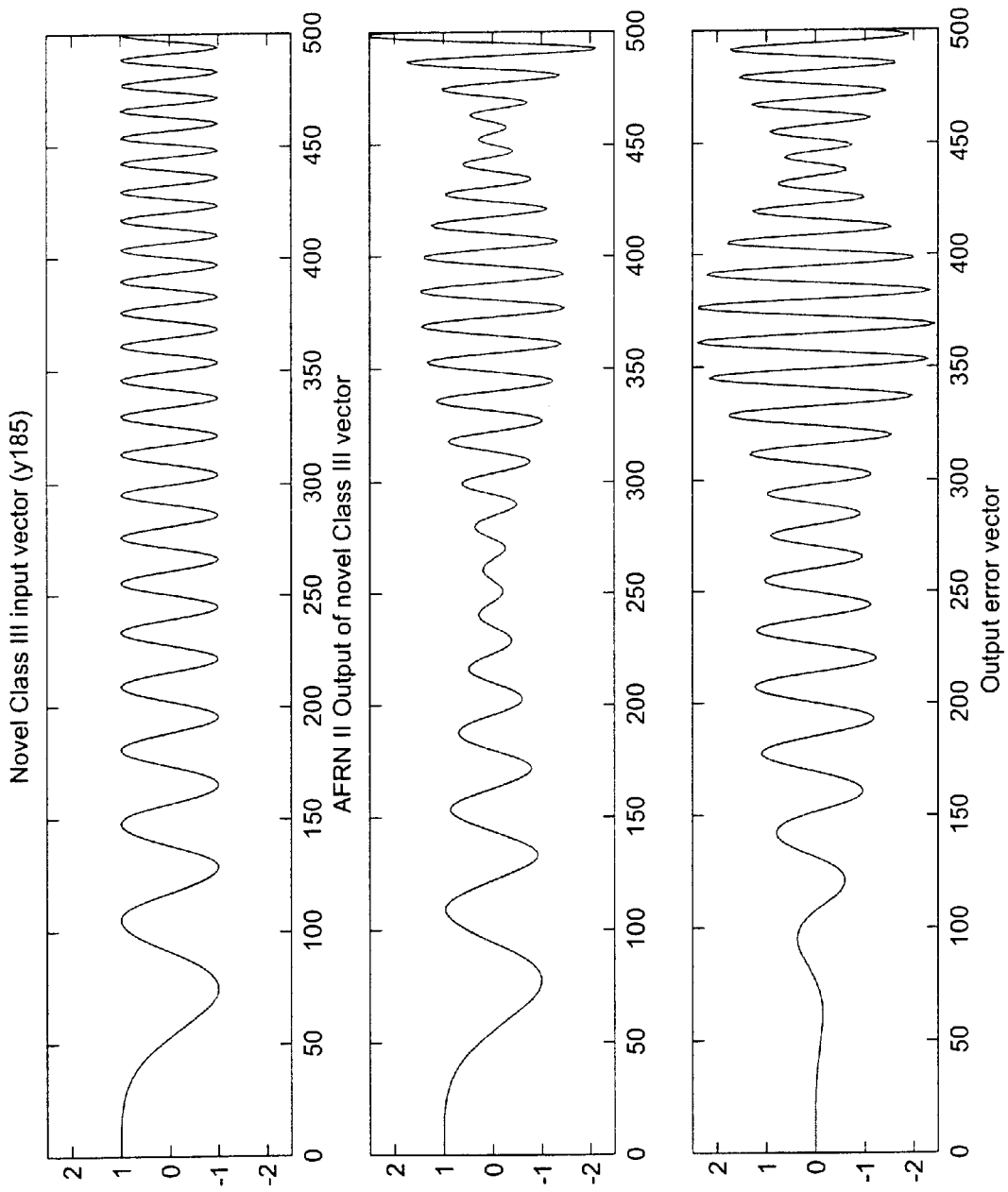
FIGS. 16G, 16H and 16I show a test similar to that of FIGS. 16A, 16B and 16C, except this test uses AFRN II.

FIGS. 16G, 16H and 16I show yet another test using AFRN II. Novel Class III vector is again shown in FIG. 16G. FIG. 16H shows an attempted replica of Novel Class III vector by AFRN II. The error generated by comparing Novel Class III with the attempted replica is shown in FIG. 16I. Clearly, Novel Class III vector is not accurately replicated by AFRN II and cannot be classified by AFRN II.

To further test AFRN III, data from Reference Set I, shown again in FIG. 17A, was inputted into AFRN III. AFRN III attempted to generate replicas depicted in FIG. 17B. Visual comparisons between the data in FIG. 17A and the replica depicted in FIG. 17B indicate that the two sets of data are not the same. The error output depicted in FIG. 17C clearly confirms that the Reference Set I data should not be classified with Reference Set III. FIG. 17C clearly shows gross errors in the replication process. Therefore, the data curve in FIG. 17A cannot be categorized as being part of a data category corresponding to Reference Set III.

Figures 17D, 17E, 17F:
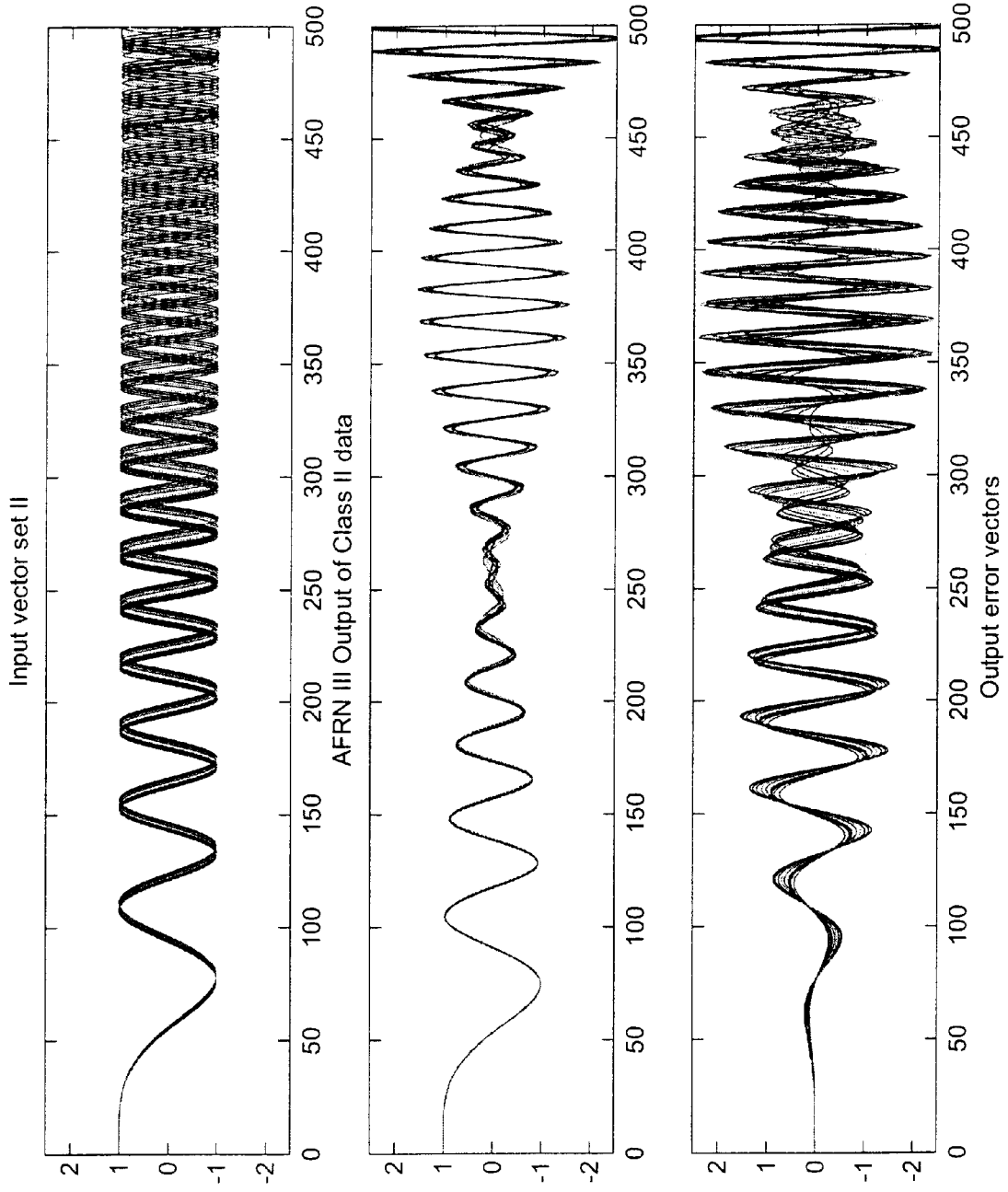
FIGS. 17D, 17E and 17F showing input reference vectors II (input into AFRN III), the output from AFRN III attempting to replicate input reference vectors II and the output error demonstrating the inability of AFRN III to replicate reference vectors II.

Similarly, data from Reference Set II shown again in FIG. 17D was inputted. AFRN III attempted to generate replicas, as is shown in FIG. 17E. Visual comparisons between the data in FIG. 17D and the replicas depicted in FIG. 17E indicate that the two sets of data are not very similar. Further, the error output depicted in FIG. 17F shows clearly that the Reference Set II data should not be classified with Reference Set III. FIG. 17F clearly shows gross errors. Therefore, the data curve in FIG. 17D cannot be categorized as being part of a data category corresponding to Reference Set III.

The above described example demonstrates that once each AFRN element of an array of AFRNs has been trained to replicate a specific category or class of data, each AFRN element will only accurately replicate data that belongs with that class of data. Further each AFRN element fails to accurately replicate data from outside its class of data. Arrays of AFRNs (a group of array elements) can be trained to replicate and categorize groups of data without limitations.

In the chirp example described above, a 100% accuracy rate was achieved in all tests.

In general chirps are mathematically complex and it is difficult to recognize the difference between two chirps by most data manipulating systems. In most real world data analysis systems, the data inputs are mathematically much less complex and easier to recognize than chirps. Therefore, it should be clear that AFRN arrays are even more successful classifying data having simpler mathematical representations. In other words, AFRN arrays classify difficult data easily. Simpler types of data are more easily classified using AFRN arrays.

EXAMPLE TWO

Genotyping

Figure 21:
FIG. 21 is a graph showing an output from a nucleic acid sequencing device showing representation of indications of four dyes labeling nucleic acids.

FIG. 21 is a graph showing an output from a nucleic acid sequencing device showing representation of indications of four dyes labeling nucleic acids. Such graphs are produced by scanners focused on electrophoresis gels with nucleotide fragments. Such scanners are able to identify nucleic acids by the spires in the graphs, each color representing a different nucleic acid. However, consistency of identification of the nucleic acids and/or length of the fragments is uneven even with the most recent equipments. Using an AFRN array, it is possible to improve identification of the output significantly.

Figure 22A:
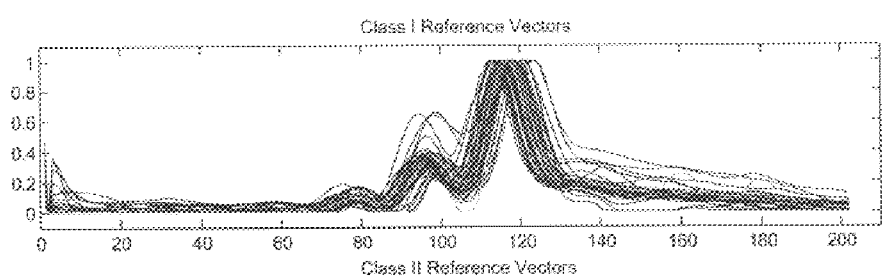
FIGS. 22A, 22B and 22C are classification reference vectors I, II and III produced from scanning the known length of nucleotide sequences.
Figure 22B:
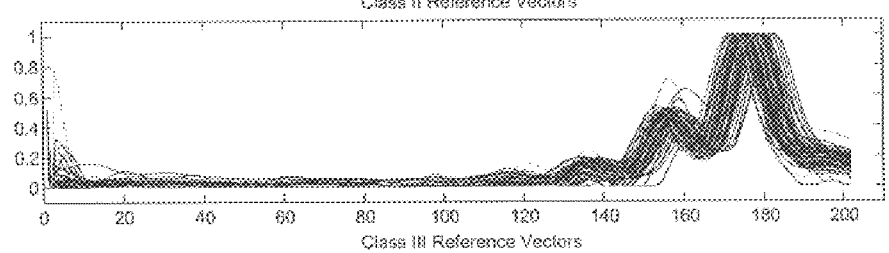
Figure 22C:
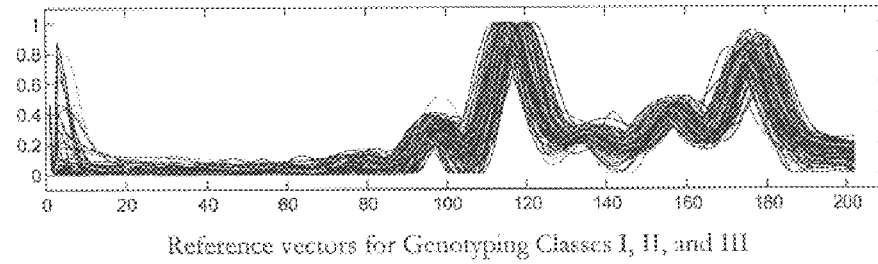

In the present example of the present invention, AFRNs were trained to assist in genotyping where it is necessary to determine the characteristics of nucleic acid fragments. In this example of the invention, three classes of vectors were used to train an AFRN array having three elements. The three classes I, II and III of reference vectors are depicted in FIGS. 22A, 22B and 22C, respectively. Each class I, II and III of reference vectors corresponds to known characteristics of nucleotide sequences. Specifically, class I reference vectors I in FIG. 22B were predetermined to be a first nucleotide sequence characteristic, class II reference vectors in FIG. 22B were predetermined to be a second nucleotide sequence characteristic, and class III reference vectors in FIG. 22C were predetermined to be a third nucleotide sequence characteristic.

Figure 23A:
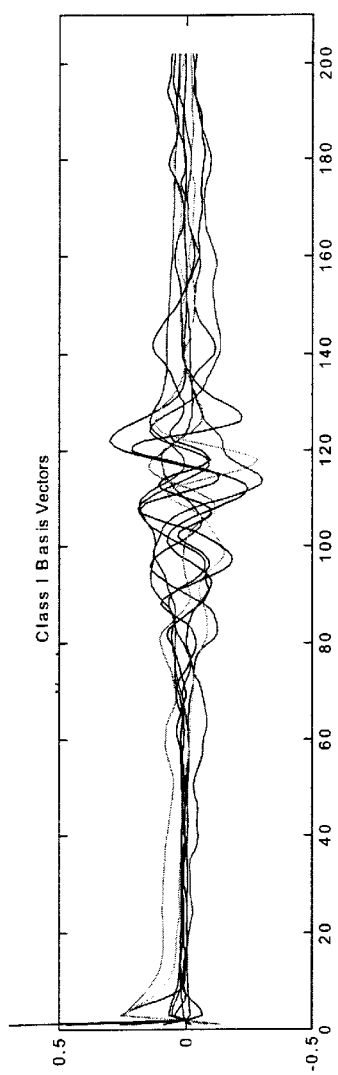
FIGS. 23A, 23B and 23C are basis vectors generated by genotyping AFRNs I, II and III, respectively.
Figure 23B:
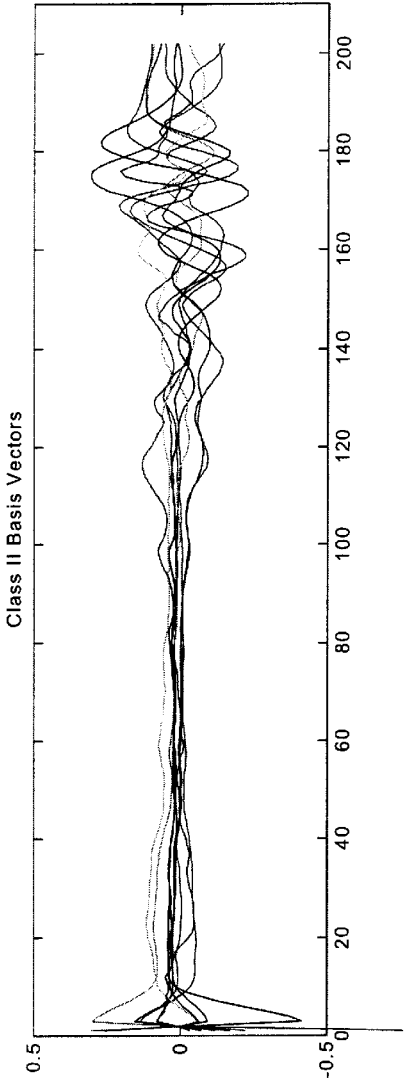
Figure 23C:
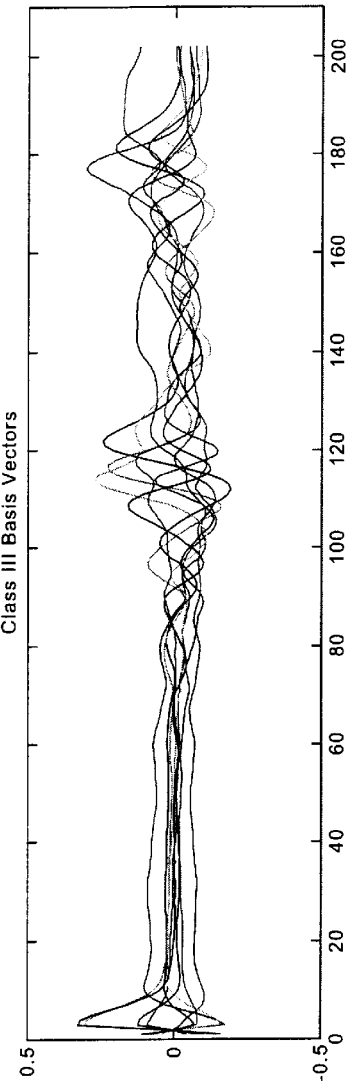

AFRN I was trained to replicate class I reference vectors, AFRN II was trained to replicate class II reference vectors, and AFRN III was trained to replicate class III reference vectors. Basis vectors depicted in FIG. 23A were derived for AFRN I, basis vectors depicted in FIG. 23B were derived for AFRN II, and basis vectors depicted in FIG. 23C were derived for AFRN III.

Figure 24A:
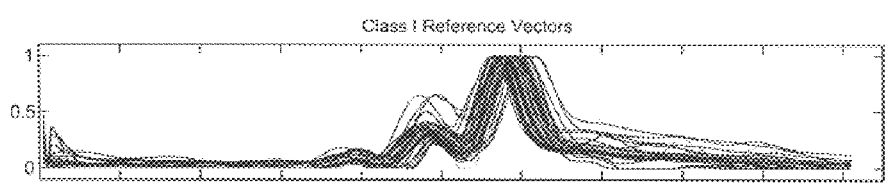
FIGS. 24A, 24B and 24C are classification reference vectors I input into trained genotyping AFRN I, replications of classification reference vectors I generated by AFRN I, and replication error produced by comparing classification reference vectors I and the replications of classification reference vectors I.
Figure 24B:
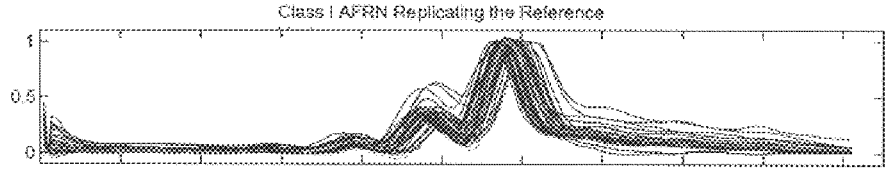
Figure 24C:
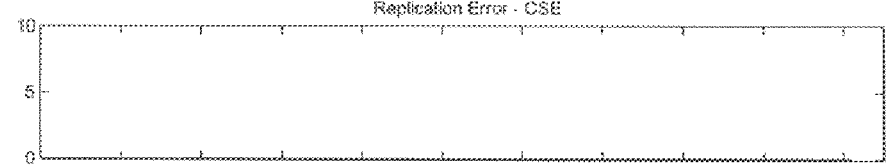

During the training phase, the class I reference vectors depicted again in FIG. 24A, were inputted and AFRN I replicated each vector, as shown in FIG. 24B. An error was determined by comparing the original data with the replicated data, as shown in FIG. 24C. Since all the fines in FIG. 24C are flat, it is clear that AFRN I accurately replicated the vectors and training is complete.

Figure 25A:
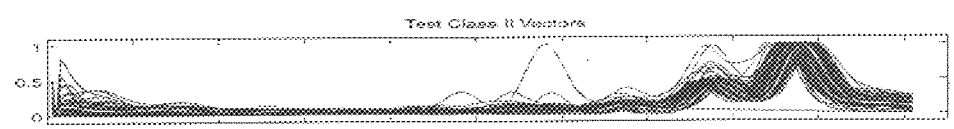
FIGS. 25A, 25B and 25C are classification reference vectors II input into trained genotyping AFRN I, replications of classification reference vectors II generated by AFRN I, and replication error produced by comparing classification reference vectors II and the replications of classification reference vectors II (revealing that one vector is actually a class I vector)
Figure 25B:
Figure 25C:

To test the reliability of AFRN I, a new group of vectors, Test Class II Vectors depicted in FIG. 25A, were initially identified by other means as falling within class II reference vectors. Test Class II Vectors were inputted and AFRN I replicated each inputted vector. The replications were compared to the original vectors and errors were determined, as shown in FIG. 25C. The results in FIG. 25C indicate one vector of Test Class II Vectors falls within the class I reference vectors, as indicated by the single flat fine at the bottom of FIG. 25C. The remaining vectors clearly do not belong with class I reference vectors. As is seen by comparing FIGS. 25A and 25B, one of the vectors is clearly replicated in FIG. 25B and does indeed appear have the same general amplitude peaks as the class I reference vectors in FIG. 22A. Therefore, the classification of this vector by the previously used method of classification is in doubt. Visual inspection of the accurately reproduced vector confirm that this vector belongs with class I reference vectors.

Figure 26A:
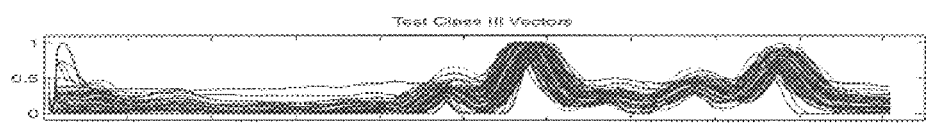
FIGS. 26A, 26B and 26C are classification reference vectors III input into trained genotyping AFRN I, replications of classification reference vectors III generated by AFRN I, and replication error produced by comparing classification reference vectors III and the replications of classification reference vectors III.
Figure 26B:
Figure 26C:

Another test of the testing of AFRN I is shown in FIGS. 26A, 26B and 26C. The class III reference vectors are shown again in FIG. 26A. FIG. 26B shows replications of the class III reference vectors generated by AFRN 1. Comparison of the original vectors with the replicas yields the error graph in FIG. 26C. Clearly, none of the vectors replicated by AFRN I shown in FIG. 26B belong with class I reference vectors.

Similar tests were conducted using AFRNs II and III with identical results. The AFRNs of the present invention only replicated data that belonged in the class the AFRN was trained to replicate.

From the above examples of applications of the present invention, it is clear that AFRN arrays may be trained and then used to replicate specific types of data. Data that is accurately replicated is classified within the class used to train the successful AFRN.

In another embodiment of the present invention, the AFRN array may automatically expand its capabilities by determining that a new AFRN array element needs to be created. Specifically, FIG. 27 is a flowchart showing steps for automatically refining and expanding the data analysis system of the present invention.

Figure 27:
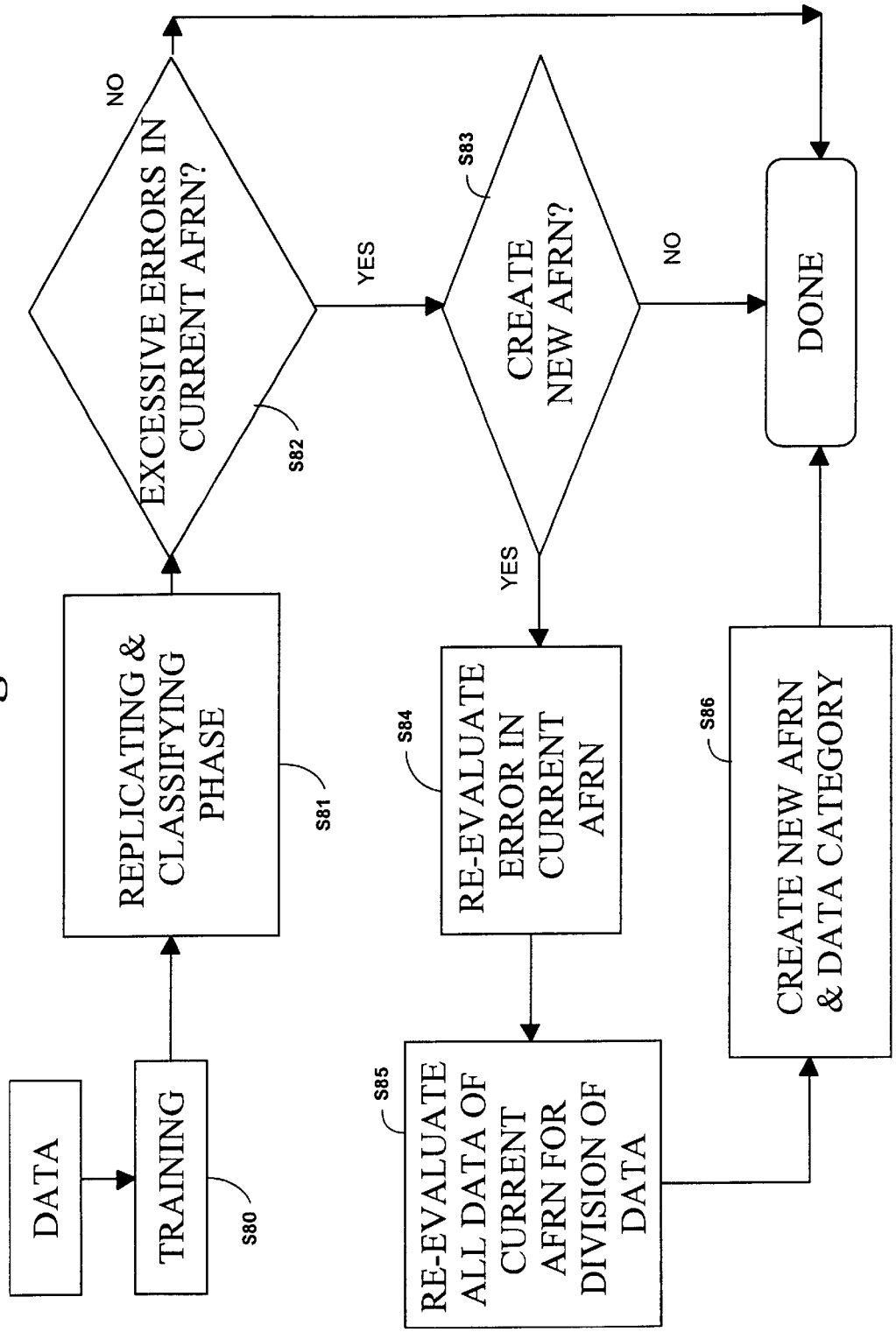
FIG. 27 is a flowchart showing another embodiment of the invention, showing steps for automatically refining and expanding the data analysis system depicted in FIGS. 6 and 7.

In FIG. 27, at step S80, data inputted is used to train an AFRN array, as described above with respect to FIG. 6. In step S81, the trained AFRN array replicates and thereby classifies data, as is described above with respect to FIG. 7. Repeated iterations of the steps in FIG. 7 generate significant amounts of data classification and error. After a predetermined amount of time or after a predetermined threshold of data has been replicated and classified, a determination is made at step S82 whether or not any array elements in the trained AFRN array has identified and classified an excessive amount of data. If yes, then another determination is made at step S83 whether or not a current AFRN needs a reduction in error threshold and a new AFRN should be created. If yes, then a new error threshold is generated at step S84. Next, in step S85, all of the data classified by that particular AFRN is re-evaluated (replicated) with a new smaller threshold of error to determine the amount of data that would remain classified by the AFRN and determine the amount of data that is to be separated and classified in a new classification of data. In step S86, the new classification category is defined and a new AFRN created. Thereafter, the AFRN array returns to a mode where classification of data continues.

It will be understood from the following description, that the present invention is applicable to a variety of data classification applications. For instance, the AFRN arrays of the present invention may be used in gene sequencing systems, speech recognition systems, optical recognition systems, informatics, radar systems, sonar systems, signal analysis and many other digital signal processing applications.

Various details of the present invention may be changed without departing from its spirit or its scope. Furthermore, the foregoing description of the embodiments according to the present invention are provided for illustration only, and not for the purpose of limiting the invention as defined by the appended claim and their equivalents.

What is claimed is:

1. A method for classifying types of data in a data set, comprising the steps of:
   training a computer to identify a plurality of types of original data;
   inputting new data into the computer;
   creating a replica of the new data;
   confirming accuracy of replicated data;
   classifying the new data in response to confirmation of accurate replication;
   wherein said training step comprises the steps of:
      inputting several previously identified data sets into a computer;
      creating within the computer a plurality of basis vector sets, each basis vector set comprising a plurality of basis vectors, each basis vector set being in one to one correspondence with the identified data sets;
      creating comparison data sets using the basis vector sets;
      comparing the previously identified data sets with the comparison data sets;
      computing an error from said comparison;
      determining acceptability of the error; and
      repeating said creating of the basis vector set in response to the error being unacceptable.

2. A method for classifying data as set forth in claim 1, further comprising:
   constructing replicas of the data based upon the training; and
   comparing the constructed replica data with the original data to confirm reliability of said training.

3. A method for classifying data as set forth in claim 1, wherein the computer comprises a plurality of computers.

4. A method for classifying data as set forth in claim 3, wherein the plurality of computers are connected via a network.

5. A method for classifying data as set forth in claim 1, wherein the computer comprises a plurality of microprocessors working in close communication with one another.

6. A method for classifying data as set forth in claim 1, further comprising the step of determining the need for new classifications of data.

7. A method for identifying types of data in a data set, comprising the steps of:
   a) inputting previously identified data sets into a computer;
   b) creating within the computer a plurality of basis vector sets in one to one correspondence with data sets;
   c) inputting new data into the computer;
   d) generating replicas of the new data using the basis vector sets;
   e) comparing the replicas with the new data;
   f) generate an error based upon the comparison of the new data and the replicas;
   g) determine acceptability of error; and
   h) classify the new data in an appropriate class of data in response to determination of acceptable error.

8. A method for identifying types of data as set forth in claim 7, further comprising the steps of:
   after step b) creating comparison data sets using basis vector sets, respectively;
   comparing the identified data sets with comparison data sets respectively;
   computing an error from said comparison;
   determining acceptability of the error;
   repeating said creating of the basis vector set in response to the error being unacceptable; and
   allowing input of unknown data in response to completion of a training phase.

9. A computer system for replicating and classifying data, comprising:
   a microprocessor adapted for:
      training to replicate predetermined groups of data thereby:
         creating within the computer system a plurality of basis vector sets in one to one correspondence with predetermined data sets as a part of said training;
      receiving inputted unknown data;
      replicating the unknown data using one of the basis vector sets;
      comparing the unknown data with the replicated data to determine the accuracy of the replication process; and
      in response to confirmation of accurate duplication, classifying the unknown data in one of the predetermined sets of data.

10. A computer system for replicating and classifying data as set forth in claim 9, wherein said microprocessor is further adapted for:
   generating an error based upon said comparing of the unknown data and the replica of that data; and
   using the generated error to confirm the accuracy of the duplication.

11. A computer system for replicating and classifying data as set forth in claim 10, wherein said microprocessor is further adapted for determining if said error needs revision and determining whether further basis vector sets are required for classifying data.

12. A computer system for replicating and classifying data as set forth in claim 9, wherein said microprocessor comprises a plurality of microprocessors linked to one another.

13. A computer system for replicating and classifying data as set forth in claim 12, wherein said microprocessors are linked to one another via a negotiator.

14. A computer system for replicating and classifying data as set forth in claim 12, wherein said microprocessors are linked to one another for symmetric multiprocessing.

15. A computer system for replicating and classifying data as set forth in claim 12, wherein said microprocessors are linked to one another for asymmetric multiprocessing.

16. A computer system for replicating and classifying data as set forth in claim 12, wherein said microprocessors are linked to one another at chip level.

17. A computer system for replicating and classifying data as set forth in claim 12, wherein said microprocessors are linked to one another in a network.

18. A computer system for replicating and classifying data as set forth in claim 12, wherein said microprocessors are linked to one another in clusters.

19. A computer system for replicating and classifying data as set forth in claim 12, wherein said computer system is configured for genotyping.

20. A method for classifying data, comprising the steps of:
 a) training a computer to replicate data sets, said training step including defining a plurality of replicators, each of said replicators being trained to replicate one data set of said data sets;
 b) inputting new data into said computer;
 c) replicating said new data with each of said replicators;
 d) comparing replicated data from a first of said replicators with said new data to determine accuracy of said replicated data replicated by said first of said replicators within a predetermined error threshold;
 e) repeating step d) for each of said replicators;
 f) determining if one of the comparisons in steps d) and e) yielded confirmation of accurate replication for one of said replicators; and
 g) classifying the new data in response to determination of accurate replication by one of said replicators in step f).

21. The method for classifying data as set forth in claim 20, further comprising the step of determining the need for one or more new replicators in response to a predetermined threshold amount of data classification by any one of said replicators.

22. The method for classifying data as set forth in claim 20, wherein said training step comprises the steps of:
 inputting several previously identified data sets into a computer;
 creating within the computer a plurality of basis vector sets, one basis vector set for each of said replicators, each of said basis vector sets comprising a plurality of basis vectors, each of said basis vector sets being determined in order to enable the corresponding replicator to replicate within the predetermined threshold of error for the corresponding identified data set from said identified data sets;
 wherein creating a basis vector set for each of said replicators comprises:
  creating a comparison data set using the corresponding basis vector set;
  comparing the previously identified data set with the comparison data set;
  computing an error from said comparison;
  determining acceptability of the error; and
  repeating said creating of the basis vector set in response to the error being unacceptable.

23. The method as set forth in claim 22 wherein in said creating step, the basis vector sets are generated from any combination of the following: chirplets, wavelets, Fourier based functions, Fractal basis functions, radial basis functions, basis functions generated using multi-layer perceptrons, and other computer generated basis functions.

24. A method for identifying data sets, comprising the steps of:
 a) inputting previously identified data sets into a computer;
 b) creating within the computer a plurality of basis vector sets in one to one correspondence with said previously identified data sets, each basis vector set defining a replicator;
 c) inputting a new data set into said computer;
 d) for each replicator, generating a replica of said new data set using the basis vector sets;
 e) comparing the replica generated by the first replicator of the plurality of replicators with said new data set;
 f) determining acceptable replication of said new data set generated by the first replicator using a predetermined error threshold;
 g) repeating steps e) and f) for each of the replicators and the replica generated by the corresponding replicator;
 h) determining if more than one replicator acceptably replicated said new data set in repeated steps f);
 i) tagging said new data set for human analysis in response to a determination in step h) that more than one replicator acceptably replicated said new data set;
 j) classifying the new data in response to determination in step h) that only one replicator acceptably replicated said new data set.

25. The method for classifying data as set forth in claim 24, further comprising the step of determining the need for new replicators in response to a predetermined threshold amount of data classification.

26. The method for classifying data as set forth in claim 24, further comprising the step of tagging the new data for human analysis in response to a determination in step h) that no replicator acceptably replicated the new data.

27. The method for classifying data as set forth in claim 24, further comprising the step of determining the need to automatically create a new replicator in response to a failure of all the replicators to create a replica of the data below a set threshold error.

28. A computer system for replicating and classifying data, comprising:
 a microprocessor adapted for:
  training to replicate predetermined sets of data thereby creating a plurality of replicators, each replicator trained to replicate one set of data of the predetermined sets of data,
  receiving unknown data,
  having each of the replicators attempt to replicate the unknown data,
  for each replicator comparing the unknown data with the replicated data;
  determining whether each replicator acceptably reproduced the unknown data within a predetermined threshold of error; and
  in response to determination of acceptable replication by only one replicator, classifying the unknown data in one of the predetermined sets of data.

29. The computer system for replicating and classifying data as set forth in claim 28, wherein said microprocessor is further adapted for determining if the threshold error for any one replicator needs revision in response to significant amounts of data classification by that one replicator.

30. The computer system for replicating and classifying data as set forth in claim 29, wherein said microprocessor is further adapted for determining whether new replicators and corresponding basis vector sets are required for classifying data.

31. The computer system for replicating and classifying data as set forth in claim 28, wherein said microprocessor comprises a plurality of microprocessors linked to one another.

32. The computer system for replicating and classifying data as set forth in claim 31, wherein said microprocessors are linked to one another via a negotiator.

33. The computer system for replicating and classifying data as set forth in claim 31, wherein said microprocessors are linked to one another for symmetric multiprocessing.

34. The computer system for replicating and classifying data as set forth in claim 31, wherein said microprocessors are linked to one another for asymmetric multiprocessing.

35. The computer system for replicating and classifying data as set forth in claim 31, wherein said microprocessors are linked to one another at chip level.

36. The computer system for replicating and classifying data as set forth in claim 31, wherein said microprocessors are linked to one another in a network.

37. The computer system for replicating and classifying data as set forth in claim 31, wherein said microprocessors are linked to one another in clusters.

38. The computer system for replicating and classifying data as set forth in claim 31, wherein said computer system is configured for genotyping.

\* \* \* \* \*

UNITED STATES PATENT AND TRADEMARK OFFICE
CERTIFICATE OF CORRECTION

PATENT NO. : 6,601,050 B1
DATED : July 29, 2003
INVENTOR(S) : Wasyl Malyj

It is certified that error appears in the above-identified patent and that said Letters Patent is hereby corrected as shown below:

Column 2,
Line 35, replace "Ehner" with -- Elmer --;
Line 46, replace "electropherograxn" with -- electropherogram --;
Line 63, replace "stiff" with -- still --.

Column 3,
Line 43, replace "JEPG" with -- JPEG --.

Column 9,
Line 57, replace "&fling" with -- falling --.

Column 12,
Line 65, replace "163D" with -- 16D --.

Column 14,
Line 25, replace "fines" with -- lines --;
Line 36, replace "fine" with -- line --.

Signed and Sealed this

Twenty-third Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,601,050 B1
DATED : July 29, 2003
INVENTOR(S) : Wasyl Malyj

It is certified that error appears in the above-identified patent and that said Letters Patent is hereby corrected as shown below:

Title page,
Item [73], Assignee, replace "Large Scale Biology Corporation" with -- Marti Nelson Medical Foundation --.

Column 2,
Line 35, replace "Ehner" with -- Elmer --;
Line 46, replace "electropherograxn" with -- electropherogram --
Line 63, replace "stiff" with -- still --.

Column 3,
Line 43, replace "JEPG" with -- JPEG --

Column 9,
Line 57, replace "&fling" with -- falling --.

Column 12,
Line 65, replace "163D" with -- 16D --.

Column 14,
Line 25, replace "fines" with -- lines --;
Line 36, replace "fine" with -- line --.

Signed and Sealed this

Eleventh Day of May, 2004

JON W. DUDAS
*Acting Director of the United States Patent and Trademark Office*